US007314858B2

(12) United States Patent
Lehrer et al.

(10) Patent No.: US 7,314,858 B2
(45) Date of Patent: *Jan. 1, 2008

(54) RETROCYCLINS: ANTIVIRAL AND ANTIMICROBIAL PEPTIDES

(75) Inventors: Robert I. Lehrer, Santa Monica, CA (US); Alan J. Waring, Irvine, CA (US); Alexander M. Cole, Orlando, FL (US); Teresa B. Hong, El Monte, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/982,145

(22) Filed: Nov. 5, 2004

(65) Prior Publication Data

US 2005/0272645 A1 Dec. 8, 2005

Related U.S. Application Data

(63) Continuation-in-part of application No. PCT/US03/14106, filed on May 6, 2003, which is a continuation-in-part of application No. 10/141,645, filed on May 6, 2002, now Pat. No. 6,713,078, which is a continuation-in-part of application No. PCT/US02/12353, filed on Apr. 18, 2002.

(60) Provisional application No. 60/284,855, filed on Apr. 18, 2001.

(51) Int. Cl.
*A61K 38/00* (2006.01)
*C07K 7/00* (2006.01)
*C07K 7/04* (2006.01)
*C07K 7/64* (2006.01)

(52) U.S. Cl. ............ 514/2; 514/9; 514/15; 530/300; 530/317; 530/326; 530/328

(58) Field of Classification Search .......... 514/2, 514/9, 13, 15, 21; 530/300, 317, 321, 326, 530/328; 424/405
See application file for complete search history.

(56) References Cited

U.S. PATENT DOCUMENTS

| | | |
|---|---|---|
| 5,459,235 A | 10/1995 | Selsted |
| 5,464,823 A | 11/1995 | Lehrer |
| 5,804,558 A | 9/1998 | Lehrer |
| 5,916,872 A | 6/1999 | Chang |
| 6,008,195 A | 12/1999 | Selsted |
| 6,159,936 A | 12/2000 | Lehrer |
| 6,335,318 B1 | 1/2002 | Selsted |
| 2002/0015697 A1 | 2/2002 | Beckman |
| 2003/0022829 A1 | 1/2003 | Maury |

FOREIGN PATENT DOCUMENTS

WO   WO 00/68265   * 11/2000

OTHER PUBLICATIONS

Bowie et al., "Deciphering the Message in Protein Sequences: Tolerance to Amino Acid Substitutions," Science, vol. 247 No. 4948, pp. 1306-1310 (Mar. 1990).*
Tran et al., "Homodimeric -Defensins from Rhesus macaque Leukocytes," Journal of Biological Chemistry, vol. 277 No. 5, pp. 3079-3084 (Feb. 2002).*
Cole et al., "Retrocyclin: A primate peptide that protects cells from infection by T- and M-tropic strains of HIV-1," Proceedings of the National Academy of Sciences, USA, vol. 99 No. 4, pp. 1813-1818 (Feb. 2002).*
Tang et al., A Cyclic Antimicrobial Peptide Produced in Primate Leukocytes by the Ligation of Two Truncated $_\alpha$-Defensins, Science, 1999, 286: 498-502.
Tam et al., Membranolytic Selectivity of Cysteine-Stabilized Cyclic Protegrins, eur. J. Biochem., 267: 3289-3300, 2000.
Gudmundsson et al., Neutrophil Antibacterial Peptides, Multifunctional Effector Molecules in the Mammalian Immune System, 1999, J. Immunol. Methods, 232(1-2): 45-54.
Hancock et al., Cationic Peptides: A New Source of Antibiotics, 1998, Trends in Biotech., 16: 82-88.
Harwig et al., Gallinacins: Cysteine-Rich Antimicrobial Peptides of Chicken Leukocytes, 1994, FEBS Lett., 342: 281-285.
Lehrer et al., Defensins: Antimicrobial and Cytotoxic Peptides of Mammalian Cells, 1992, Ann. Rev. Immunol., 11:105-128.
Liu et al., The Human Beta-Defensin-1 and Alpha-Defensins are Encoded by Adjacent Genes: Two Peptide Families With Differing Disulfide Topology Share a Common Ancestry, 1997, Genomics, 43: 316-320.
Palfree et al., Human Defensin Multigene Family: A Genomic Fragment Containing the HP-1 Gene and an Upstream Related Pseudogene, 1994, GenBank, U10267.
Polley et al., Chromosome 8 Genomic Sequence, 2004, GenBank, AF238378.
Schonwetter et al., Epithelial Antibiotics Induced at Sites of Inflammation, 1995, Science, 267: 1645-1648.
Schroeder et al., Epithelial Antimicrobial Peptides: Innate Local Host Response Elements, 1999, Cell. Mol. Life Sci., 56: 32-46.
Wilson et al, Ex Vivo Expansion of CD4 Lymphocytes From Human Immunodeficiency Virus Type 1-Infected Persons in the Presence of Combination Antiretroviral Agents, 1999, J. Infect. Dis., 172: 88-96.

(Continued)

*Primary Examiner*—Zachariah Lucas
(74) *Attorney, Agent, or Firm*—Bozicevic, Field & Francis LLP; Pamela J. Sherwood

(57) ABSTRACT

Retrocyclin peptides are small antimicrobial agents with potent activity against bacteria and viruses. The peptides are nonhemolytic, and exhibit minimal in vitro cytotoxicity. A pharmaceutical composition comprising retrocyclin as an active agent is administered therapeutically to a patient suffering from a bacterial and/or viral infection, or to an individual facing exposure to a bacterial and/or viral infection, especially one caused by the HIV-1 retrovirus or other sexually-transmitted pathogens.

8 Claims, 24 Drawing Sheets

OTHER PUBLICATIONS

Wong et al., Recovery of Replication-Competent HIV Despite Prolonged Suppression of Plasma Viremia, 1995, Science, 278: 1291-1295.

Yang et al., 1999, J. Virol., 73, 4582-4589.

Yang et al., [beta]-Defensins; Linking Innate and Adaptive Immunity Through Dendritic and T Cell CCR6, Science, 1999, 286: 525-528.

Zimmerman et al., 1995, Biochemistry, 34: 13663-13671.

Wang et al., Retrocyclin, an Antiretroviral θ-Defensin, Is a Lectin[1], J. of Immunology, 2003, 170: 4708-4716.

Yasin et al., θ Defensins Protect Cells from Infection by Herpes Simplex Virus by Inhibiting Viral Adhesion and Entry, J. of Virology, 2004, 78(10): 5147-5156.

* cited by examiner

FIG. 2

```
Demidefensin-1      MRTFALLTAMLLLVALHAQAEAROQARADEAAAQQQPGADDQGMAHSFTRPENAAL    55
                    ||||||||||||||| ||  |||||||||||  ||||||||  ||| | ||||||
Human Retrocyclin 1 MRTFALLTAMLLLVAL●AQAEPLQARADEAAAQEQPGADDQEMAHAFTWHESAAL    55

Demidefensin-1      PLSESARGL RCLCRRGVQ QLL●RRLGSCAFRG●LCRICCR●                96
                    |||| ||||  || ||||  |||  || |||||||  || |||
Human Retrocyclin 1 PLSDSARGL RCICGRGIC RLL●RRFGSCAFRGTLHRICCR●               96
```

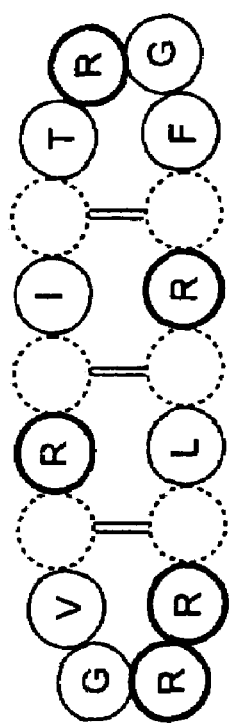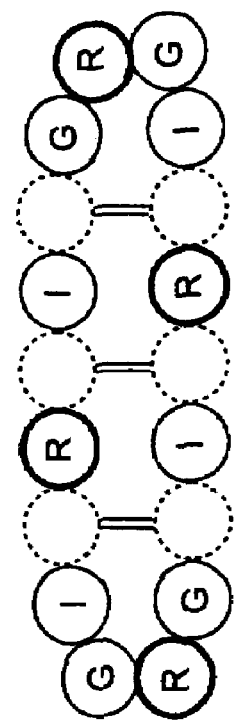
FIG. 3C
FIG. 3D
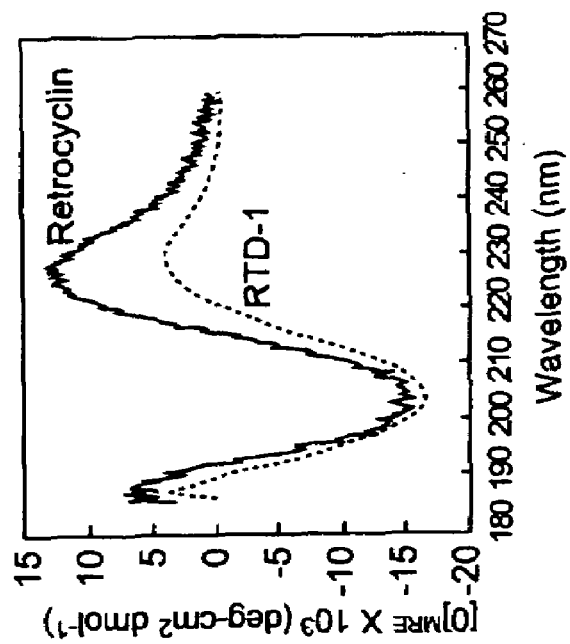
FIG. 3A
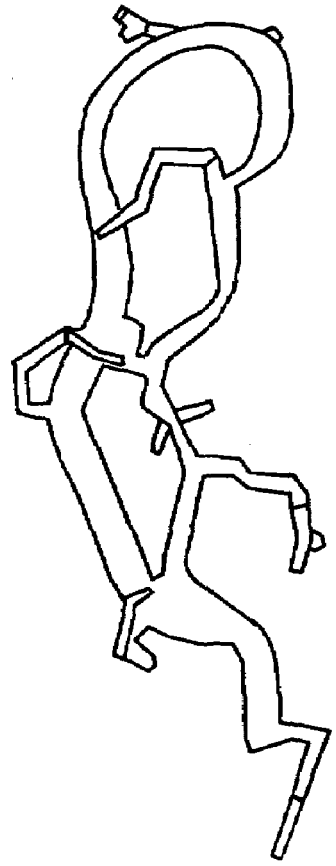
FIG. 3B

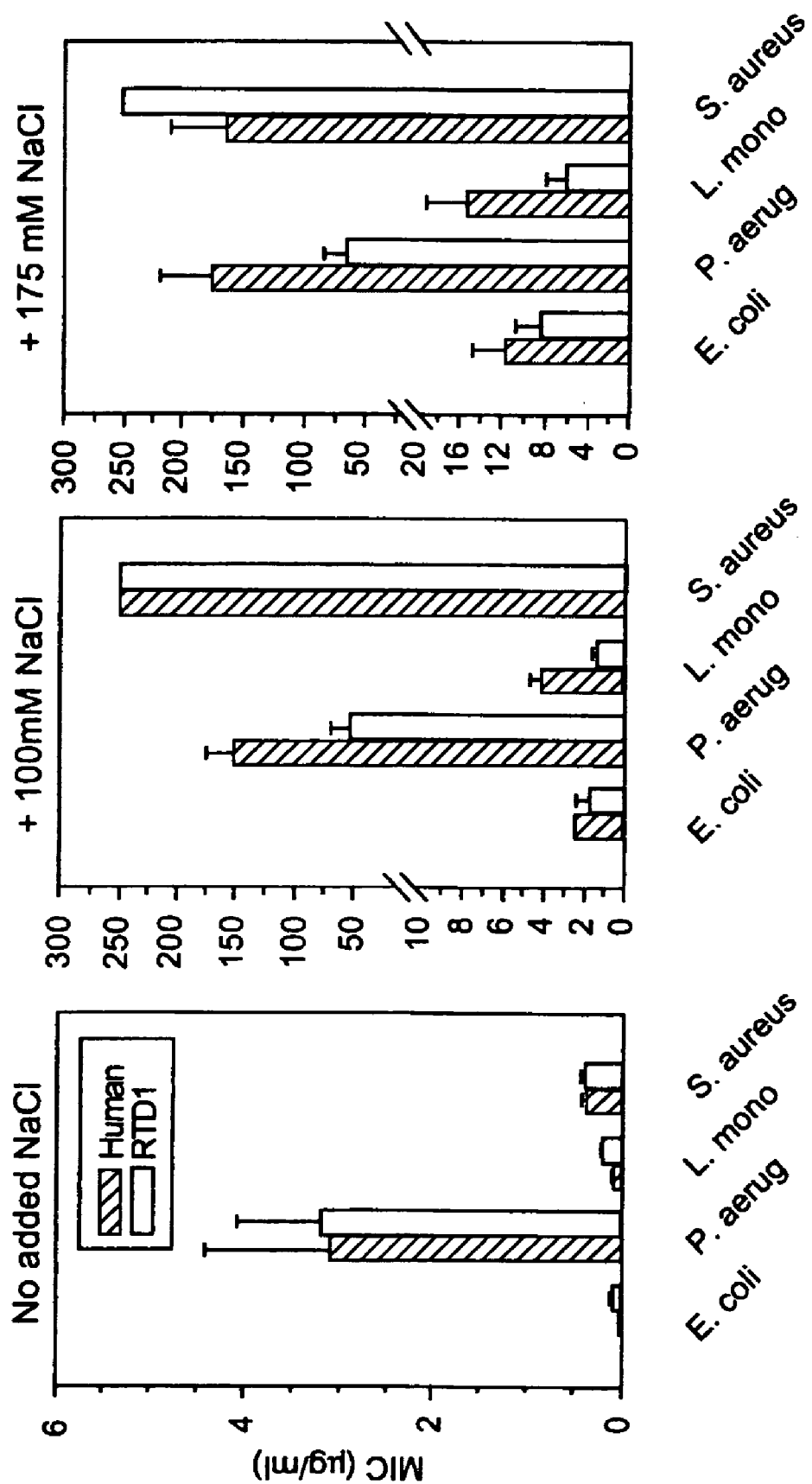

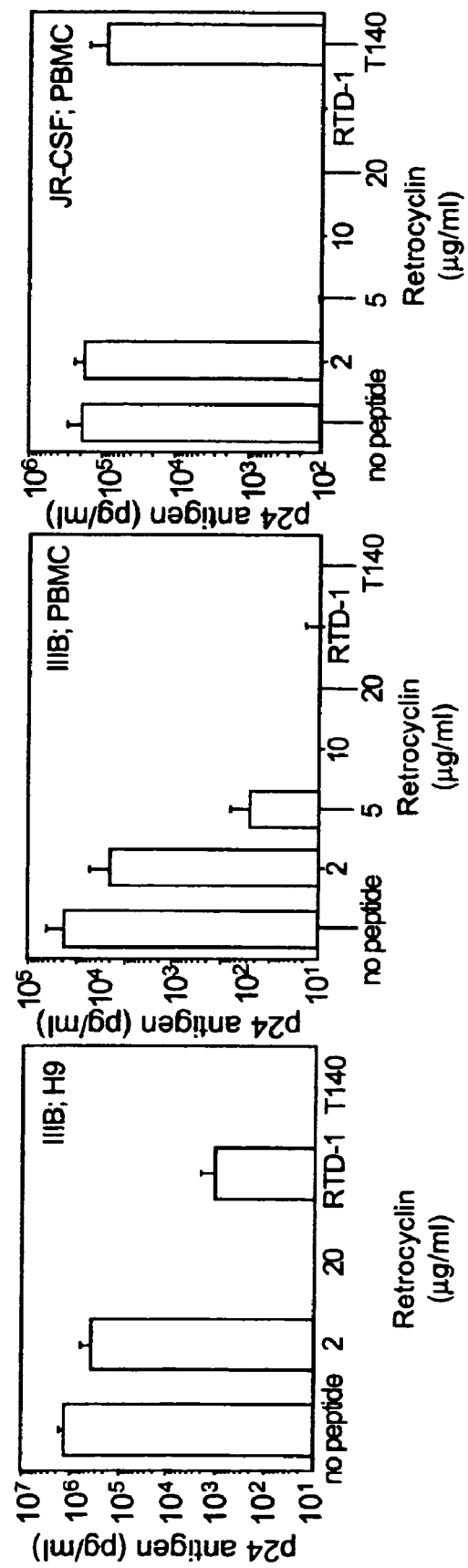

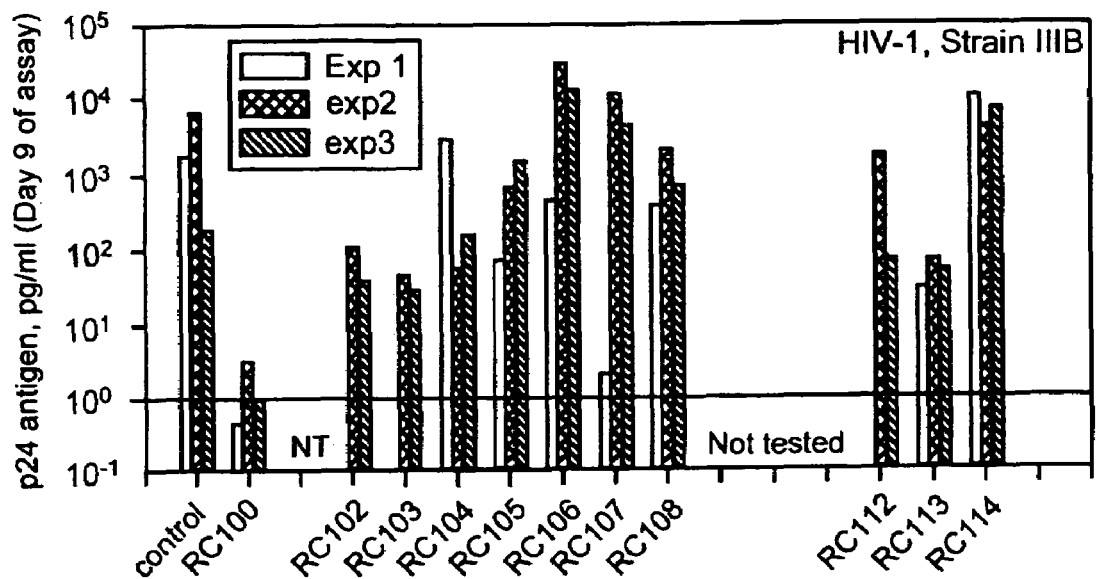
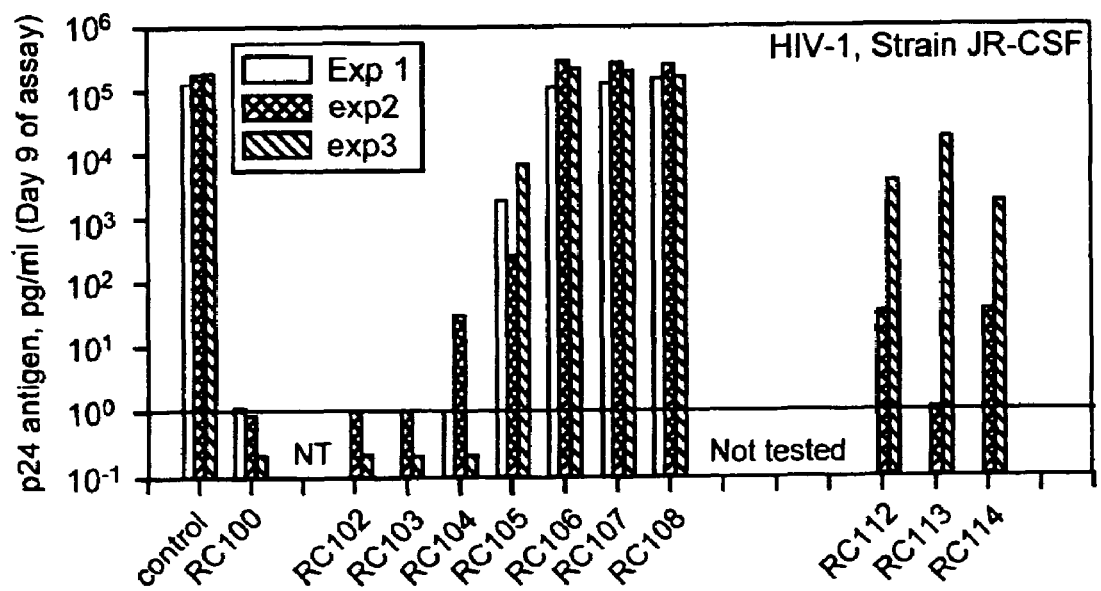

FIG. 10A
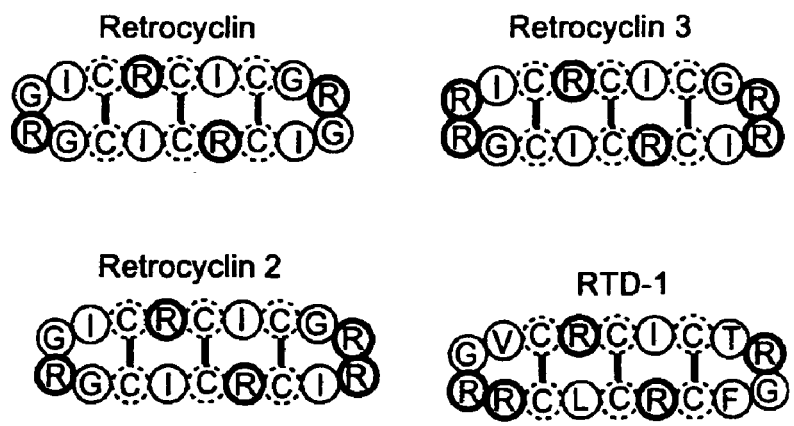
FIG. 10B
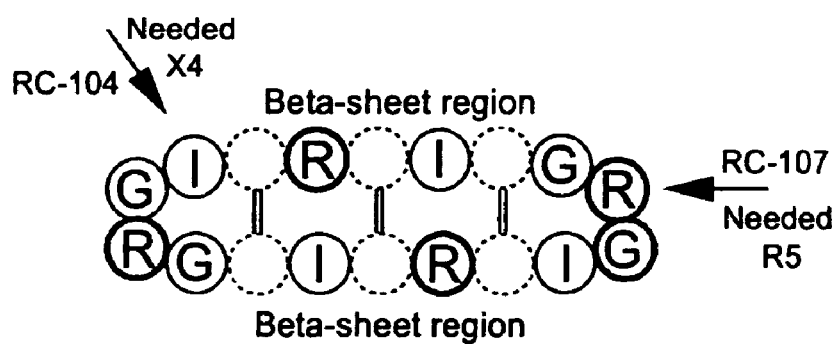
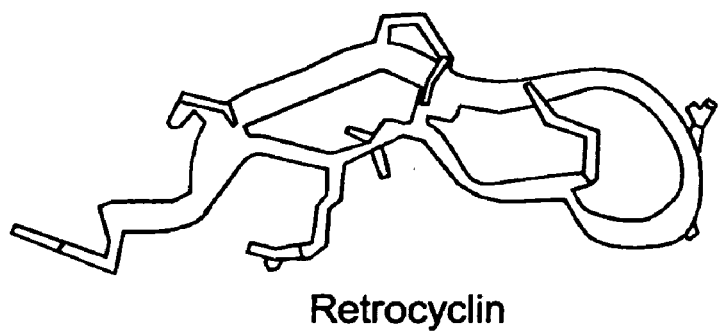
Retrocyclin

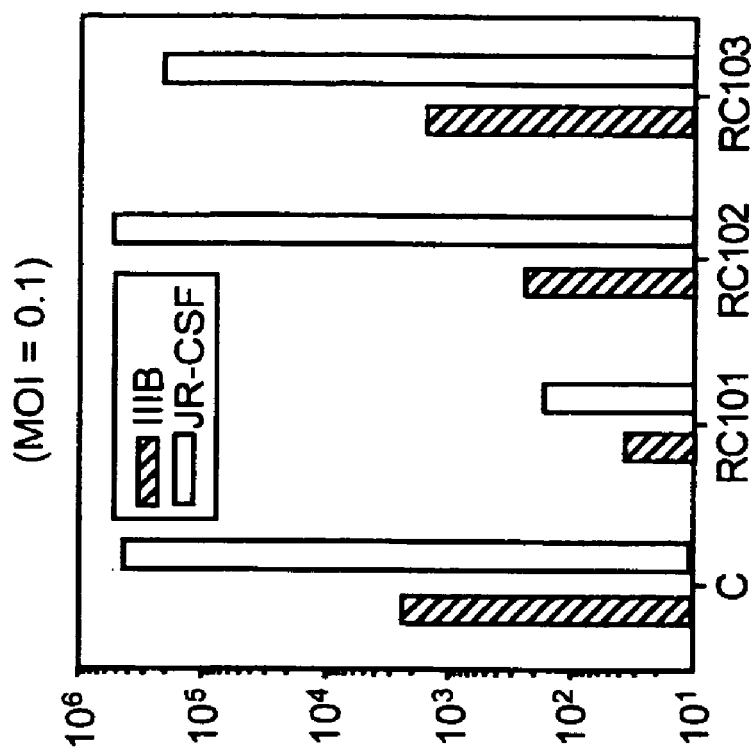
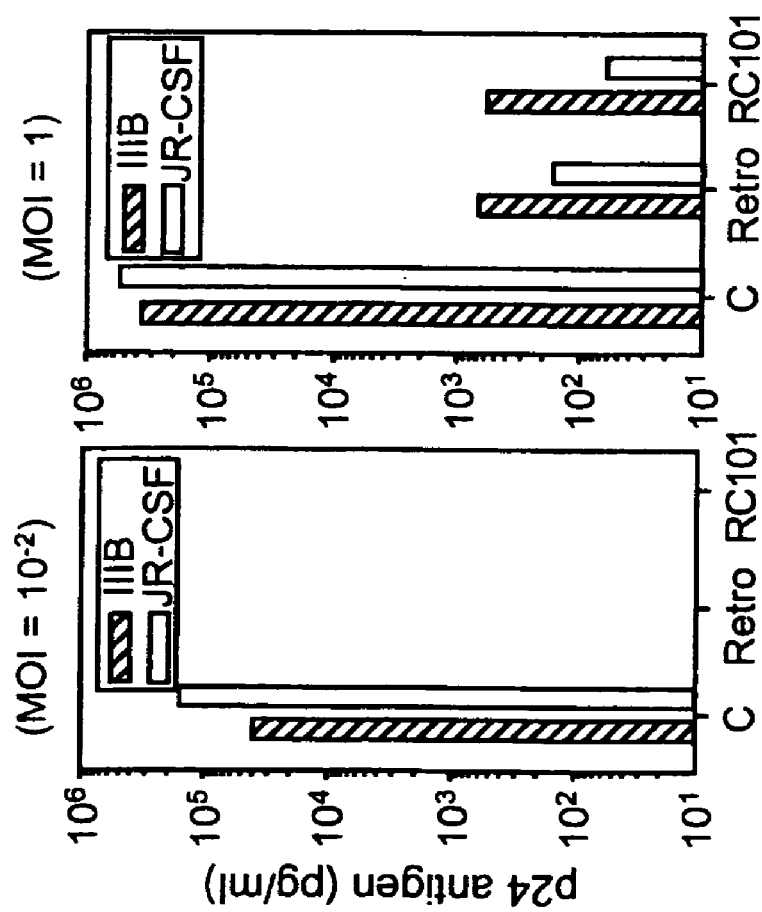

FIG. 15A

Translation and Alignment of Human and Orangutan retrocyclin gene sequences

```
(SEQ ID NO 65) Human:    VTPAMRTFALLTAMLLLVAL•AQAEPLQARADEAAAQEQPGADDQEMAHAFTWHESAALPLSDSARGLRCICGRGICRLL•RRFGSCA
(SEQ ID NO 66) Orang 19: VTPAMRTFALLAMLLLVAL•AEAEPLQARADETAAQEQPGADDQEMAHAFTWRESATLPLSDSARGLRCICRRGVCRFL•RHLGSCA
(SEQ ID NO 67) Orang 20: VTPAMRTFYLAMLLYVLQAQAEPLRARADETAAQEQPGADDQEMAHAFTWRESAALPLSDSARGLRCICRRGVCRFL•RHLGSCA
(SEQ ID NO 68) Orang 21: VTPAMRTFYLAMLLYVLQAQAEPLRARADETAAQEQPGADDQEMAHAFTWRESAALPLSDSARGLRCICRRGVCRLL•RHFGSCA

FIG. 15B

Translation and Alignment of Human and Chimpanzee retrocyclin gene sequences

```
(SEQ ID NO 65) Human:    VTPAMRTFALLTAMLLLVAL●AQAEPLQARADEAAAQEÇPGADDQEMAHAPTWHESAALPLSDSARGLRCICGRGICRLL●RRFGSCA
(SEQ ID NO 70) P. trog   VTPAMRTFALLTAMLLLVAL●AQAEPLQARADEAAAQEÇPGADDQEMAHAPTWDESAALPLSDSARGLRCIGGRGICGLLQRRFGSCA
(SEQ ID NO 71) P. pani.  VTPAMRTFALLTAMLLLVAL●AQAEPLQARADEAAAQEÇPGADDQEMAHAFTWDESAALPLSDSARGLRCIGGRGICGLLQRRVGSCA RC100 is retrocyclin-1 and RC100b is Retrocyclin-2. The sequences of RC101, Orang 1&2 and RC 123D are shown in the accompanying Table.

RETROCYCLINS: ANTIVIRAL AND ANTIMICROBIAL PEPTIDES

This invention was made with Government support under contract A122839 awarded by the National Institutes of Health. The Government has certain rights in this invention.

BACKGROUND

Natural polycationic antimicrobial peptides have been found in many different species of animals and insects and shown to have broad antimicrobial activity. In mammals, these antimicrobial peptides are represented by two families, the defensins and the cathelicidins. Nearly all of these peptides have membrane affinity, and can permeate and permeabilize bacterial membranes, resulting in injury, lysis, and/or death to the microbes. In particular, the human peptides known as defensins are produced by mammalian and avian leukocytes (e.g. neutrophils, some macrophages) and epithelial cells.

Three defensin subfamilies exist in vertebrates: alpha-defensins, beta-defensins, and circular (theta) minidefensins. All derive from an ancestral gene that existed before reptiles and birds diverged, contain six cysteines, and have largely beta-sheet structures that are stabilized by three intramolecular disulfide bonds. RTD-1, a theta minidefensin, was recently detected in bone marrow from the rhesus monkey, *Macacca mulatta*. It had 18 residues and was circular, having been formed by the fusion of two truncated alpha-defensin precursors ("demidefensins") each of which contributed 3 cysteines to the mature peptide. It is not yet known if the cellular machinery responsible for processing these precursors remains operational in human leukocytes.

Alpha-defensins are largely beta sheet peptides that contain 29-35 amino acid residues, including 6 cysteines that form three intramolecular disulfide bonds. Because of the nature of the cysteine pairings, the molecules are effectively macrocyclic. Four of these α-defensins, HNP 14, occur primarily in human neutrophils. HD-5 & 6 are found in Paneth cells, specialized cells of the small intestine's crypts. Human α-defensin genes contain three exons and two introns and are clustered on chromosome 8p23. They encode preprodefensins that contain ~100 residues which include a signal peptide, a polyanionic propiece and the C-terminal defensin domain. Mature defensins are processed by sequential proteolysis.

Beta defensins are generally larger than α-defensins (3540 residues) and may also be more ancient, since they occur in birds as well as mammals. Beta defensins are expressed in many different types of epithelial cells, and in some glands. In some cases, expression is constitutive; in others, it is inducible. Several β-defensin genes are located on 8 p23, adjacent to the α-defensin genes-consistent with their common evolutionary ancestry. The disulfide pairing motif of beta defensins differs from that of α-defensins, however α and β-defensins have generally similar shapes.

The three-dimensional structure of many defensins comprises a complexly folded amphiphilic beta-sheet, with the polar face formed by its arginines and by the N- and C-terminal residues playing an important role in defining microbicidal potency and the antimicrobial spectrum. The antimicrobial effects of defensins are derived from their ability to permeabilize cell membranes and interact with viral envelopes, thereby exposing contents of the microorganism to the environment or abrogating viral infectivity. (See Gudmundsson et al. (1999) *J Immunol Methods* 232 (1-2):45-54.) Antimicrobial peptides are reviewed by Hancock and Lehrer (1998) *Trends in Biotechnology* 16:82.

In general, the antiviral activities of antimicrobial peptides have not been extensively investigated. Although studies have reported that antimicrobial peptides, such as human neutrophil-derived defensins (α-defensins), are directly virucidal against herpes simplex virus (HSV), and adenovirus strains, only a few reports deal with anti-HIV-1 activity. T22 and T140, analogs of polyphemusins (peptides from horseshoe crabs), are active in inhibiting HIV-1 replication through binding to the chemokine receptor CXCR4. However, these peptides only inhibit the T cell-tropic (T-tropic; X4) strains that utilize CXCR4 as a coreceptor for entry and they are ineffective against strains that utilize CCR5 for entry (macrophage (M)-tropic "R5" viruses). Since sexual transmission is largely attributed to R5 infection, the potential of T22 and T140 as topical vaginal or rectal microbicides is limited.

One study indicated that protegrins (porcine-derived peptides) can inactivate HIV-1 virions. Another study showed that indolicidin, a 13 amino acid peptide isolated from bovine neutrophils, was reproducibly virucidal against HIV-1 only at very high concentrations (333 μg/ml) of peptide. Certain structural and functional similarities exist between the loop motifs of α-defensins and peptides derived from HIV-1 gp41 that may be required for viral fusion and infectivity.

Vaginal and rectal subepithelial stromal tissues are densely populated with dendritic cells (DC), macrophages and T-cells that express both CD4 and the HIV-1 coreceptors, CXCR4 and CCR5. Mechanisms whereby H IV-1 journeys across the mucosal epithelia are not clear, but may directly involve the epithelial cells. Once the virus reaches the lamina propria, it can either directly infect macrophages or T-cells or adhere to or infect DC whose traffic to the regional lymph nodes conveys them into sites of vigorous viral replication. A recent report suggests that binding of HIV-1 to DC is mediated by the C-type lectin DC-SIGN, independent of CD4 or chemokine receptors. Thus, mucosal factors which modulate steps in this process could affect the probability of transmission of HIV-1 infection.

There is a clinical need for novel antiviral and antimicrobial agents that have low toxicity against mammalian cells. The present invention addresses this need.

Relevant Literature

Defensins are reviewed by Lehrer et al. (1992) *Ann. Rev. Immunol.* 11:105-128. Other endogenous antimicrobials are reviewed in Schonwetter et al. (1995) *Science* 267:1645-1648; Schroder (1999) *Cell Mol Life Sci.* 56:32-46 (1999); and Harwig et al. (1994) *FEBS Lett* 342:281-285.

Specific defensins are described in Tang et al. (1999) *Science* 286:498-502; Zimmermann et al. (1995) *Biochemistry* 34:13663-13671; Liu et al. (1997) *Genomics* 43:316-320; and Palfree & Shen (1994) GenBank U10267; Polley et al. GenBank AF238378 disclose the sequence of *Homo sapiens* chromosome 8p23 clone SCb-561b17.

Retrovirus infection and antiretroviral therapy are discussed in Wilson et al. (1995) *J. Infect Dis.* 172:88-96; Wong et al. *Science* 278:1291-1295; and Yang et al. (1999) *J. Virol.* 73, 4582-4589.

SUMMARY OF THE INVENTION

Methods and compositions are provided for the use of retrocyclin peptides. Retrocyclin peptides are small antimicrobial agents with potent activity against viruses, e.g.

enveloped viruses such as retroviruses; and bacteria. These circular peptides are nonhemolytic and generally exhibit little or no in vitro cytotoxicity. Retrocyclins are equally effective against growing and stationary phase bacteria, and they retain activity against some bacteria in physiological, and high salt concentrations. Studies indicate that retrocyclins are also capable of conferring immunity to human $CD4^+$ cells against infection by HIV-1 in vitro. In addition, other circular mini-defensins also find use as anti-viral agents, particularly against human retroviruses.

A pharmaceutical composition comprising retrocyclin or other circular mini-defensins as an active agent is administered to a patient suffering from a viral infection. Alternatively, a pharmaceutical composition comprising retrocyclin or other circular mini-defensins or is administered as a protective agent to a normal individual facing potential exposure to HIV or other viruses or to pathogenic microbes. Retrocyclin is also effective at killing a variety of microbial organisms, in vivo and in vitro. Retrocyclin may be administered alone, or in combination with other bacteriocidal agents, e.g. antibiotics and/or other antiviral agents, and antiviral agents as a cocktail of effective peptides, etc. Retrocyclin-mediated killing is also useful for modeling and screening novel antibiotics.

BRIEF DESCRIPTION OF THE DRAWINGS

FIG. 2. Sequence comparison of human and rhesus demidefensins. The translated sequences of rhesus demidefensin-1 mRNA (SEQ ID NO:17) and human retrocyclin (ESQ ID NO:5-97) mRNA are shown. Solid circles (●) indicate a stop codon in the corresponding cDNA. Vertical bars connect identical residues, and + signs connect similar residues. Residues represented in mature retrocyclin and RTD-molecules are boxed. The demidefensin-1 sequence (GenBank, AF184156) was derived from the monkey mRNA (not shown).

FIG. 3A-D. Structural characterization of retrocyclin. (A) CD spectrum demonstrating the similarity in structure between retrocyclin and RTD-1, both at 0.5 mg/ml in a 1:1 mixture of trifluoroethanol in phosphate buffered saline at pH 7.4. (B) shows a hypothetical model of retrocyclin made by templating its sequence on the backbone of a similar peptide from porcine neutrophils, Protegrin-1 (PDB accession code: 1 PG1). (D) (linked nonamers of SEQ ID NO:19) is a cartoon version of (B), wherein arginines are black, cysteines are grey and the other residues are identified by single letter code. (C) is a similar cartoon of rhesus RTD-1, (linked nonamers of SEQ ID NO:36 and 27), indicating the similarity in structure with retrocyclin.

FIG. 4. Effect of salt on antibacterial activity of circular minidefensins. Human retrocyclin and monkey RTD-1 were tested against our standard lab stains: *E. coli* ML-35p, *P. aeruginosa* MR 3007, *L. monocytogenes* EGD, and *S. aureus* 930918. The bars show MIC values±SEM values that resulted from 3-6 radial diffusion assays per organism and assay condition.

FIG. 5A-C. Anti-HIV-1 activity of retrocyclin. Two strains of HIV-1 and two types of human target cells were used. The IIIB strain is T-cell tropic (X4) and utilizes the CXCR4 co-receptor for entry; the JR-CSF strain is M-tropic (R5) and uses CCR5 for entry. PBMC signifies $CD4^+$-selected peripheral blood mononuclear cells. Results indicate p24 antigen concentration in pg/ml, as determined by quantitative ELISA assay at Day 9 timepoint. (A) Two concentrations of retrocyclin (2 µg/ml, 20 µg/ml), 20 µg/ml of the Rhesus circular defensin "RTD-1", and 20 µg/ml of a horseshoe crab-derived peptide "T140", reported to only prevent X4 infections, were tested in antiviral assays of against strain IIIB in H9 cells (n=2-6 per peptide; error bars indicate SEM). (B) To confirm our results with primary human cells, similar assays were performed utilizing IIIB virus and $CD4^+$ PBMC or (C) JR-CSF virus and $CD4^+$ PBMC. Peptides were not cytotoxic at indicated concentrations, measured by trypan blue exclusion. Average of duplicate experiments are reported for studies with PBMCs. Assay sensitivity=10 pg/ml.

FIGS. 9A and 9B are graphs depicting the activity of retrocyclin congeners against HIV-1 strains.

FIG. 10A is a schematics depicting the structure of retrocyclin (linked nonamers of SEQ ID NO:19): Retrocyclin 2 (linked nonamers of SEQ ID NO:19 and SEQ ID NO:74). Retrocyclin 3 (linked nonamers of SEQ ID NO:74) and RTD-1 (linked nonamers of SEQ ID NO:36 and SEQ ID NO:45). FIG. 10B is a schematic depicting the structure of a retrocyclin (linked nonamers of SEQ ID NO:52).

FIG. 11A-C compares the antiretroviral activity of retrocyclin and RC-101(20 µg/ml), by showing the p24 titers from day 9 $CD4^+$ PBMC (peripheral blood mononuclear cells) infected with HIV-1 strains IIIB or JR-CSF at the indicated MOI. RC-101 and retrocyclin were similarly effective in inhibiting HIV-1 replication at low MOI (A) and higher MOI (B).

FIG. 15A-15B depicts sequences of human, ape and monkey retrocyclins.

DESCRIPTION OF THE SPECIFIC EMBODIMENTS

Figure 1:
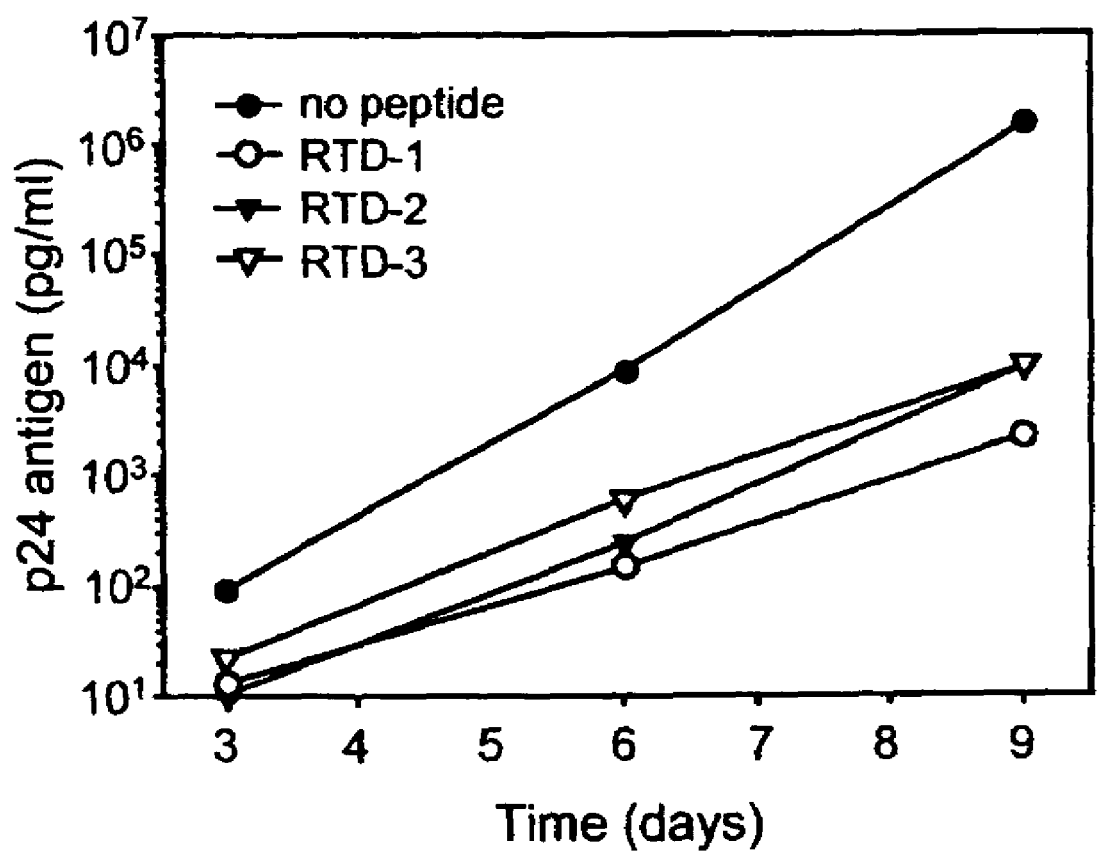
FIG. 1. Circular minidefensins reduce HIV-1 infection of H9 cells. HIV-I strain IIIB (MOI=$10^{-2}$) was incubated with $2.5\times10^5$ H9 cells in the presence or absence of 20 µg/ml RTD-1, RTD-2 or RTD-3. p24 antigen release was monitored by ELISA on days 3, 6, and 9. Assay sensitivity=10 pg/ml.

Novel compositions and methods are provided for the use of retrocyclins and retrocyclin analogs as therapeutic and/or prophylactic agents. The peptides are effective at killing a variety of microbial organisms by direct microbicidal activity, and protect against viral infection by a virus by preventing viral uptake and/or blocking an early step in viral replication. Retrocyclin(s) are administered alone or in combination with other active agents to a patient suffering from an infection in a dose and for a period of time sufficient to reduce the patient population of pathogenic microbes or viruses. Alternatively, a pharmaceutical composition comprising retrocyclin or other circular mini-defensins or is administered as a protective agent to a normal individual facing potential exposure to HIV viruses or pathogenic microbes. In addition, other circular mini-defensins, including RTD-1, RTD-2 and RTD-3 and variants of retrocyclin find use as anti-viral agents.

Specific treatments of interest include, without limitation: using retrocyclin (e.g., RC-101) or a retrocyclin analog to prevent or treat infection, for example by an enveloped virus, including enveloped retroviruses, more specifically by HIV-1, HIV-2 and related retroviruses that cause Acquired Immunodeficiency Syndrome (AIDS); aerosol administration to the lungs of patients with cystic fibrosis to combat infection or forestall the emergence of resistance to other inhaled antibiotics; instillation into the urinary bladder of patients with indwelling catheters to prevent infection; application to the skin of patients with serious burns; opthalmic instillation, directly or in ophthalmic solutions, to treat or prevent infection; intravaginal application to treat bacterial vaginosis and/or prevent sexually transmitted disease such as HIV infection. The retrocyclins also may find use in the treatment of plant-pathogenic pseudomonads, in agricultural applications designed to prevent disease in and spoilage of food crops. The retrocyclins may be administered alone or in conjunction with other antiviral therapy.

The peptide form of retrocyclins provides a basis for further therapeutic development, by modification of the polypeptide structure to yield modified forms having altered biological and chemical properties. The native or modified forms are formulated in a physiologically acceptable carrier for therapeutic uses, or are otherwise used as an antimicrobial agent.

Retrocyclin Compositions

For use in the subject methods, a naturally occurring or synthetic retrocyclin may be used. As used herein, retrocyclins are cyclic polypeptides comprising the amino acid sequence:

$X_1 X_2 X_3 X_4 X_5 X_6 X_7 X_8 X_9 X_{10} X_{11} X_{12} X_{13} X_{14} X_{15} X_{16} X_{17} X_{18}$ wherein X1 and X18 are linked through a peptide bond, disulfide crosslinks are formed between at least one of: $X_3$ and $X_{16}$; $X_5$ and $X_{14}$, and $X_7$ and $X_{12}$, usually between at least two of such pairs, and preferably between the three pairs of amino acids, with the proviso that when such a crosslink is present, the crosslinked amino acids are both cysteines;

at least about three of amino acids $X_1$ to $X_{18}$ are arginine or lysine, and the number of arginine or lysine residues may be four or more, five or more, or six or more. Preferred residues for arginine or lysine are $X_4$, $X_9$, $X_8$, $X_{13}$, and $X_{18}$;

$X_2$, $X_6$, $X_{11}$, $X_{15}$ are preferably aliphatic amino acids, e.g. isoleucine, leucine, valine, phenylalanine, and alanine;

$X_1$, $X_8$, $X_{10}$ and $X_{17}$ are preferably glycine or alanine, usually glycine.

Retrocyclins are octadecapeptides that contain two linked nonapeptides that may be identical or different. A consensus nonapeptide has the sequence shown below, where the bolded and underlined residues are invariant among the primate sequences identified herein. Substitutions found in the nonapeptide regions of other circular minidefensin precursors are shown below the consensus nonapeptide.

| Residue No | 1 3 5 7 9 | |
|---|---|---|
| Consensus nonapeptide | RCICGRGIC | (SEQ ID NO: 19) |
| Variant | L RLRV | (SEQ ID NO: 126) |
| Variant | T F | (SEQ ID NO: 36) |
| Variant | V | (SEQ ID NO: 23) |
| Variant | R | (SEQ ID NO: 74) |

From the consensus peptide and these variants, one can generate unique nonapeptide sequences (herein termed n1, n2 . . . etc.). Thus, n1 could be linked to itself or any of the other nonapeptides (n1:n1, n1:n2, n1:n3 . . . etc.), to generate unique octadecapeptides. To continue the process, n2 could be linked to itself or to any other nonapeptide except n1, to generate additional unique octadecapeptides, and so forth.

Two naturally occurring human nonapeptide sequences are RCICGRGIC; (SEQ ID NO:19); and RCICGRRIC. (SEQ ID NO:74). The set of nonapeptides derived from these sequences and variants (which are also provided in the sequence listing as SEQ ID NO:19-64; and 74-119) is as follows:

| SEQ ID NO: | 1 2 3 4 5 6 7 8 9 | mod'n* | SEQ ID NO: NP# | 1 2 3 4 5 6 7 8 9 | modification* |
|---|---|---|---|---|---|
| 19 | R C I C G R G I C | — | 42 | R C I C G L G F C | L6, F8 |
| 20 | R C L C G R G I C | L3 | 43 | R C I C G L G V C | L6, V8 |
| 21 | R C I C R R G I C | R5 | 44 | R C L C R L G I C | L3, R5, L6 |
| 22 | R C I C T R G I C | T5 | 45 | R C L C R R G V C | L3, R5, V8 |
| 23 | R C I C V R G I C | V5 | 46 | R C L C R R G F C | L3, R5, F8 |
| 24 | R C I C G L G I C | L6 | 47 | R C L C T L G I C | L3, T5, L6 |
| 25 | R C I C G R G V C | V8 | 48 | R C L C G R G V C | L3, T5, V8 |
| 26 | R C I C G R G F C | F8 | 49 | R C L C T R G F C | L3, T5, F8 |
| 27 | R C L C R R G V C | L3, R5 | 50 | R C L C V L G I C | L3, V5, L6 |
| 28 | R C L C T R G I C | L3, T5 | 51 | R C L C V R G V C | L3, V5, V8 |
| 29 | R C L C V R G I C | L3, V5 | 52 | R C I C G R G I C | L3, V5, F8 |
| 30 | R C L C G L G V C | L3, L6 | 53 | R C I C R L G V C | R5, L6, V8 |
| 31 | R C L C G R G V C | L3, V8 | 54 | R C I C R L G F C | R5, L6, F8 |
| 32 | R C L C G R G F C | L3, F8 | 55 | R C I C T L G V C | T5, L6, V8 |
| 33 | R C I C R R G V C | R5, V8 | 56 | R C I C T L G F C | T5, L6, F8 |
| 34 | R C I C R R G F C | R5, F8 | 57 | R C I C V L G V C | V5, L6, V8 |
| 35 | R C I C T R G V C | T5, V8 | 58 | R C I C V L G F C | V5, L6, F8 |
| 36 | R C I C T R G F C | T5, F8 | 59 | R C L C G L G V C | L3, R5, L6, V8 |
| 37 | R C I C T L G I C | T5, L6 | 60 | R C L C G L G I C | L3, R5, L6, F8 |
| 38 | R C I C V L G F C | V5, L6 | 61 | R C L C T L G V C | L3, T5, L6, V8 |
| 39 | R C I C R L G I C | R5, L6 | 62 | R C L C T L G I C | L3, T5, L6, F8 |
| 40 | R C I C V R G V C | V5, V8 | 63 | R C L C V L G V C | L3, V5, L6, V8 |
| 41 | R C I C G R G F C | V5, F8 | 64 | R C L C V L G I C | L3, V5, L6, F8 |
| 74 | R C I C G R R I C | — | 97 | R C I C G L R F C | L6, F8 |
| 75 | R C L C G R R I C | L3 | 98 | R C I C G L R V C | L6, V8 |
| 76 | R C I C R R R I C | R5 | 99 | R C L C R L R I C | L3, R5, L6 |
| 77 | R C I C T R R I C | T5 | 100 | R C L C R R R V C | L3, R5, V8 |
| 78 | R C I C V R R I C | V5 | 101 | R C L C R R R F C | L3, R5, F8 |
| 79 | R C I C G L R I C | L6 | 102 | R C L C T L R I C | L3, T5, L6 |
| 80 | R C I C G R R V C | V8 | 103 | R C L C G R R V C | L3, T5, V8 |
| 81 | R C I C G R R F C | F8 | 104 | R C L C T R R F C | L3, T5, F8 |
| 82 | R C L C R R R V C | L3, R5 | 105 | R C L C V L R I C | L3, V5, L6 |
| 83 | R C L C T R R I C | L3, T5 | 106 | R C L C V R R V C | L3, V5, V8 |
| 84 | R C L C V R R I C | L3, V5 | 107 | R C I C G R R I C | L3, V5, F8 |
| 85 | R C L C G L R V C | L3, L6 | 108 | R C I C R L R V C | R5, L6, V8 |

| SEQ ID NO: | 1 2 3 4 5 6 7 8 9 | mod'n* | SEQ ID NO: NP# | 1 2 3 4 5 6 7 8 9 | modification* |
|---|---|---|---|---|---|
| 86 | R C L C G R R V C | L3, V8 | 109 | R C I C R L R F C | R5, L6, F8 |
| 87 | R C L C G R R F C | L3, F8 | 110 | R C I C T L R V C | T5, L6, V8 |
| 88 | R C I C R R R V C | R5, V8 | 111 | R C I C T L R F C | T5, L6, F8 |
| 89 | R C I C R R R F C | R5, F8 | 112 | R C I C V L R V C | V5, L6, V8 |
| 90 | R C I C T R R V C | T5, V8 | 113 | R C I C V L R F C | V5, L6, F8 |
| 91 | R C I C T R R F C | T5, F8 | 114 | R C L C G L R V C | L3, R5, L6, V8 |
| 92 | R C I C T L R I C | T5, L6 | 115 | R C L C G L R I C | L3, R5, L6, F8 |
| 93 | R C I C V L R F C | V5, L6 | 116 | R C L C T L R V C | L3, T5, L6, V8 |
| 94 | R C I C R L R I C | R5, L6 | 117 | R C L C T L R I C | L3, T5, L6, F8 |
| 95 | R C I C V R R V C | V5, V8 | 118 | R C L C V L R V C | L3, V5, L6, V8 |
| 96 | R C I C G R R F C | V5, F8 | 119 | R C L C V L R I C | L3, V5, L6, F8 |

*residue modifications are shown in this column.
NP# is a reference number for the nonamers.

Retrocyclins of interest include cyclic peptides derived from the peptide sequence set forth in SEQ ID NO. 12, in particular a circular homodimer comprising a dimer of the amino acid sequence SEQ ID NO:12, aa 48-56. This retrocyclin has the structure (SEQ ID NO:1; RC100):

G   I   C   R   C   I   C   G   R   G   I   C   R   C   I   C   G   R
$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $X_{17}$ $X_{18}$

Wherein $X_1$ and $X_{18}$ are joined by a peptide bond, $X_2$ and $X_{11}$; $X_4$ and $X_9$, and $X_{13}$ and $X_{18}$ are disulfide bonded.

Another retrocyclin of interest is the synthetic analog (SEQ ID NO:2, RC101)

G   I   C   R   C   I   C   G   K   G   I   C   R   C   I   C   G   R
$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $X_{17}$ $X_{18}$ wherein $X_1$ and $X_{18}$ are joined by a peptide bond, $X_2$ and $X_{11}$; $X_4$ and $X_9$, and $X_{13}$ and $X_{18}$ are disulfide bonded. Other synthetic analogs, or congeners, of retrocyclin are set forth in SEQ ID NO:3-SEQ ID NO:10.

Some retrocyclins comprising lysine residues or analogs thereof are of particular interest. Lysine analogs include lysine, diaminohexynoic acid, N-epsilon-methyllysine, N-alpha-methyllysine, diaminopimelic acid, 5-aminopentanoic acid, and 7-aminoheptanoic acid and their D-amino acid counterparts. Such sequences are modified from those set forth in SEQ ID NO:19-64; and SEQ ID NO:94-119 by replacing at least one arginine residue with a lysine residue, and in a nonamer, may replace 1 or 2 arginines with lysines. Of particular interest are retrocyclins where at least one of the nonamers set forth in SEQ ID NO:19-64; and SEQ ID NO:94-119 comprises lysine or lysine analog at residue 6.

In some instances, such nonamers have the consensus sequence:

R   $^R/_K$   I   C   G   $^R/_K$   $^R/K/_G$   I   C      (SEQ ID NO: 136)
$X_1$ $X_2$ $X_3$ $X_4$ $X_5$ $X_6$ $X_7$ $X_8$ $X_9$ where the retrocyclin molecule itself comprises two independently selected nonamers. Such sequences are desirably reduced in hemagglutination relative to the arginine containing sequence. Among the specific lysine containing retrocyclins of interests are the following:

| | Identifier | Alternative Name | Sequence (linear) |
|---|---|---|---|
| SEQ ID NO:126 | RC114 | RC101/103 hybrid | GICRCICGK GICRCYCGR |
| SEQ ID NO:127 | RC119 | R→K Retrocyclin-1 | GICKCICGK GICKCICGR |

-continued

| Identifier | Alternative Name | Sequence (linear) |
|---|---|---|
| SEQ ID NO:128 RC123A | Retrocyclin 2A | GICRCICGK RICRCICGR |
| SEQ ID NO:129 RC123B | Retrocyclin 2B | GICRCICGK KICRCICGR |
| SEQ ID NO:130 RC123C | Retrocyclin 2C | GICRCICGR KICRCICGR |
| SEQ ID NO:131 RC123D | Retrocyclin 2D | GICRCICGR RICKCICGR |
| SEQ ID NO:132 RC123E | Retrocyclin 2E | GICKCICGR RICRCICGR |
| SEQ ID NO:133 RC123F | Retrocyclin 2F | GICRCICGR RICRCICGK |

Also of interest are the sequences SEQ ID NO:134: GVCRC ICGRG VCRCI CRR; and SEQ ID NO:135: GVCRC ICGRG VCRCI CGR. Retrocyclins of this type are comprised, or consist, of two linked nonamers independently selected from SEQ ID NO:25 and SEQ ID NO:33.

The sequence of the retrocyclin polypeptides may be altered in various ways known in the art to generate targeted changes in sequence. The polypeptide will usually be substantially similar to the sequences provided herein, i.e. will differ by one amino acid, and may differ by two amino acids. The sequence changes may be substitutions, insertions or deletions.

The protein may be joined to a wide variety of other oligopeptides or proteins for a variety of purposes. By providing for expression of the subject peptides, various post-translational modifications may be achieved. For example, by employing the appropriate coding sequences, one may provide farnesylation or prenylation. In this situation, the peptide will be bound to a lipid group at a terminus, so as to be able to be bound to a lipid membrane, such as a liposome.

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein. Genetic sequences encoding demidefensins are provided herein, e.g. SEQ ID NO:4, 7 and 9.

In one embodiment of the invention, the antimicrobial peptide consists essentially of a polypeptide sequence set forth in any one of SEQ ID NO:1-SEQ ID NO:10. By "consisting essentially of" in the context of a polypeptide described herein, it is meant that the polypeptide is composed of the sequence set forth in the seqlist, which sequence may be flanked by one or more amino acid or other residues that do not materially affect the basic characteristic(s) of the polypeptide.

For some purposes of the invention, for example in the treatment and/or prevention of HIV infection, the active agent may be any one of the circular minidefensins, e.g. human retrocyclins, RTD-1, RTD-2 and RTD-3. Cyclic minidefensins resemble protegrins, antimicrobial β-sheet peptides. RTD-1 is derived from *Macacca mulatta*, and is a heterodimer containing tandem nonapeptide elements derived from the mature peptides set forth in SEQ ID NO:15 and SEQ ID NO:17. RTD-2 is a homodimer containing, in tandem, two identical nonapeptide elements derived from the mature peptide set forth in SEQ ID NO:17. RTD-3 is a homodimer containing, in tandem, two identical nonapeptide elements derived from the mature peptide set forth in SEQ ID NO:15.

All three RTD's are circular molecules with 18 residues and three intramolecular disulfide bonds. Each RTD is formed by in vivo processing that trims and splices two precursor peptides ("demidefensins"), each of which contributes nine residues (including 3 cysteines) to the mature cyclic peptide. The 18 RTD-1 residues derive from two different demidefensin precursors, RTD-2 and -3 have tandem 9 residue repeats derived from a single demidefensin precursor.

Retrocyclin Coding Sequences

The invention includes nucleic acids having a sequence set forth in SEQ ID NO:11, 120 or 122; nucleic acids that hybridize under stringent conditions, particularly conditions of high stringency, to the sequence set forth in SEQ ID NO: SEQ ID NO:11, 120 or 122; genes corresponding to the provided nucleic acids; sequences encoding retrocyclins; and fragments and derivatives thereof. Other nucleic acid compositions contemplated by and within the scope of the present invention will be readily apparent to one of ordinary skill in the art when provided with the disclosure here. Genetic sequences of particular interest include primate sequences, e.g. human, chimpanzee, bonobo, orangutan, gorilla, etc.

Retrocyclin coding sequences can be generated by methods known in the art, e.g. by in vitro synthesis, recombinant methods, etc. to provide a coding sequence to corresponds to a linear retrocyclin polypeptide that could serve as an intermediate in the production of the cyclic retrocyclin molecule. Using the known genetic code, one can produce a suitable coding sequence. For example, the circular polypeptide of retrocyclin (SEQ ID NO: 1) is encoded by the sequence (SEQ ID NO:18) AGG TGC ATT TGC GGA AGA GGA ATT TGC AGG TGC ATT TGC GGA AGA GGA ATT TGC, but since the peptide is circular, it is somewhat arbitrary which codon is selected to be first, allowing this to be based on other criteria, e.g. relative efficiency in purification or cyclization of the predicted product. The polypeptide set forth in SEQ ID NO:2 is encoded by a similar sequence, wherein one of the arginine codons (AGA) is substituted with a lysine codon (AAA or AAG).

The nucleic acids of the invention include nucleic acids having sequence similarity or sequence identity to SEQ ID NO: SEQ ID NO:11, 18, 120 or 122. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to SEQ ID NO: SEQ ID NO:11, 18, 120 or 122 under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, fish, yeast, nematodes, etc.

In one embodiment, hybridization is performed using at least 18 contiguous nucleotides (nt) of SEQ ID NO:1 and SEQ ID NO:18, or a DNA encoding the polypeptide of SEQ ID NO:1-10, 19-64, or 74-119. Such a probe will preferentially hybridize with a nucleic acid comprising the complementary sequence, allowing the identification and retrieval of the nucleic acids that uniquely hybridize to the selected probe. Probes of more than 18 nt can be used, e.g., probes of from about 18 nt to about 25, 50, 100 or 250 nt, but 18 nt usually represents sufficient sequence for unique identification.

Nucleic acids of the invention also include naturally occurring variants of the nucleotide sequences (e.g., degenerate variants, allelic variants, etc.). Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25-30% base pair (bp) mismatches relative to the selected nucleic acid probe. In general, allelic variants contain 15-25% bp mismatches, and can contain as little as even 5-15%, or 2-5%, or 1-2% bp mismatches, as well as a single bp mismatch.

The invention also encompasses homologs corresponding to the nucleic acids of SEQ ID NO:5, where the source of homologous genes can be any mammalian species, e.g., primate species, particularly human; rodents, such as rats; canines, felines, bovines, ovines, equines, fish, yeast, nematodes, etc. Between mammalian species, e.g., human and mouse, homologs generally have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as gapped BLAST, described in Altschul et al. Nucl. Acids Res. (1997) 25:3389-3402.

The subject nucleic acids can be cDNAs or genomic DNAs, as well as fragments thereof, particularly fragments that encode a biologically active polypeptide and/or are useful in the methods disclosed herein. The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' and 3' end of the transcribed region. The genomic DNA can be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue, stage-specific, or disease-state specific expression.

The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the invention comprise at least 18, about 50, about 100, to about 200 contiguous nt selected from the nucleic acid sequence as shown in SEQ ID NO: SEQ ID NO:11, 120 or 122. For the most part, fragments will be of at least 18 nt, usually at least 25 nt, and up to at least about 50 contiguous nt in length or more.

Probes specific to the nucleic acid of the invention can be generated using the nucleic acid sequence disclosed in SEQ ID NO:11, or a DNA encoding the polypeptide of SEQ ID NO:1-10. The probes are preferably at least about 18 nt, 25 nt or more of the corresponding contiguous sequence. The probes can be synthesized chemically or can be generated from longer nucleic acids using restriction enzymes. The probes can be labeled, for example, with a radioactive, biotinylated, or fluorescent tag. Preferably, probes are designed based upon an identifying sequence of one of the provided sequences. More preferably, probes are designed based on a contiguous sequence of one of the subject nucleic acids that remain unmasked following application of a masking program for masking low complexity (e.g., BLASTX) to the sequence, i.e., one would select an unmasked region, as indicated by the nucleic acids outside the poly-n stretches of the masked sequence produced by the masking program.

The nucleic acids of the invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

Retrocyclin encoding nucleic acids can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Expression vectors may be used to introduce a retrocyclin coding sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or retrocyclin peptide may be introduced into tissues or host cells by any number of routes, including viral infection, microinjection, or fusion of vesicles. Jet injection may also be used for intramuscular administration, as described by Furth et al. (1992) *Anal Biochem* 205:365-368. The DNA may be coated onto gold microparticles, and delivered intradermally by a particle bombardment device, or "gene gun" as described in the literature (see, for example, Tang et al. (1992) *Nature* 356:152-154), where gold microprojectiles are coated with the stresscopin or DNA, then bombarded into skin cells.

Methods of Use

Formulations of retrocyclins are administered to a host suffering from an ongoing bacterial or viral infection or who faces exposure to a bacterial or viral infection. Antiviral compositions may also utilize other circular mini-defensins, e.g. RC-101, RTD-1, -2, and -3, alone or in combination with retrocyclin. Administration may be topical, localized or systemic, depending on the specific microorganism. Generally the dosage will be sufficient to decrease the microbial or viral population by at least about 50%, usually by at least 1 log, and may be by 2 or more logs. The compounds of the present invention are administered at a dosage that reduces the pathogen population while minimizing any side-effects. It is contemplated that the composition will be obtained and used under the guidance of a physician for in vivo use. Retrocyclins are particularly useful for killing *Listeria monocytogenes* and *Escherichia coli*, and for preventing infection by certain viruses, particularly enveloped retroviruses, e.g. enveloped retroviruses such as HIV-1, HIV-2, FIV, and the like.

Retrocylins are also useful for in vitro formulations to kill microbes, particularly where one does not wish to introduce quantities of conventional antibiotics. For example, retrocyclins may be added to animal and/or human food preparations, or to blood products intended for transfusion to reduce the risk of consequent bacterial or viral infection. This may be of particular interest since a common route of infection of *E. coli* and *L. monocytogenes* is the gastrointestinal tract. Retrocyclins may be included as an additive for in vitro cultures of cells, to prevent the overgrowth of microbes in tissue culture.

The susceptibility of a particular microbe or virus to killing or inhibition by retrocyclins may be determined by in vitro testing, as detailed in the experimental section. Typically a culture of the microbe is combined with retrocyclins at varying concentrations for a period of time sufficient to allow the protein to act, usually ranging from about one hour to one day. The viable microbes are then counted, and the level of killing determined. Two stage radial diffusion assay is a convenient alternative to determining the MIC or minimum inhibitory concentration of an antimicrobial agent.

Viral pathogens of interest include retroviral pathogens, e.g. HIV-1; HIV-2, HTLV, FIV, SIV, etc. Microbes of interest, but not limited to the following, include: *Citrobacter* sp.; *Enterobacter* sp.; *Escherichia* sp., e.g. *E. coli*; *Klebsiella* sp.; *Morganella* sp.; *Proteus* sp.; *Providencia* sp.; *Salmonella* sp., e.g. *S. typhi, S. typhimurium; Serratia* sp.; *Shigella* sp.; *Pseudomonas* sp., e.g. *P. aeruginosa; Yersinia* sp., e.g. *Y. pestis, Y. pseudotuberculosis, Y enterocolitica; Franciscella* sp.; *Pasturella* sp.; *Vibrio* sp., e.g. *V. cholerae, V. parahemolyticus; Campylobacter* sp., e.g. *C. jejuni; Haemophilus* sp., e.g. *H. influenzae, H. ducreyi; Bordetella* sp., e.g. *B. pertussis, B. bronchiseptica, B. parapertussis; Brucella* sp., *Neisseria* sp., e.g. *N. gonorrhoeae, N. meningitidis*, etc. Other bacteria of interest include *Legionella* sp., e.g. *L. pneumophila; Listeria* sp., e.g. *L. monocytogenes; Staphylococcus* sp., e.g. *S. aureus Mycoplasma* sp., e.g. *M. hominis, M. pneumoniae; Mycobacterium* sp., e.g. *M. tuberculo-* sis, *M. leprae*; *Treponema* sp., e.g. *T. pallidum*; *Borrelia* sp., e.g. *B. burgdorferi*; *Leptospirae* sp.; *Rickettsia* sp., e.g. *R. rickettsii*, *R. typhi*; *Chlamydia* sp., e.g. *C. trachomatis*, *C. pneumoniae*, *C. psittaci*; *Helicobacter* sp., e.g. *H. pylori*, etc.

Various methods for administration may be employed. For the prevention of HIV infection, administration to mucosal surfaces is of particular interest, e.g. vaginal, rectal, etc. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific retrocyclin or demi-defensin to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, lotions, and aerosols. As such, administration of the compounds can be achieved in various ways, including oral, vaginal, buccal, rectal, parenteral, intraperitoneal, intradermal, transdermal, intratracheal, etc., administration. The retrocyclins may be systemic after administration or may be localized by the use of an implant or other formulation that acts to retain the active dose at the site of implantation.

The compounds of the present invention can be administered alone, in combination with each other, or they can be used in combination with other known compounds (e.g., perforin, anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral, vaginal or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing retrocyclins is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For preparing the liposomes, the procedure described by Kato et al. (1991) *J. Biol. Chem.* 266:3361 may be used. Briefly, the lipids and lumen composition containing peptides are combined in an appropriate aqueous medium, conveniently a saline medium where the total solids will be in the range of about 1-10 weight percent. After intense agitation for short periods of time, from about 5-60 sec., the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Formulations with Other Active Agents

For use in the subject methods, retrocyclins may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Cytokines may also be included in a retrocyclin formulation, e.g. interferon γ, tumor necrosis factor α, interleukin 12, etc.

Antiviral agents, e.g. acyclovir, gancyclovir, etc., and other circular mini-defensins (theta defensins) may also be included in retrocyclin formulations.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Sexual and mother-to-neonate (vertical) transmission through mucosal surfaces have been the most common routes of HIV-1 spread throughout the world. Although much attention has been focused on vaccine development for HIV-1, progress has been slow and there is an urgent need to find alternative approaches to prevent infections caused by HIV-1. Self-applied prophylactic agents to prevent mucosal, particularly vaginal or rectal, transmission of HIV-1 have the advantage of empowering vulnerable receptive partners to take effective measures for their own protection. In a search for novel compounds active against HIV-1, it was discovered that certain antimicrobial peptides, the circular minidefensins from the rhesus macaque, could inhibit HIV-1 replication. This prompted an investigation as to whether humans produce circular minidefensins. Although there is no evidence that these proteins are produced in humans, clearly some primate ancestors once made retrocyclin, because it continues to exist in contemporary humans as an expressed pseudogene.

After discovering an mRNA molecule in human bone marrow that was highly homologous to rhesus circular minidefensins (88.9% identity at the nucleotide level), solid phase peptide synthesis was used to create the peptide ("retrocyclin") whose sequence it encoded. Retrocyclin belongs to the θ defensin subfamily (also referred to as cyclic minidefensins). The antimicrobial properties of retrocyclin resemble those of rhesus θ-defensins. However, retrocyclin is highly effective in preventing the infection of $CD4^+$ cells by X4 and R5 strains of HIV-1 in vitro.

Example 1

Circular Minidefensins can Block HIV-1 Replication

It is shown herein that retrocyclin, a circular minidefensin, is potently active against both X4 and R5 strains of HIV-1. The initial descriptions of circular minidefensins came from studies of *Macaca mulatta*, the rhesus macaque monkey. The first such peptide, RTD-1, was called a rhesus theta defensin (RTD), which are also referred to as "cyclic minidefensins". The peptides encoded by the mRNA precursors may be referred to as "demidefensins".

RTD-2 and RTD-3, which was isolated from the bone marrow of rhesus monkeys, are circular, 18 amino acid peptides that contained three intramolecular disulfide bonds. They are similar to RTD-1, the circular (θ) defensin previously described by Tang et al., However, whereas the 18 residues of RTD-1 represent spliced 9 amino acid fragments derived from two different minidefensin precursors, RTD-2 and -3 comprise tandem 9 residue repeats derived from a single RTD-1 precursor. Thus, circular minidefensins are processed by a novel post-translational system that can generates a degree of effector molecule diversity without requiring commensurate genome expansion.

Retrocyclin and the other circular minidefensins we prepared were synthesized, folded, circularized and purified essentially. The antiviral activities of RTD-1, RTD-2 and RTD-3 are shown in FIG. 1. For these studies, the X4 HIV-1 strain IIIB was utilized.

Immortalized $CD4^+$ H9 cells, which are permissive for infection with this strain, were maintained in RPMI supplemented with 10% heat-inactivated fetal calf serum (FCS), 10 mM HEPES, 2 mM glutamine, 100 U of penicillin/ml, and 10 μg of streptomycin/ml (R10 media). Cells ($2.5 \times 10^5/100$ μl) were incubated with virus (multiplicity of infection (MOI)=$10^{-2}$) in the presence or absence of 20 μg/ml RTD-1, RTD-2 or RTD-3 for 3 hrs at 37° C./5% $CO_2$. The cells were washed in R10 media, seeded in 48-well tissue culture plates in 1 ml R10 media, and incubated at 37° C./5% $CO_2$ for 9 days. Aliquots of cell supernatant were removed at the specified time points and analyzed by a sensitive ELISA (DuPont NEN) that quantitates p24 antigen of HIV-1. The three circular rhesus minidefensins were similarly active, inhibiting HIV-1 by 100-1000 fold by 9 days post-inoculation (note the logarithmic scale).

Example 2

Identification and Structural Characterization of Retrocyclin

To search for human circular minidefensins, two primers were prepared based on the monkey minidefensin cDNA sequences (GenBank AF 184156, 184157, 184158). When PCR was performed on Marathon-Ready human bone marrow cDNA (Clontech, Palo Alto, Calif.), a 264 bp amplified product was recovered. To obtain its 3' and 5' side sequences, Marathon-Ready human bone marrow cDNA was amplified using a 3'-RACE kit (Gibco BRL, Gaithersburg, Md.) and 5'-RACE kit from Boehringer Mannheim (Indianapolis, Ind.).

At the nucleotide level, this product (retrocyclin) was ~89% identical to the demidefensin precursors of rhesus RTD-1 (called precursors 1a and 1b). FIG. 2 shows the peptide sequences of demidefensin 1 and preproretrocyclin. Residues incorporated into the mature circular minidefensins are boxed and all stop codons are represented by solid circles. Although a stop codon within the human transcript's signal sequence should abort translation, the otherwise high conservation of rhesus and human mRNA's suggested that humans may have acquired this mutation relatively recently in primate evolution.

Three orangutan retrocyclin genes have been sequences. One of these climes has the silencing stop codon in the signal sequence and therefore resembles human retrocyclin. The other two orangutan genes appear to be functional, i.e. when translated they would produce demi-defensins, the precursors of cyclic minidefensins.

Human leukocytes were examined for the presence of retrocyclin or similar peptides, but, as expected from the presence of the signal sequence's stop codon, none was found. Thus synthetic retrocyclin represents the circular minidefensin that would have formed: a) if the signal sequence mutation were absent, and b) if the precursor underwent homologous pairing so that its boxed residues (see FIG. 2) formed both halves of the circular molecule.

In phylogenetic studies of the retrocyclin demidefensin gene, the premature stop codon in the signal sequence was found to be present in four anthropoid species (humans, gorillas, chimpanzees, pygmy chimpanzees) and not present in the genes of a fifth (orangutangs). The demidefensin gene also appears intact (i.e., no premature stop codon) in the two catarrhine (Old World Monkey) species examined to date, *Macaca mulatta* and *Macaca nemestrina*. These findings suggest that native retrocyclin peptides were last produced by a primate ancestor of humans and other anthropoids that lived between 6 and 15 million years ago (mya). This is between the time that orangutang and human lineage diverged (15 mya) and before the divergence of the chimpanzee and human lineages (6 mya). These ongoing studies of primate phylogeny may yield sequence information about additional cyclic minidefensins whose native counterparts are extinct.

Retrocyclin synthesis. Peptides were synthesized at a 0.25 mmol scale with a Perkin-Elmer ABI 431A Synthesizer, using pre-derivatized polyethylene glycol polystyrene arginine resin (PerSeptive Biosystems, Framingham, Mass.), FastMoc™ chemistry, and double coupling for all residues. The crude peptide was reduced under nitrogen, for 15 hours at 50° C. with excess dithiothreitol in 6 M guanidine.HCl, 0.2 M Tris.HCl and 0.2 mM EDTA (pH 8.2). The reaction was stopped with glacial acetic acid (final concentration, 5%) and the reduced peptide was stored under nitrogen until purified by RP-HPLC. After this step, the peptide appeared homogeneous and its mass (1942.5, by MALDI-TOF MS) agreed well with its theoretical mass. The reduced peptide (0.1 mg/ml) was oxidized, cyclized and purified essentially as described by Tang et al., supra. The MALDI-TOF MS mass of retrocyclin (1918.5 Da) agreed well with its expected mass. CD spectra were obtained at 25° C. from an AVIV 62DS spectropolarimeter (AVIV, Lakewood, N.J.).

RTD-1 and retrocyclin have very similar CD spectra, with largely β-sheet structures stabilized by disulfide linkages and connected by turns (FIG. 3A). Antimicrobial peptides with similar spectra include tachyplesins, protegrins, and circularized defensins. FIG. 3B, a backbone ribbon model of retrocyclin, was made by templating its sequence on the structure of protegrin PG-1 and cyclizing it. The resulting structure was annealed by molecular dynamics and energy minimized. FIG. 3D is a cartoon version of FIG. 3B, designed primarily to show the placement of the cysteine and arginine molecules. FIG. 3C is a similar cartoon of rhesus RTD-1.

Retrocyclin is a selectively salt-insensitive antibacterial peptide. The effects of NaCl on the antimicrobial activity of retrocyclin and RTD-1, from two-stage radial diffusion assays, are compared in FIG. 4. The peptides showed very similar behavior. Under low salt conditions, both peptides were highly effective (minimal inhibitory concentration (MIC)<3 μg/ml) against all four test organisms: *Pseudomonas aeruginosa, Escherichia coli, Listeria monocytogenes* and *Staphylococcus aureus*. Their strong activity against *E. coli* and *L. monocytogenes* persisted in physiological (100 mM) NaCl, and even hypersalinity (175 mM NaCl) was only modestly inhibitory. In contrast, neither peptide was effective (MIC >50 μg/ml) against *S. aureus* or *P. aeruginosa* in physiological or high salt concentrations. Retrocyclin's activity is likely to be preserved in the ionic concentration of the vaginal mucosa.

Retrocyclin potently inhibits HIV-1 replication of R5 and X4 viruses. The antiretroviral properties of retrocyclin are shown in FIG. 5. Either HIV-1-permissive H9 cells were used as targets, or primary $CD4^+$ lymphocytes from HIV-1-seronegative donors generated from freshly purified peripheral blood mononuclear cells (PBMC) stimulated with a CD3-CD8 bispecific monoclonal antibody. After approximately 7 days, when 98% of these cells co-expressed CD3 and CD4, they were infected with HIV-1 with or without retrocyclin or other test peptide. These cells were maintained in RPMI containing 10% FCS supplemented with 2 mM glutamine, 100 U of penicillin/ml, 10 μg of streptomycin/ml, and 50 U of interleukin 2/ml (R10-50 media).

Retrocyclin (10-20 μg/ml) afforded complete suppression of viral replication to CD4+-selected PBMC challenged with two different strains of HIV-1: IIIB (an X4 strain) and JR-CSF (an R5 strain), or H9 human T cells challenged with IIIB. Note that the concentration of p24 antigen is presented on a log-scale and that the rhesus circular minidefensins, RTD-1 (FIG. 5 and FIG. 1) and RTD-2 and RTD-3 were protective to a lesser extent than retrocyclin. Additionally, the antiretroviral activities of T140 (20 μg/ml; FIG. 5) and T22, analogs of polyphemusins from horseshoe crabs that were previously shown to protect against X4, but not R5, infections, were confirmed in the present study. Microbicides, such as retrocyclin, that target both X4 and R5 viruses be more effective than agents that preferentially inhibit viruses of a single tropism.

Figure 6:
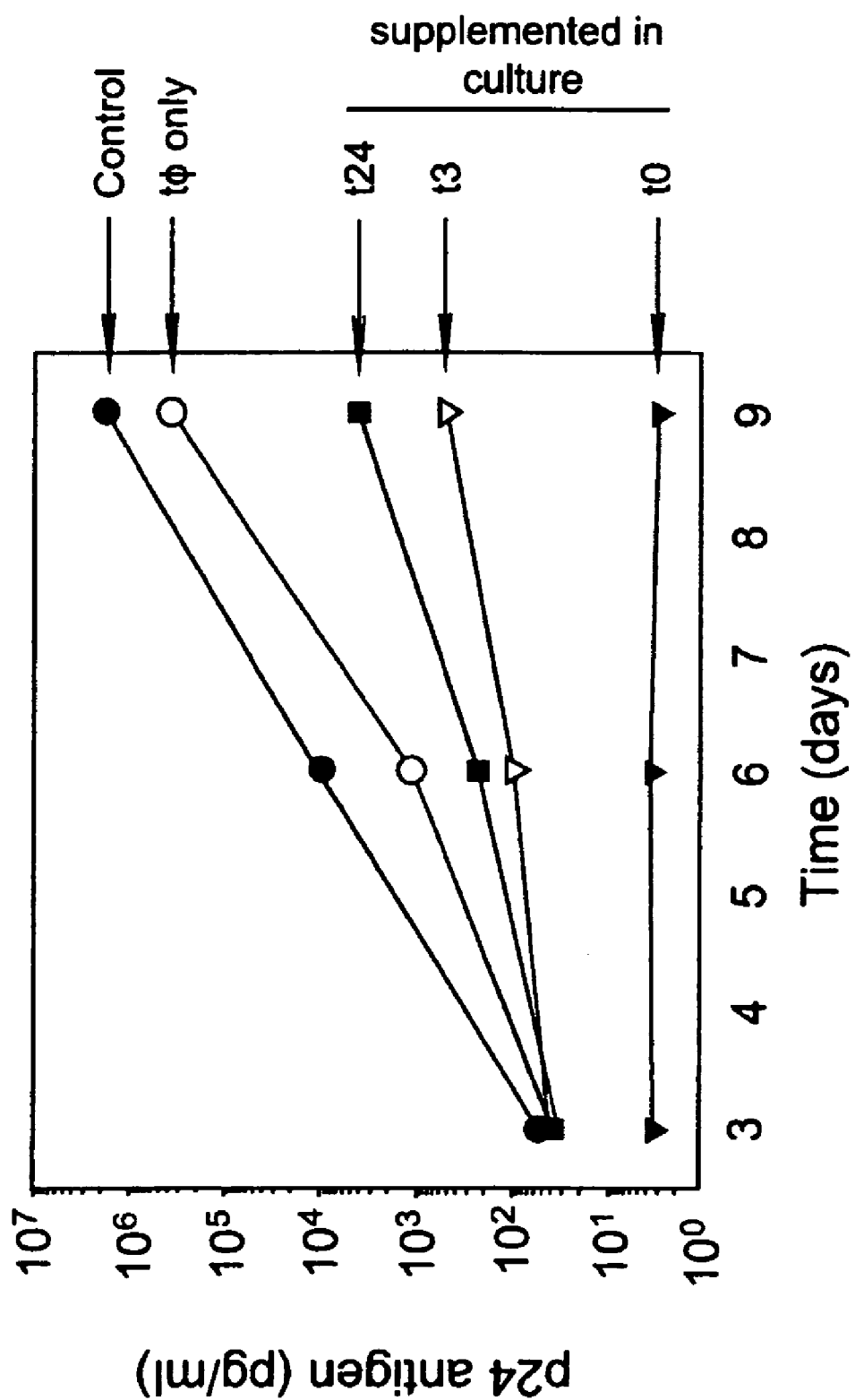
FIG. 6. Retrocyclin can inhibit HIV-1 spread when administered up to 24 hrs post-infection. Primary $CD4^+$ PBMC were incubated with HIV-IIIB for 3 hours in the absence ("control", "t0", "t3", and "t24") or presence ("t0 only") of 20 µg/ml retrocyclin. Cells were transferred to fresh R10-50 media that was either supplemented immediately with 20 µg/ml retrocyclin ("t0"), or 3 or 24 hrs after transfer ("t3" and "t24", respectively). "Control" and "tφ only" were not supplemented after transfer. p24 antigen was measured by ELISA as previously described.

Examining the effect of adding retrocyclin at various times pre- and post-HIV-1 infection. To determine if retrocyclin is effective against HIV-1 when added post-infection, we either: 1) added retrocyclin at the time of HIV-1 infection, then washed away the peptide, or 2) added retrocyclin at various times post-infection. Primary CD4+ PBMC were incubated with HIV-IIIB (FIG. 6) or HIV-JR-CSF for 3 hours in the presence or absence of 20 μg/ml retrocyclin. The cells were subsequently washed in media, and incubated an additional 9 days. Retrocyclin (20 μg/ml) was added back to some of the cultures at time points specified in FIG. 6 and infection was monitored by p24 ELISA as previously described. Although retrocyclin was most active when administered at the time of infection, and when present in culture throughout the 9 day incubation, retrocyclin administered as late as 24 hours after initial infection still reduced the p24 concentration by nearly 1000-fold.

Figure 7:
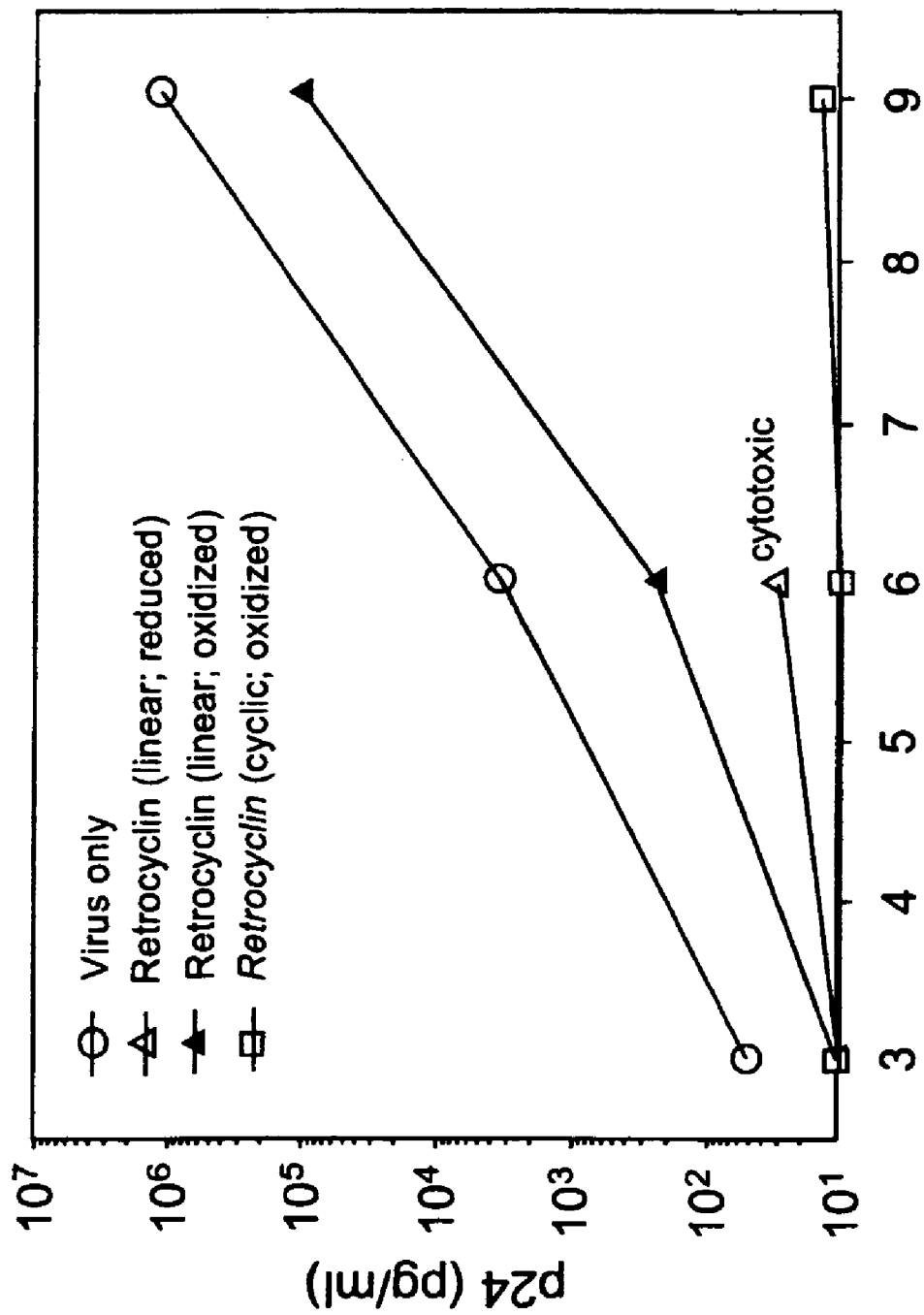
FIG. 7. Mature retrocyclin, but not premature forms, inhibit HIV-1 replication. H9 cells were incubated with HIV-IIIB (MOI=$10^{-2}$) for 3 hours in the absence or presence of 20 µg/ml retrocyclin in three flavors: linear and reduced; linear and oxidized disulfide bonds; and the mature form (cyclic and oxidized). Assay sensitivity is 10 pg/ml.

Cyclization and oxidation are necessary for retrocyclin's antiviral activity. Mature retrocyclin was prepared by a three-step process. Its two intermediate forms, as well as the final retrocyclin product were tested in our standard assay of HIV-1 infectivity: p24 ELISA of HIV-IIIB infection of H9 cells (FIG. 7). Intermediate 1 (open triangles) is the linearized retrocyclin octadecapeptide with 6 reduced cysteine thiol groups. Intermediate 2 (closed triangles) is a noncyclic b-hairpin octadecapeptide with 3 intramolecular cystine disulfide bonds. Retrocyclin (open squares), is a cyclized octadecapeptide with 3 disulfide bonds. Note that only the "mature" form of retrocyclin was antiviral, compared to control (no retrocyclin, open circles). Unlike retrocyclin, the linearized octadecapeptide was highly cytotoxic, as measured by trypan blue exclusion, and treated cells did not survive past 6 days.

Figure 8:
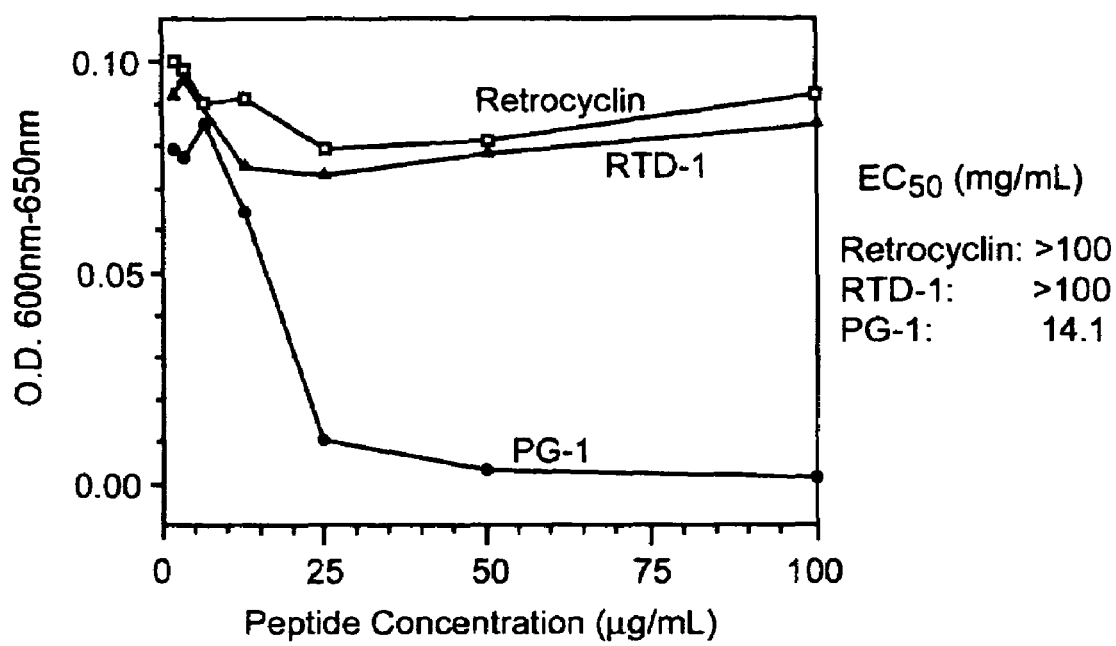
FIG. 8. Cytotoxicity of antimicrobial peptides against H9 cells. Retrocyclin, RTD-1 and PG-1 (a porcine-derived peptide with anti-HIV-1 activity) were tested for cytotoxicity using an MTT assay for cell proliferation. Note that the $EC_{50}$ of Retrocyclin and RTD-1 were >100 µg/ml, concentrations well above their antiviral concentration.

Retrocyclin is not cytotoxic. Cytotoxicity determinations were made with a Cell Proliferation Kit from Boehringer Mannheim used according to the manufacturer's instructions. The procedure measures the reduction of the yellowish MTT molecule (3-[4,5-dimethylthiazol-2-yl]-2,5-diphenyl tetrazolium bromide) to a dark blue formazan. Retrocyclin exhibited little to no cytotoxicity against H9 cells (FIG. 8) and ME-180 cervical carcinoma cells at 100 μg/ml, a concentration that is far higher than the concentrations required for complete protection against HIV-1 infection (10 μg/ml). Additionally, neither 20 μg/ml retrocyclin nor RC-101 were cytotoxic to HIV-1-infected H9 cells and CD4+ PBMC as measured by trypan-blue exclusion (Table 1). Retrocyclin was not hemolytic for human erythrocytes.

TABLE 1

Cytotoxicity of 20 μg/ml peptide against H9 cells and CD4+ PBMC (peripheral blood mononuclear cells) as measured by Trypan blue exclusion.

| Cells; virus | no peptide* | Retrocyclin |
| --- | --- | --- |
| CD4+ PBMC; no virus | 1.07 | 0.98 |
| H9; IIIB | 0.78 | 1.20 |
| CD4+ PBMC; IIIB | 1.71 | 1.68 |
| CD4+ PBMC; JR-CSF | 0.90 | 1.58 |

*Values expressed as the average number of cells × $10^6$/ml for 2–3 experiments.
N.D. = no data.

Construction and characterization of retrocyclin congeners. To date, we have constructed over a dozen congeners of retrocyclin, "RC-101", "RC-102", "RC-103", etc. and have used them to commence a structure-activity analysis of the retrocyclin's antiviral and antimicrobial effects. These peptides, whose sequences are shown in Table 2, were synthesized, oxidized, cyclized, and purified as described above for retrocyclin. RC-101 was prepared because retrocyclin, a circular peptide without free N-terminal or side-chain amine groups, is not well suited for fluorescent-conjugation. RC-101 is identical in sequence to retrocyclin (RC-100) except for the presence of an $Arg_9 \rightarrow Lys_9$ substitution. This modification preserves the net cationic charge of the peptide and provides an available epsilon-amino group in lysine's side chain. Importantly, RC-101 was as active as retrocyclin in protecting cells from infection by HIV-1 (FIG. 11), indicating that substitutions in the primary sequence of retrocyclins can be made without losing anti-retroviral activity. The labeling of RC-101 with amine-reactive probes will be described in a later section.

Five additional analogues (RC 110-114) have been synthesized, cyclized and purified. RC-110 (Inverso-enantioretrocyclin), a cyclic peptide composed exclusively of D amino acids, has a sequence that is identical to retrocyclin, but with its residues placed in reverse order.

The ability of RC100 and several analogues described in Table 2 to protect cells from infection by X4 (HIV-IIIB) and R5 (JR-CSF) strains of HIV-1 is shown in FIG. 9. The structure of retrocyclin itself is shown in FIG. 10, with its residues numbered to correspond to Table 2.

The p24 assay results shown in FIG. 9 are on a logarithmic scale. A horizontal reference line that passes through 100 on the ordinate scale corresponds to 1 pg/ml of p24 antigen. Results from 3 experiments (each performed with PBMC from a different donor) are shown. Retrocyclin was uniformly protective against both strains of HIV-1 in all of the experiments. Most of the mono-tyrosine substituted amino acid congeners of retrocyclin (RC-102, RC-103, RC-105, RC-106, and RC-108) were either inactive or only modestly active in inhibiting HIV-1 infection by Strain IIIB. In contrast, RC-102, RC-103 and RC-104 showed considerable ability to protect cells from infection by the JR-CSF strain (R5).

These results allow some hypotheses about the mechanism of action of retrocyclins to be formulated. Because RC-112 (enantioRetrocyclin) was relatively ineffective, chiral interactions between retrocyclin and one or more receptors on the cell and/or virus surface are likely to participate in the protective mechanism. Since certain analogues (RC-102, RC-103 and perhaps RC-104) manifested substantial activity against the R5 strain but were relatively ineffective against the X4 strain, the mechanisms whereby retrocyclin inhibits these strains are not identical. The lack of efficacy of RC-106, RC-107 and RC-108 (each containing a tyrosine for arginine replacemene) suggests that ionic interactions involving the positively charged arginine residues in position 4, 9, and 13 of retrocyclin (see the model in FIG. 10) with oppositely charged groups (e.g., phosphate) on the surface of the target cell or HIV-1 virion also participate in the process. In preliminary surface plasmon resonance (SPR) experiments, we have observed that retrocyclin binds with high affinity to certain sphingolipids (e.g., galactosylceramide) that are present in cell-surface rafts, and have been implicated in the cellular uptake of HIV-1 virions.

are different from the direct inactivation of herpes simplex virus previously observed with human and rabbit α-defensins.

Retrocyclin binds to T1 cells. Since retrocyclin does not directly inactivate HIV-1 virions, the ability of retrocyclin to interact with a cellular target was determined, using RC-101, a $Arg_9 \rightarrow Lys_9$ congener of retrocyclin that retained the antiretroviral activity of the parent molecule. RC-101 was conjugated to the amine-reactive fluorescent dye, BODIPY-FL (Molecular Probes), according to the manufacturer's protocol. The conjugate ($RC-101_{BODIPY-FL}$) was purified by reverse-phase HPLC and resuspended in 0.01% acetic acid

TABLE 2

Primary amino acid sequence of selected retrocyclin congeners.

| SEQ ID NO: | Peptide | Name (or comment) | Avg. (Da) MW | Amino acid sequence |
|---|---|---|---|---|
| 1 | RC-100* | Retrocyclin | 1918.4 | GICRCICGRGICRCICGR |
| 2 | RC-101 | $R_9$K-Retrocyclin | 1890.4 | GICRCICGKGICRCICGR |
| 3 | RC-102 | $I_6$Y-Retrocyclin | 1968.5 | GICRCYCGRGICRCICGR |
| 4 | RC-103 | $I_{15}$Y-Retrocyclin | 1968.5 | GICRCICGRGICRCYCGR |
| 5 | RC-104 | $I_2$Y-Retrocyclin | 1968.5 | GYCRCICGRGICRCICGR |
| 6 | RC-105 | $I_{11}$Y-Retrocyclin | 1968.5 | GICRCICGRGYCRCICGR |
| 7 | RC-106 | $R_4$Y-Retrocyclin | 1925.4 | GICYCICGRGICRCICGR |
| 8 | RC-107 | $R_9$Y-Retrocyclin | 1925.4 | GICICICGYGICRCICGR |
| 9 | RC-108 | $R_{13}$Y-Retrocyclin | 1925.4 | GICICICGRGICYCICGR |
| 10 | RC-109** | | | GICICICGRGICRCICGY |
| 19 | RC-110 | Inverso-enantio-Retrocyclin | 1918.4 | RGCICRCIGRGCICRCIG (ALL D) |
| 20 | RC-111 | Inverso-retrocyclin | 1918.4 | RGCICRCIGRGCICRCIG |
| 21 | RC-112 | enantio-retrocyclin | 1918.4 | GICRCICGRGICRCICGR (all D) |
| 22 | RC-113 | enantio-RC-101 | 1890.4 | GICRCICGKGICRCICGR (all D) |
| 23 | RC-114 | RC-101/103 hybrid | 1940.4 | GICRCICGKGICRCYCGR |

With the exception of RC-109, all of the above peptides are cyclic.
*RC-100 is a synonym for retrocyclin, RC-111 (inverso-retrocyclin) is composed of L-amino acids; RC-110, 112 and 113 are composed exclusively of D-amino acids. RC-109 failed to cyclize, and has not been tested further.

Figure 12:
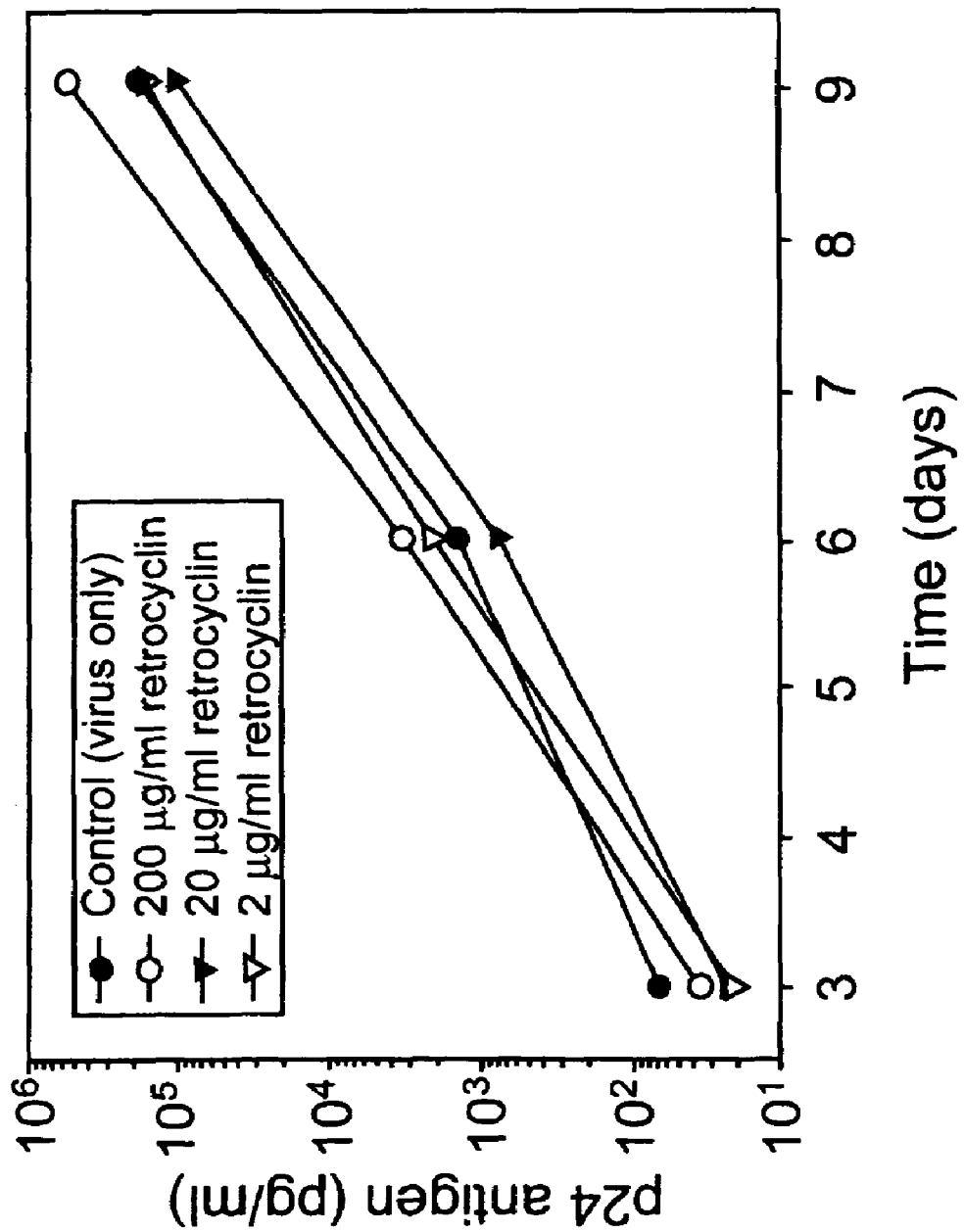
FIG. 12. Adding retrocyclin directly with HIV-IIIB does not reduce infection of H9 cells. Retrocyclin (2-200 µg/ml) was incubated with HIV-IIIB (MOI=$10^{-2}$) diluted in R10 media prior to infecting H9 cells. p24 antigen release was measured by ELISA. Limit of detection=10 pg/ml.
Figure 13:
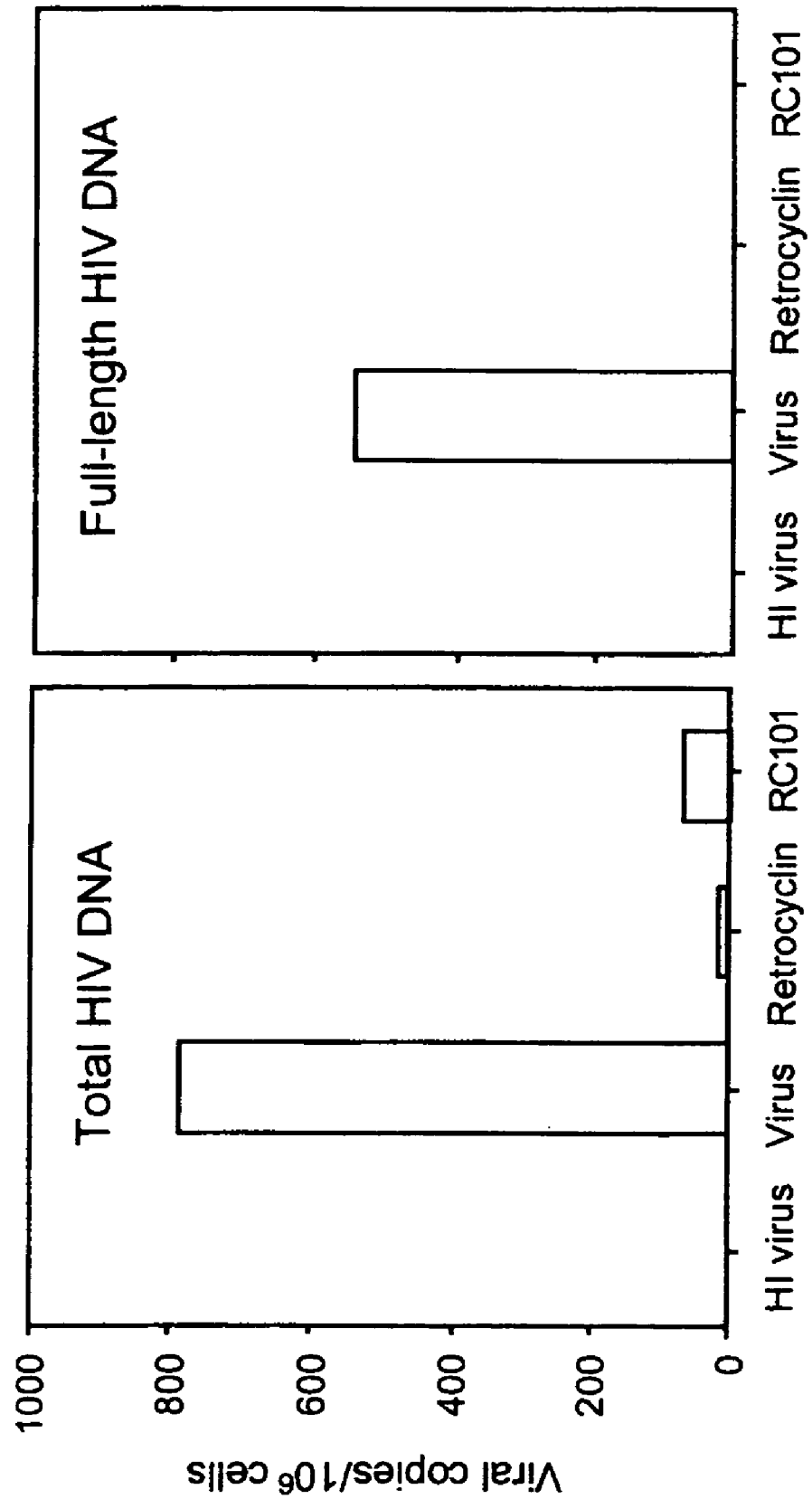
FIG. 13. Retrocyclin and RC-101 inhibited the formation of HIV proviral DNA. Retrocyclin and RC-101 inhibited the formation of DNA from both early events (total HIV DNA) and later events (full-length HIV DNA) of reverse transcription. Data are an average of 2 experiments, except for RC-101 (1 experiment). "HI virus" is a heat-inactivated virus control for background levels of viral DNA.

Retrocyclin does not directly inactivate HIV-1. To determine if retrocyclin directly inactivated HIV-1 virions, HIV-IIIB (MOI $10^{-2}$) was incubated with 2 μg/ml, 20 μg/ml, or 200 μg/ml retrocyclin for 30 min at room temperature in R10 media. The mixture was diluted 190-fold in R10 media, to dilute retrocyclin below its effective antiviral concentrations (no significant antiviral activity at <2 μg/ml; n=5), and used to infect $5 \times 10^5 H_9 CD4^+$ cells. Viral replication was measured by collecting supernatant for 9 days at 3 day intervals to quantify HIV-1 p24 antigen by ELISA (FIG. 12). HIV titer was not reduced with the highest concentration (200 μg/ml) of retrocyclin, demonstrating that retrocyclin does not target the virion directly. In this respect, the actions of retrocyclin at up to 240 μg/ml. $RC-101_{BODIPY-FL}$ (20 μg/ml) was incubated with $2.5 \times 10^5$ CD4$^+$-selected PBMC cells for 15 min at room temperature, washed once in fresh R10-50 media. Specimens were imaged on a Leica TCS-SP Confocal Microscope (Heidelberg, Germany) equipped with an argon laser for excitation of BODIPY-FL and phycoerythrin (PE). Images were collected with Leica Confocal Software. $RC-101_{BODIPY-FL}$ bound to the cell membrane, mostly in patches. Patching ("microaggregation") has been reported to occur with hormone-occupied epidermal growth factor receptors (95), and "rafts" are involved in signaling through the confinement of chemokine receptors to discrete regions of the cell membrane. $RC-101_{BODIPY-FL}$ colocalizes with phycoerythrin (PE)-labeled monoclonal antibodies directed against CXCR4, CCR5 and CD4, but does not with PE-labeled isotype control antibodies. Thus, retrocyclin aggregates in the same "rafts" as the receptor and coreceptors for HIV-1. In addition, RC-101$_{BODIPY-FL}$ aggregated in patches where CD4, CXCR4 and CCR5 levels were weak or absent A flow cytometry experiment was performed to examine binding of BODIPY-labeled RC-101. T1 cells were incubated for 1 hr at 37° C.±20 µg/ml RC-101$_{BODIPY-FL}$, washed with R10 media, and fixed in 2% paraformaldehyde/PBS. Cells were analyzed by fluorescence-activated cell sorting (FACS) on a Becton-Dickinson FACScan. Live cells ($10^4$ events) were gated and analyzed by CellQuest. Two peaks were present, which may represent non-specific and specific cellular binding Retrocyclin inhibits HIV replication at an early step (reverse transcription or before). To determine whether retrocyclin blocked the formation of proviral DNA in HIV-JR-CSF-inoculated CD4$^+$-selected PBMC, quantitative real time PCR was performed. This method is more sensitive than measuring p24 release and can detect infection even when p24 values may be affected by virus carried over from the original inoculum. CD4$^+$-selected PBMC ($10^6$ cells) were incubated in 250 µl at 37° C./5% $CO_2$ for 3 hr with either HIV-1 strain JR-CSF (MOI=0.1), heat-inactivated virus (background control), JR-CSF+20 µg/ml retrocyclin or JR-CSF+20 µg RC-101. Cells were washed and resuspended in 1 ml R10-50 media, and incubated for an additional 9 hours. Following incubation, cells were pelleted at 300×g, removed of overlying supernatant, and stored at –80° C. until analyzed by real time PCR. Retrocyclin and RC-101 inhibited the formation of HIV-1 proviral DNA (FIG. 13), indicating that retrocyclin acts early, either to inhibit reverse transcription or preceding events.

Figure 14:
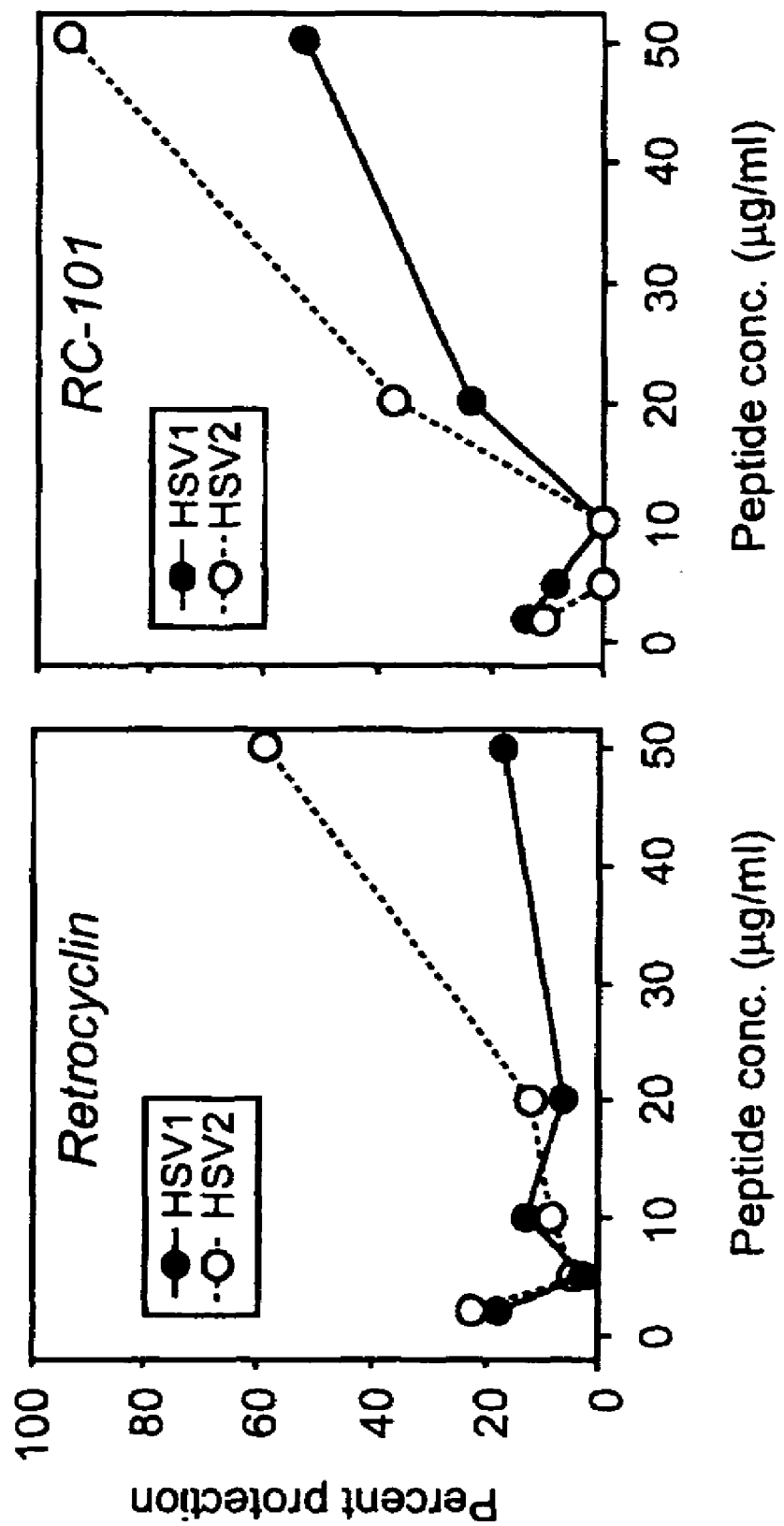
FIG. 14. Inactivation of HSV-1 and HSV-2 by retrocyclin and RC-101. Retrocyclin (left panel) and RC-101 (right panel) at the indicated concentrations were incubated with herpes simplex virus, type 1 (HSV-1) or HSV-2 for 2 hrs and then added to ME-180 cell monolayers. Cells were incubated at 37° C. for 72 hrs, and cytotoxicity was measured with an MTT kit.

Some retrocyclins are slightly active against herpes simplex virus (HSV). To determine if the activity of retrocyclin against HIV-1 was specific or representative of a more global antiviral effect, it was tested its ability to prevent HSV infection in vitro. A quantitative microplate assay was used to screen retrocyclin and retrocyclin-congeners for their ability to inactivate HSV type 1 (HSV-1) and HSV-2. The assay utilized small amounts of peptide and simultaneously evaluated for peptide-induced cytotoxicity. In brief, final peptide concentrations of 2-50 µg/ml were incubated with virus stocks for 2 hrs and added directly to ME-180 human cervical carcinoma cells. Cultures were incubated at 37° C. for 72 hrs and cytotoxicity was measured using a 3-(4,5-dimethylthiazon-2-yl)-2,5-diphenyltetrazolium bromide (MTT) cell proliferation kit (Boehringer-Mannheim, Germany). Calculations to assess antiviral activity and compute "percent protection" are delineated in (90). Retrocyclin afforded modest protection against HSV-2, but not HSV-1 (FIG. 14). In contrast, RC-102 and RC-103 were less antiviral than retrocyclin. However, RC-101 was modestly protective against HSV-1 and nearly completely protective against HSV-2. The substitution of Arg$_9$→Lys$_9$ produced a retrocyclin congener that retained activity against HIV-1, bacteria and fungi, and was more active against HSV.

Example 3

Sequences of Retrocyclins

We have obtained samples of DNA from the 22 primate species listed below in the Table. The first column shows the phylogenetic group, and has the following key: E. Great apes/humans; C: Old World Monkeys; B: New World Monkeys, D. Lesser Apes; A. Column 3, showing "Genetic distance" from Homo sapiens, is expressed in %. These values come from study of gamma globin DNA (Page, S L., Chiu C, and Goodman, M. Molecular phylogeny of Old World Monkeys (Cercopithecidae) as inferred from gamma-globin DNA sequences. Molecular Phylogenetics and Evolution. 1999. 13:348-359.) Column four shows the sources of DNA samples: 1, the Coriell Institute; and 2, the "Frozen Zoo" collection of the San Diego Zoo. We have performed RT-PCR on all of these samples with primers based on the sequence of the human retrocyclin gene. "Pending" means that the studies are still undergoing confirmation.

All of the great apes (Group E) have a retrocyclin gene or pseudogene. In the gorilla and chimpanzee the gene was inactivated by the identical signal sequence stop codon mutation found in the human retrocyclin pseudogene. A Sumatran orangutan DNA sample obtained from the Coriell Institute contained two retrocyclin genes. One gene contained the signal sequence mutation and the other appeared intact. Additional orangutan DNA samples have been obtained from the "Frozen Zoo" (described below) and are being characterized. None of the 6 New World monkeys (Group B) or 5 the prosimian species (Group A) had a retrocyclin gene.

TABLE 3

| Group | Species | Genetic Distance | DNA Source | Retrocyclin Gene | Retrocyclin Gene Status |
|---|---|---|---|---|---|
| E | Homo sapiens | 0.0 | 1 | Present | inactivated |
| E | Pan troglodytes (chimpanzee) | 1.6 | 1 | Present | inactivated |
| E | Pan paniscus (Bonobo) | 1.7 | 1 | Present | inactivated |
| E | Gorilla gorilla (Lowland gorilla) | 1.9 | 1 | Present | inactivated |
| E | Pongo pygmaeus pyg. (Borneo orangutan) | 3.1 | 2 | pending | pending |
| E | Pongo pygmaeus abeli (Sumatra orangutan) | 3.1 | 1, 2 | Present | intact/inactivated |
| D | Hylobates syndactylus (siamang) | 4.2 | 2 | Present | pending |
| C | Macaca mulatta (Rhesus macaque) | 6.1 | 1 | Present | intact |
| C | Macaca nemestrina (pigtail macaque) | 6.4 | 1 | Present | intact |
| C | Theropithecus gelada (Gerlada baboon) | 6.3 | 2 | pending | pending |

TABLE 3-continued

| Group | Species | Genetic Distance | DNA Source | Retrocyclin Gene | Retrocyclin Gene Status |
|---|---|---|---|---|---|
| C | *Colobus guereza kiku.* (Kikuyu colobus) | 6.8 | 2 | Present | pending |
| B | *Alouatta seniculus* (Red Howler monkey) | 12.7 | 2 | Absent | n.a. |
| B | *Callicebus moloch* (Titi monkey) | — | 2 | Absent | n.a. |
| B | *Pithecia pithecia* (white-faced Saki) | — | 2 | Absent | n.a. |
| B | *Sanguinus fuscicollis* (Saddleback tamarin) | — | 2 | Absent | n.a. |
| B | *Callithrix pygmaea* (Pygmy marmoset) | — | 2 | Absent | n.a. |
| B | *Ateles geoffroyi* (Black handed spider mky) | 11.7 | 1 | Absent | n.a. |
| A | *Sanguinus labiatus* (Red-bellied tamarin) | — | 1 | Absent | n.a. |
| A | *Lemur catta* (Ring-tailed lemur) | ~21.3 | 1 | Absent | n.a. |
| A | *Varecia variegata ruber* (lemur) | — | 2 | Absent | n.a. |
| A | *Otolemur crassicaudatus* (galago) | 28.1 | 2 | Absent | n.a. |
| A | *Nycticebus coucang* (Bengal slow loris) | — | 2 | Absent | n.a. |

Our inferences from these results are: a) The α-defensin precursor of the retrocyclin gene appeared after the Old World (B) and New World (C) monkey lineages separated. The retrocyclin gene appeared in Old World Monkeys (B) and persisted until the orangutan lineage split from the lineage of Gorillas/Chimpanzees/Humans, some 15 million years ago.

same nonapeptide precursor. The third retrocyclin gene encodes a variant nonapeptide with a glycine to arginine mutation.

In the Table 4, "Hs8_19639" is the NCBI identifier for the *Homo sapiens* chromosome 8 working draft sequence segment (Length=3,410,705 bp). The retrocyclin nonapeptide is underlined.

TABLE 4

| Hs8_19639 | Chromosomal location | Translated sequence |
|---|---|---|
| Chromosome 8 | 2,814,641 (SEQ ID NO:124) | (SEQ ID NO:125) V T P A Met R T F A L L T A Met L L L V A L Stop A Q A E P L Q A R A D E A A A Q E Q P G A D D Q E Met A H A F T W H E S A A L P L S |
|  | 2,813,782 | S D S A R G L <u>R C I C G R G I C</u> R L L Stop R R F G S C A F R G T L H R I C C |
| Chromosome 8 | 1,742,910 (SEQ ID NO:120) | (SEQ ID NO:121) V T P A Met R T F A L L T A Met L L L V A L Stop A Q A E P L Q A R A D E A A A Q E Q P G A D D Q E Met A H A F T W H E S A A L P L S |
|  | 1,742,051 | S D S A R G L <u>R C I C G R R I C</u> R L L Stop R R F G S C A F R G T L H R I C C |
| Chromosome 8 | 1,478,367 (SEQ ID NO:122) | (SEQ ID NO:123) V T P A Met R T F A L L T A Met L L L V A L Stop A Q A E H F R Q E L Met K L Q P R S S L E Q Met I R K W L Met L Y Met A Stop K C R S S A F |
|  | 1,479,224 | S D S A R G L <u>R C I C G R G I C</u> R L L Stop R R F G S C A F R G T L H R I C C |

In a recent search of the NCBI human genome data base, two additional human retrocyclin genes were identified. Each gene contains a silencing mutation in its signal sequence. Two of the three retrocyclin genes encodes the Based on the above information, the primate ancestor of *Homo sapiens* could have expressed three retrocyclins. The structures of these peptides, called Retrocyclin 1, 2 and 3 are shown in FIG. 10A.

Three orangutan clones represent at least two different retrocyclin genes. The sequences are shown in FIG. 15. The stop codons in orangutan clone 19 are identical to those in human retrocyclin. Accordingly, clone 19 also represents an expressed pseudogene. Overall, 132/143 (92.3%) of translated products (including stop codons) from orangutan clone 19 and the human retrocyclin gene are identical. The translation products of orangutan clones 20 and 21 are identical in 141/143 (98.6%) sites. Both clones lack a silencing stop codon in their signal sequence, and should be capable of producing a functional demidefensin whose tandem nonapeptide elements (underlined) would produce a peptide identical to human retrocyclin. The predicted translation products of orangutan clone 20 and human retrocyclin are identical in 129/143 (90.2%) of positions. All three orangutan clones, #19, 20 and 21 came from the DNA of a single orangutan, It remains to be determined if the genes they represent are alleles, or if the retrocyclin locus has undergone duplication and additional retrocyclin genes remain to be found.

As shown in FIG. 15, this portion of the human retrocyclin gene encodes four stop codons (●). The first of these occurs near the end of the putative signal sequence and should abort translation. The second stop codon occurs after cysteine 3, and marks the end of the putative demidefensin sequence. The third stop codon comes after the CCR residues and marks the customary termination of an α-defensin. The final stop codon occurs after the FES tripeptide in a non-expressed region of the gene.

One Gorilla retrocyclin clone has been sequenced. Its translation product is identical to human retrocyclin in 139/143 (97.2%). The sequence is shown in an alignment with the human sequence in FIG. 15. The silencing stop codon (●) is present in the signal sequence. Consequently, this clone represents an expressed pseudogene.

Note that the chimp (*Pan troglodytes*) and the Bonobo (*Pan paniscus*) genes contain the first stop codon (●) in the signal sequence, but both lack the retrocyclin-geherating stop codon after cysteine 3 in the defensin-region. From these features, the chimp would appear to have silenced an α-defensin gene. There is an additional mutation (cysteine to glycine) in the chimp's nonapeptide region (double underlined), which was presumably acquired after the gene had been silenced by the signal sequence mutation)

Unlike human retrocyclin, the pigtail and rhesus macaque genes lack a premature stop codon (●) in their signal sequences. Both macaque genes have acquired a stop codon in a nontranslated portion of their gene, between cysteines 4 and 5 of the original defensin domain.

Example 4

We have synthesized over 20 retrocyclin congeners (RC's), and describe three of these peptides herein: RC-101, RC-115 and RC-116. Although RC-115 and RC-116 were not superior in activity to retrocyclin-1, their radio-iodinated derivatives are useful for pharmacokinetic studies. The enhanced antiviral activity of RC-101 suggests that the θ-defensins that exist (or existed) in nature are not optimized for activity against HIV-1.

Alpha, beta and theta defensins of primates are reviewed by Lehrer. (See Lehrer (2004) Nature Reviews Microbiology 2(9):727-38). The activity of several human α-defensins against HIV-1 has been reported (See Wang, et al (2004) J. Immunol 173(1):515-520); and the activityof human beta defensins 2 and 3 against HIV-1 was also shown. (See Quinones-Mateu et al (2003) AIDS. 17(16):F3948).

Materials and Methods

Viral isolates. Primary HIV-1 isolates were obtained from Institutional Review Board-approved Centers for Disease Control and Prevention (CDC) Studies or from the National Institutes of Health Research and Reference Reagent Program and World Health Organization collaborative network. Detailed characteristics of the CDC isolates, including subtype determination based on the envelope region, and co-receptor usage using GHOST cell lines have been described elsewhere. For viruses obtained from the NIH Research and Reference Reagent Program, the reported subtype and co-receptor data were used as supplied. Viral stocks were generated by infecting CD8-depleted normal human peripheral blood mononuclear cells. After filtration through 0.22-μm filters, aliquots of the stocks were stored at −70° C. until used.

Peptide synthesis and purification. Retrocyclin-1 and the analogues shown in Table 1 were synthesized in our laboratory as previously described, using Fmoc chemistry and resins and amino acid precursors purchased from AnaSpec, Inc. (San Jose, Calif.). The peptides were at least 95% pure.

Reporter gene-based viral replication assay. JC53-BL cells, an HIV-1 reporter cell line derived from HeLa cells that expresses high levels of CD4 and the HIV co-receptors CXCR4 and CCR5, were a gift of Tranzyme Inc. (Birmingham, Ala.). The JC53-BL cells contain cassettes for luciferase and β-galactosidase, each driven by the HIV-1 LTR. HIV infection (tat production) can be detected either by measuring luciferase activity or by counting blue foci after staining the cells with "X-Gal" (5-Bromo-4-chloro-3-indolyl β-D-galactopyranoside), as described elsewhere in detail. The JC53-BL cells were maintained in Dulbecco's modified Eagle medium supplemented with 10% fetal calf serum. (HyClone, Logan, Utah), 2 mM glutamine (Gibco), 100 units per ml penicillin G and 100 μg/ml streptomycin (GIBCO™, Invitrogen Corp., San Diego, Calif.). Viral titers were determined by adding serial dilutions of the virus stocks, in triplicate, to wells containing 20,000 JC53-BL cells, after supplementing the above medium with 40 μg/ml DEAE (diethylaminoethyl)-dextran. After a 48 hour incubation at 37° C. in 5% $CO_2$, the cells were fixed and stained for β galactosidase, and the blue foci were counted with a light microscope. Multiplicity of infection (MOI) values were taken from the infectious unit data.

In vitro infections were carried out in the presence or absence of θ-defensin peptides. Briefly, JC53-BL cells were harvested from T-150 flasks approximately 18 hours prior to starting the assay with 0.1 mM EDTA in 0.017 M PBS, pH 7.4. The cells were washed and transferred to sterile white 96-well plates (Thermo Labsystems, Franklin, Mass.) at a density of 20,000 cells in 50 μl of medium. Three hours before adding the virus, the peptides of interest were added to the wells to give final concentrations of 1.25, 2.5, 5 and 10 μg/ml. After this 3-hour preincubation with peptides, viruses were added in media containing 40 μg/ml DEAE-dextran. The final volume was 200 μl per well, and the multiplicity of infection (viruses/cell) ranged from 0.009 to 0.65. After the plates had incubated at 37° C. in 5% $CO_2$ for 48 hours, luciferase activity was measured with the Steady-Glo Luciferase Assay System (Promega, Madison, Wis.), using the manufacturer's lysis protocol. Relative light intensity was measured with a Tecan luminometer running Magellan software (Tecan, Research Triangle Park, N.C.) and reported as relative light units (RLU). Each plate contained three sets of quadruplicate controls: media-only (background), virus-only (peptide-free), and recombinant luciferase. Samples were run in duplicate and the % inhibition was calculated from the mean values using the formula:

% Inhibition=1−(average RLU peptide+virus wells/average RLU virus only wells)×100.

Fifty-percent inhibitory concentration values ($IC_{50}$) were calculated using the predicted exponential growth function in Microsoft Excel, which uses known x-y values to estimate a given x value (in this case concentration of peptide) that would correspond to a given y value (in this case $IC_{50}$). Statistical comparisons were by paired t-tests, unless otherwise noted.

Cytotoxicity. Cytotoxicity was analyzed by trypan blue-dye exclusion and with a MTT-based cell proliferation kit (Boehringer Mannheim, Indianapolis, Ind.). MTT is 3-(4,5-dimethylthiazol-2-yl)-2,5-diphenyltetrazolium bromide. Measurements were performed using the manufacturer's protocol.

Surface plasmon resonance. Recombinant human soluble CD4 (full-length 45 kDa glycosylated ectodomain) was produced by ExpresSF+S. frugiperda cells in serum-free medium (Protein Sciences Corporation, Meriden, Conn.). Glycosylated HIV-1 gp120 (LAV) envelope glycoprotein (Catalog No. 2003-LAV) was purchased from the same source. Recombinant HIV-1BaL was obtained through the AIDS Research and Reference Reagent Program, Division of AIDS, National Institute of Allergy and Infectious Disease, NIH.

Surface plasmon resonance (SPR) experiments were done with a Biacore 2000 system (Biacore, Inc., Piscataway, N.J.). The running buffer (pH 7.4) contained 10 mM HEPES, 150 mM NaCl, 3 mM EDTA and 0.005% polysorbate 20. The immobilized proteins (gp120-LAV and CD4) were dissolved at 20 µg/ml in 10 mM sodium acetate, pH 5.0 and immobilized on a Biacore CM5 sensor chip using the amine coupling method. The chip was activated by mixing 400 mM EDC (N-ethyl-N-(3-dimethylaminopropyl)-carbodiimide hydrochloride) and 100 mM N-hydroxysuccinimide. An immobilization level of ~6000 response units (RU) was attained for each bound protein. Residual reactive groups on the chip surface were blocked using 1.0 Methanolamine/HCl, pH 8.5.

The flow cell chip used as a control lacked immobilized protein but was otherwise treated as above. Signals were corrected for nonspecific binding by subtracting the control signal. To regenerate the chip surface, bound ligands were removed with 10 mM HCl. Data were analyzed with BIAevaluation 3.1 software. Curve fitting was done with an assumption of 1:1 binding.

Results

Figure 16:
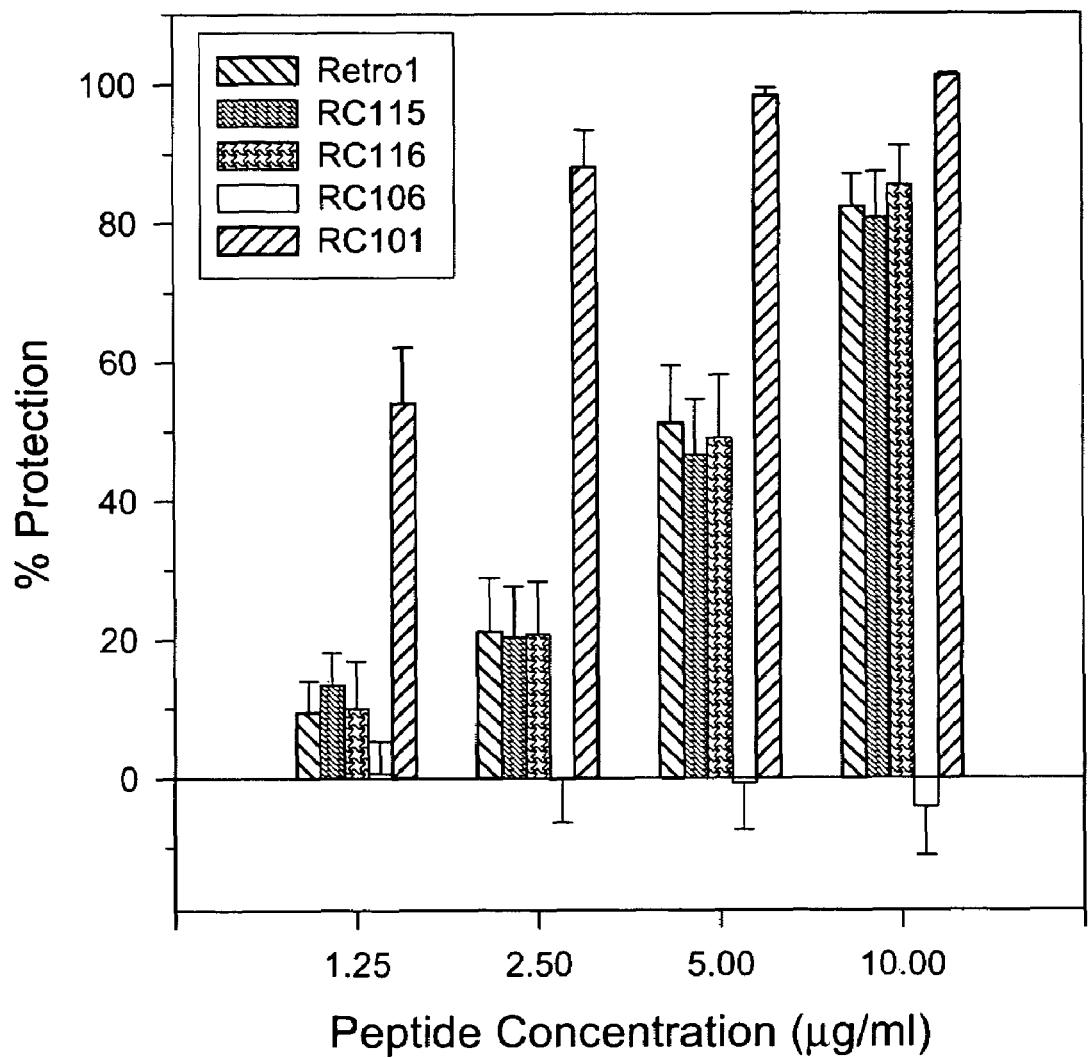
FIG. 16. Activity against subtype B strains. Protective activity of the E defensins was tested at four peptide concentrations: 1.25, 2.5, 5.0 and 10.0 µg/ml. The bars show mean % protection±S.E.M., n=7. Retro1 is retrocyclin-1 (RC-100). Characteristics of the isolates are shown in Table 6.

FIG. 16 compares the activity of retrocyclin-1 and four retrocyclin congeners (RC-101, RC-106, RC-115 and RC-116) against seven different primary isolates of subtype B HIV-1. Each retrocyclin analog differed from retrocyclin-1 by a single amino acid replacement (Table 5).

TABLE 5

| Peptide | Mass | Sequence of Linear Precursor* | |
|---------|------|-------------------------------|---|
| RC-100 | 1918.4 | GICRC ICGRG ICRCI CGR | (SEQ ID NO: 1) |
| RC-101 | 1890.4 | GICRC ICGKG ICRCI CGR | (SEQ ID NO: 2) |
| RC-106 | 1925.4 | GICYC ICGRG ICRCI CGR | (SEQ ID NO: 137) |
| RC-115 | 1925.4 | GICRC ICGRY ICRCI CGR | (SEQ ID NO: 138) |
| RC-116 | 1925.4 | RYICR CICGR GICRC ICG | (SEQ ID NO: 139) |

The differences between retrocyclin-1 and RC-101 are highly significant at each concentration (p<0.001). RC-106, which has consistently shown little or no anti-HIV activity in our previous assays, was included as a negative control. Whereas the mean $IC_{50}$ value of RC-101 for the seven subtype B strains was <1.25 µg/ml (<660 nM) that of retrocyclin-1 was approximately 5.0 µg/ml (2.6 µM). Table 6 shows $IC_{50}$ results for the individual HIV-1 isolates.

TABLE 6

| Characteristics of the Primary Isolates | | | | $IC_{50}$ Concentrations (µg/ml) | | | |
|---|---|---|---|---|---|---|---|
| Isolate | Origin | Subtype | Coreceptor | RC-100 | RC-101 | RC-115 | RC-116 |
| 92US714 | USA | B | R5 | >10 | | | |
| 93US151 | USA | B | X4 | 1.69 | 0.49 | 2.12 | 1.26 |
| 92HT593 | Haiti | B | X4 | 5.73 | 0.76 | 4.24 | 3.68 |
| 92US727 | USA | B | R5 | 6.46 | | 5.44 | 4.61 |
| 5148-1382 | USA | B | R5 | 5.71 | | | |
| 5157-1326 | USA | B | R5 | 4.64 | 3.59 | | 4.79 |
| 5157-35097 | USA | B | R5X4 | 6.29 | | | |
| 193317 | Nigeria | A | X4 | >10 | | 7.10 | 7.13 |
| 196554 | Senegal | A | R5 | 5.73 | 0.51 | 4.52 | 2.39 |
| 196531 | Cameroon | A | R5 | >10 | 2.65 | 2.69 | 7.80 |
| 92UG037 | Uganda | A | R5 | 1.44 | | | |
| 192431 | Nigeria | C | X4 | 5.18 | 0.54 | 5.41 | 2.4 |
| 193358 | Nigeria | C | R5 | >10 | 2.75 | | 7.75 |
| 98CN009 | China | C | R5 | >10 | 8.53 | | |

TABLE 6-continued

| | Characteristics of the Primary Isolates | | | IC$_{50}$ Concentrations (µg/ml) | | | |
|---|---|---|---|---|---|---|---|
| Isolate | Origin | Subtype | Coreceptor | RC-100 | RC-101 | RC-115 | RC-116 |
| 98TZ017 | Tanzania | C | R5 | >10 | 4.87 | 7.11 | |
| 93UG053 | Uganda | D | R5 | 6.38 | 1.54 | 3.88 | 6.57 |
| 92UG005 | Uganda | D | R5 | 5.18 | 1 | 4.14 | 5.18 |
| 94UG114 | Uganda | D | R5 | 3.69 | | 3.52 | 4.20 |
| HM14 | Thailand | CRF01-AE | X4 | 3.09 | 0.84 | 3.39 | 3.25 |
| 93TH060 | Thailand | CRF01-AE | R5 | 7.39 | 2.15 | 5 | 6.5 |
| HM16 | Thailand | CRF01-AE | | | | | |
| RU132 | Russia | G | R5 | 5.27 | | 3.00 | 4.91 |
| RU570 | | G | R5 | 8.63 | nt | 5.77 | 9.56 |
| 92BR023 | | C/B | R5 | 4.71 | 3.04 | 2.44 | 2.86 |
| 92RW009 | | C/A | R5/X4 | 8.72 | 2.72 | 4.71 | 7.75 |
| 92RW024 | | D/A | R5 | 7.78 | | 4.57 | 6.58 |
| 93UG059 | | A/D | X4 | 6.65 | | 4.67 | 5.7 |

Figure 17:
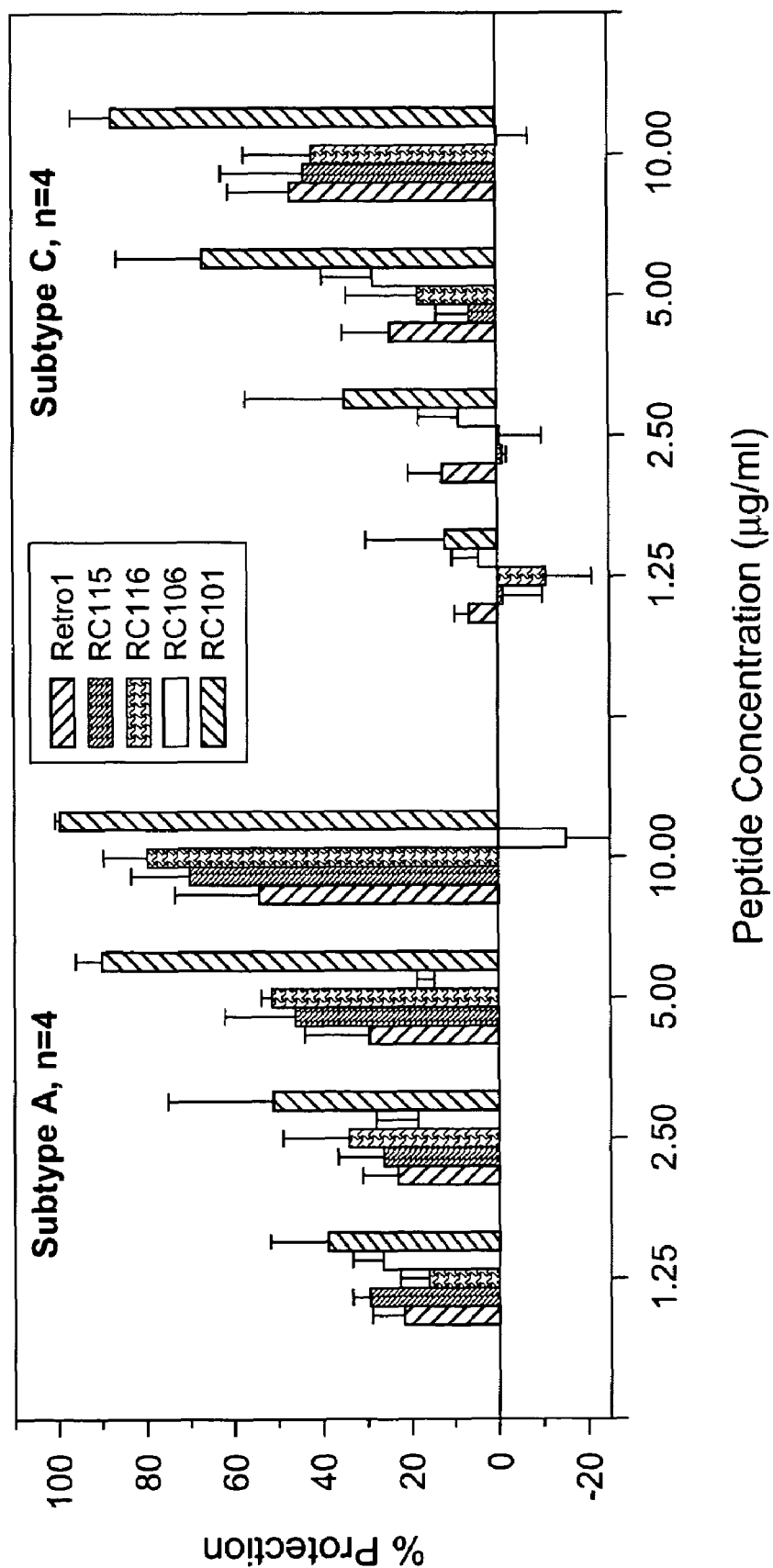
FIG. 17. Activity against subtype A and C isolates. Protective activity of the θ defensins was tested at four peptide concentrations: 1.25, 2.5, 5.0 and 10.0 µg/ml. The bars show mean % protection±S.E.M., n=4 for each subtype.

The IC$_{50}$ values of retrocyclin-1 and RC-101 also differed significantly (p=0.012). FIG. 17 compares the activity of the retrocyclin peptides against four subtype A and four subtype C primary isolates. RC-101 was more active than retrocyclin-1 against both subtypes at each concentration tested. Table 2 shows the IC$_{50}$ concentrations of the individual subtype A and subtype C isolates. For statistical analysis, the results obtained with subtypes A and C were combined, and a value of 10 was assigned to any IC$_{50}$ value >10 µg/ml. With these practices, the IC$_{50}$ of retrocyclin-1 was 7.79±1.16 µg/ml (mean±SEM, n=8) and the IC$_{50}$ of RC-101 was 2.93±0.95 µg/ml (p<0.001).

Figure 18:
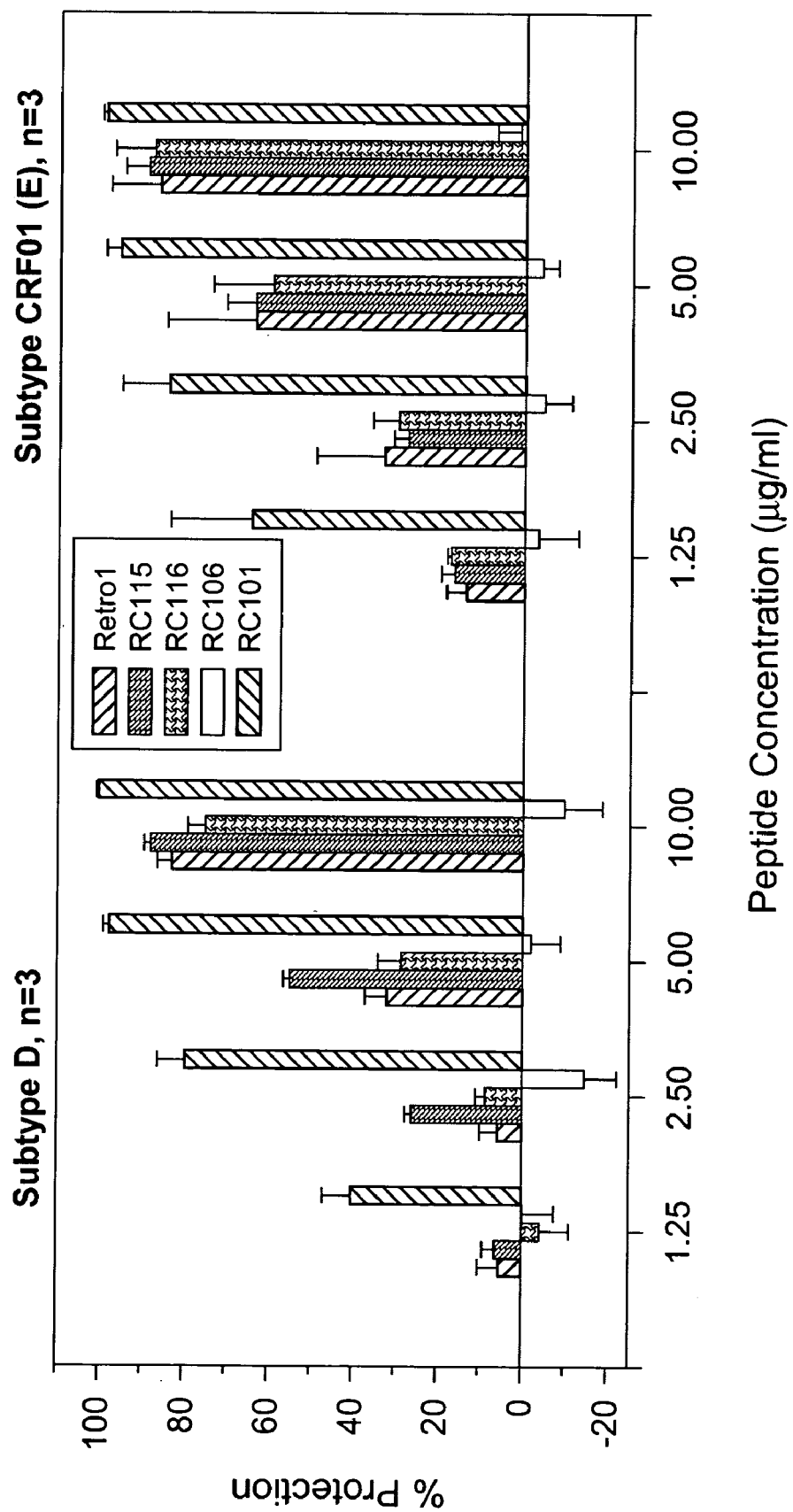
FIG. 18. Activity against subtype D and CRF01_AE isolates. Protective activity of the θ defensins was tested at four peptide concentrations: 1.25, 2.5, 5.0 and 10.0 µg/ml. The bars show mean % protection±S.E.M., n=3 for each subtype.
Figure 19:
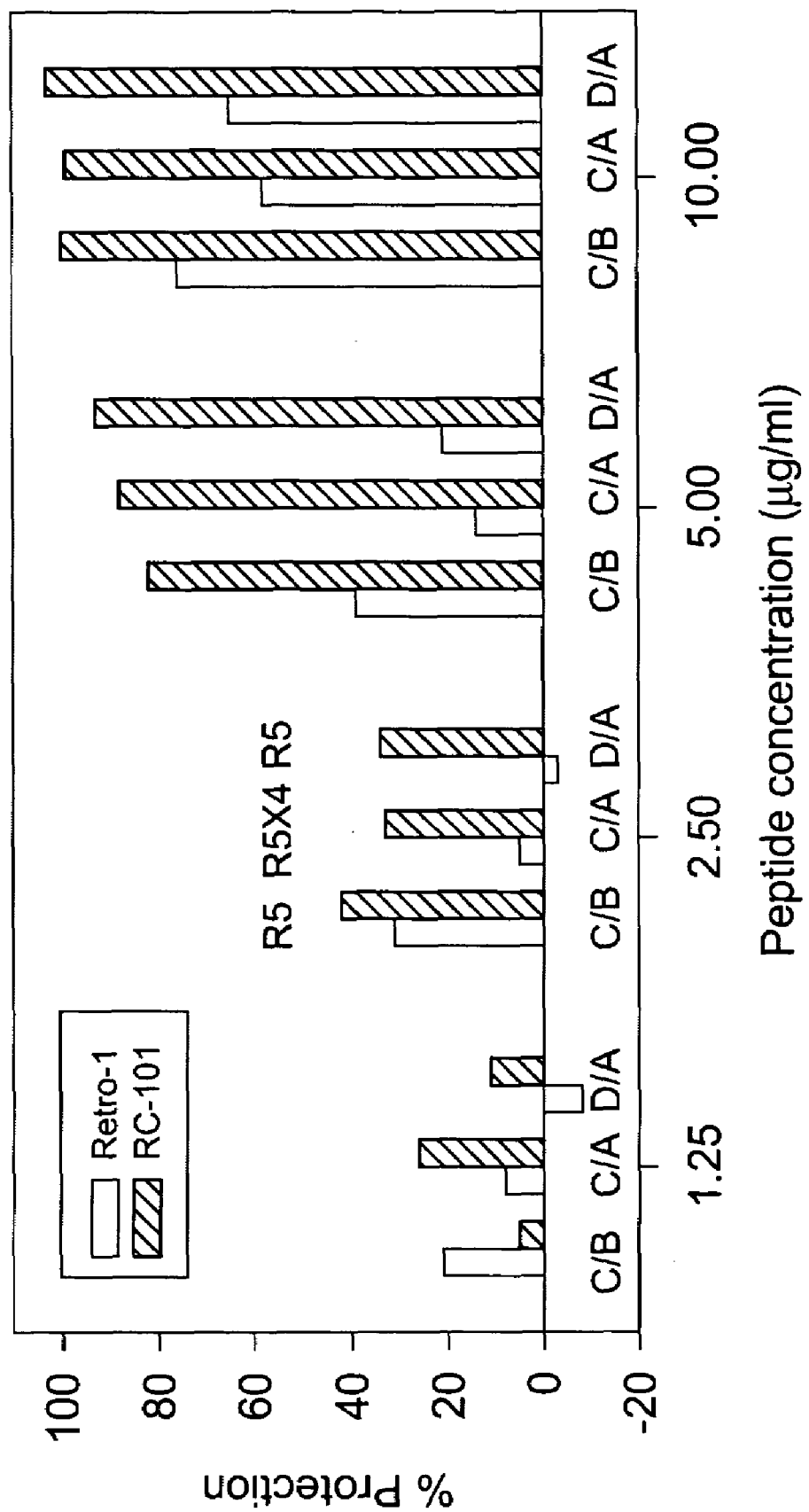
FIG. 19. Activity against three recombinant subtypes. Protective activity of the E defensins was tested at four peptide concentrations: 1.25, 2.5, 5.0 and 10.0 µg/ml. The subtypes appear beneath each set of bars. Their coreceptor specificity is shown above the second set of bars.

FIG. 18 compares the activity of these peptides against six additional primary HIV-1 isolates, three from subtype D and three circulating recombinant forms (CRF01_AE, formerly classified as subtype E). RC-101 was more active than retrocyclin-1 against the subtype D strains at 1.25 µg/ml (p=0.02), 2.5 µg/ml (p=0.004), 5 µg/ml (p=0.003) and 10 µg/ml (p=0.032). Analysis of subtype G and various recombinant viruses gave similar results, wherein RC-101 afforded greater protection than retrocyclin-1 (FIG. 19, Table 6).

Figure 20:
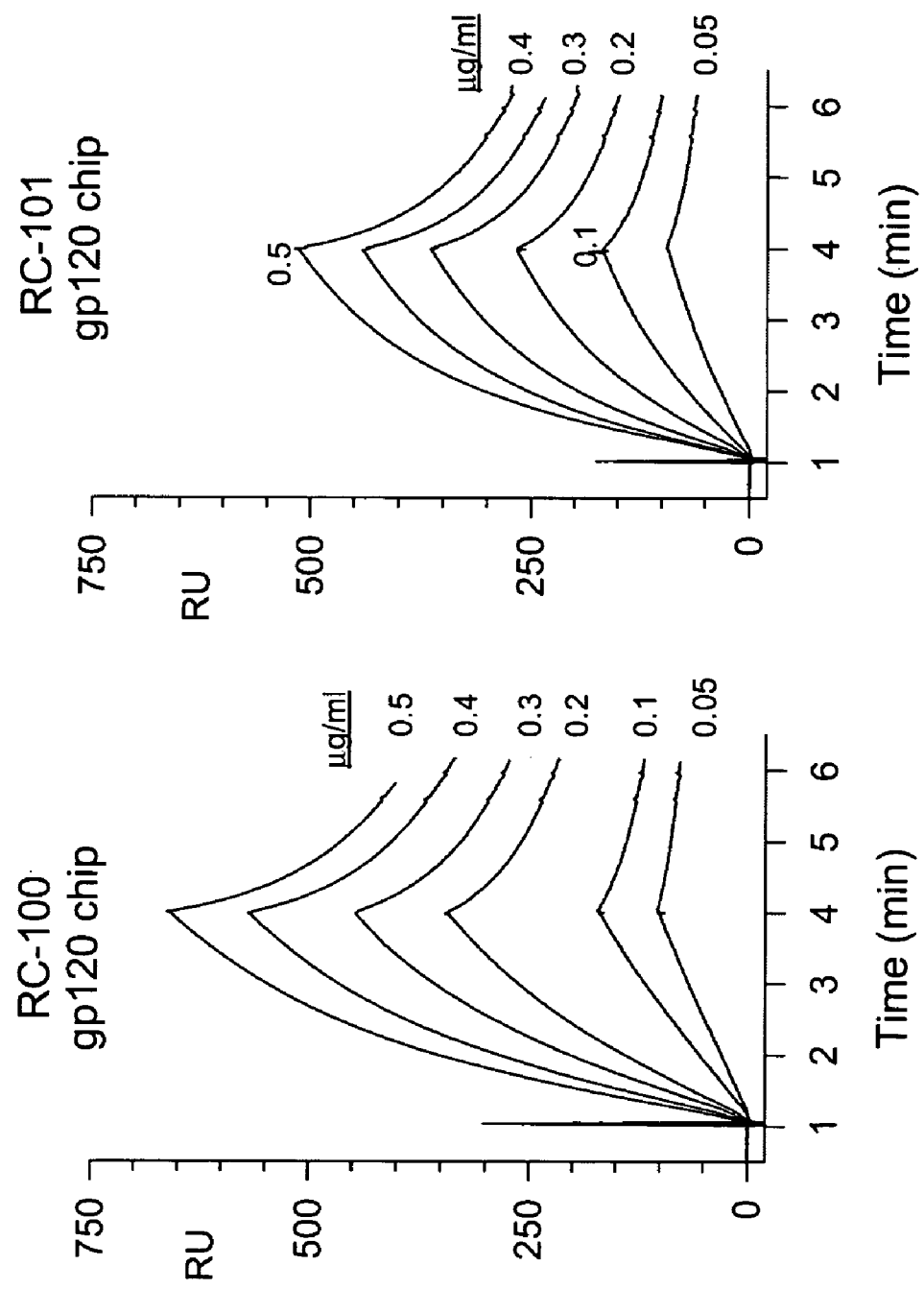
FIG. 20. Binding to gp120. These binding isotherms were measured by surface plasmon resonance, using a biosensor chip that contained immobilized, recombinant gp120. Various concentrations of RC-100 and RC-101 (0.05 to 0.5 µg/ml) flowed over the biosensor chip between minutes 1 to 4, to allow the "on rates" to be measured. At 4 minutes, the peptide-containing solutions were replaced by peptide-free medium, to ascertain the "off-rates."

We previously reported that the protection against HIV-1 afforded by retrocyclin-1 and its analogs was correlated to their binding to gp120 and CD4. In those experiments, biosensor chips containing immobilized gp120 or CD4 were perfused with a 1 µg/ml solution of the peptides, and binding was measured by surface plasmon resonance. When we compared binding by retrocyclin-1 and RC-101 in exactly the same manner, we saw very little difference between them. FIG. 20 compares the binding of lower concentrations of these peptides, ranging from 0.05 to 0.5 µg/ml, to immobilized gp120 LAV. From these binding isotherms, and from similar studies performed with biosensor chips containing immobilized gp120 BaL or CD4, the binding constants shown in Table 7 were obtained. RC-101 had a slightly higher affinity than retrocyclin-1 for both gp120 preparations, however, their respective KD values differed only by about 10% for gp120 LAV and by about 30% for gp120 BaL. No binding studies were performed with gp120 preparations derived from non-B HIV-1 subtypes. These would be of considerable interest, especially for subtype C, which required the highest peptide concentrations to achieve protection. We found no significant difference between retrocyclin-1 and RC-101 with respect to binding immobilized CD4 (Table 7).

TABLE 7

| Peptide | Receptor | k$_{on}$ | k$_{off}$ | K$_D$ |
|---|---|---|---|---|
| RC-100 | gp120(LAV) | 8.03 × 10$^4$ | 2.96 × 10$^{-3}$ | 35.4 nM |
| RC-101 | gp120(LAV) | 9.72 × 10$^4$ | 3.04 × 10$^{-3}$ | 31.2 nM |
| RC-100 | gp120(BaL) | 14.1 × 10$^4$ | 4.12 × 10$^{-3}$ | 29.2 nM |
| RC-101 | gp120(BaL) | 27.0 × 10$^4$ | 5.55 × 10$^{-3}$ | 20.5 nM |
| RC-100 | CD4 | 6.77 × 10$^4$ | 2.20 × 10$^{-3}$ | 31.0 nM |
| RC-101 | CD4 | 7.90 × 10$^4$ | 2.26 × 10$^{-3}$ | 28.6 nM |

Human leukocytes do not express θ-defensins. Instead, they contain four α-defensins (HNP 1, 2, 3 and 4) that collectively contain 17 arginine residues and no lysines. This lopsided ratio is noteworthy, because lysine is generally at least as abundant as arginine in most other peptides and proteins. The other α-defensins in mammalian neutrophils (PMNs) also show a marked preference for arginine over lysine. Collectively, the four rat α-defensins (Rat NPs 1-4) contain 28 arginines and no lysines, and the six rabbit α-defensins have 47 arginines and only 2 lysines. Even the bovine neutrophil's α-defensins (BNBDs) display a marked excess of arginines over lysines, since BNBDs 1-10 collectively contain 71 arginines and only 6 lysines. Thus, whereas the replacement of an arginine residue with a lysine would be considered conservative by chemists, evolution strongly favored arginines in selecting the mammalian leukocyte defensins. No such selection bias is evident in most mammalian epithelial cell β-defensins. Collectively, human beta defensins 1-3 and murine beta-defensins 1-3 contain 30 lysines and 20 arginines.

Because the θ-defensin genes arose via mutation of pre-existing myeloid α-defensin genes, θ-defensin peptides are also arginine-rich and lysine poor. In a recent study that examined 16 primate θ-defensin genes from nine primate species, we found that the nonapeptide domains included in θ-defensins contained 37 arginines and no lysines. Thus, while the difference between RC-100 and RC-101 might seem chemically conservative, peptides like RC-101 are not likely to be generated in vivo by evolutionary processes based on random mutation and natural selection.

Both lysine and arginine residues carry a positive charge at the end of a flexible, long, locally hydrophobic side chain. Consequently, both can form salt bridges with negatively charged amino acids, sugars (e.g., sialic acids) and other (poly)anionic molecules (e.g., nucleic acids). Whereas the rigid guanidinium group of arginine contains five potential hydrogen bond donors, the nonplanar ε-amino group of lysine has but two of them. In many studies, replacing an arginine with lysine (or vice versa) has affected function—sometimes radically.

This is well illustrated by two porcine antimicrobial peptides: protegrin PG-1 and tritrpticin, a 13-residue peptide rich in tryptophan, proline and arginine. Replacing the arginines of tritrpticin with lysines enhanced its antimicrobial activity and reduced its hemolytic effects. Protegrin (PG)-1 is a noncyclic, arginine-rich β-hairpin antimicrobial peptide whose structure is generally similar to that of θ-defensins. Substituting lysine for arginine in PG-1 caused up to a four-fold increase in its activity against Gram-negative bacteria. It is noteworthy that the subtype A and C isolates in our panel were considerably more resistant to retrocyclin-1 than were the other subtypes. Overall, 6 of the 8 subtype C isolates and 3 of the 6 subtype A strains had $IC_{50}$ values above 10 µg retrocyclin-1/ml. In contrast, only 1 of the 30 other primary isolates listed in Table 6 had an $IC_{50}$ of this magnitude. To compare the $IC_{50}$ values of subtypes B and C by nonparametric statistics, we assigned a value of 10 µg/ml for 12 each $IC_{50}$ value above 10 µg/ml. A Mann-Whitney Sign Rank test found a statistically significant difference (P exact=0.04) between the respective $IC_{50}$ values.

The activity of retrocyclin-1 analogs against HIV-1 strains JR-CSF and IIIB (both of subtype B) correlated with binding of these peptides to gp120 from HIV-1 LAV (the prototype subtype B isolate). In this study, we found no significant differences in how retrocyclin-1 and RC-101 bound immobilized gp120 (FIG. 20 and Table 7). However, all of our binding studies to date have been conducted with recombinant gp120 that was ultimately derived from subtype B strains. The C2-V3 region of gp120 from subtype C isolates typically lacks a potential N-glycosylation site that is present in other HIV-1 subtypes, and most subtype A variants also lack one or more N-linked glycans in this region. These affected sites are in close proximity to the bottom of the V3 loop, a region that plays a major role in viral tropism and co-receptor usage.

Example 5

The sequence and activity of additional retrocyclin-related peptides are shown in Table 8.

TABLE 8

| Identifier | Alternative Name | Mass | Hemagglutination seen at a concentration of: | Sequence (linear) |
|---|---|---|---|---|
| RC100 | Retrocyclin-1 | 1918.4 | 6–12.5 µg/ml and above | GICRC ICGRG ICRCI CGR (SEQ ID NO: 1) |
| RC100b | Retrocyclin-2 | 2017.6 | 12.5 or 25 µg/ml and above | GICRC ICGRR ICRCI CGR (SEQ ID NO: 140) |
| RC101 | RC101 | 1890.4 | None @ 200 µg/ml | GICRC ICGKG ICRCI CGR (SEQ ID NO: 2) |
| RC112 | Enantio-retro-1 | 1918.4 | 50 µg/ml | [All D] GICRC ICGRG ICRCI CGR (SEQ ID NO: 1) |
| RC113 | Enantio-RC101 | 1890.4 | 50 µg/ml | [All D] GICRC ICGKG ICRCI CGR (SEQ ID NO: 2) |
| RC114 | RC101/103 hybrid | 1940.5 | 200 µg/ml (None seen @ 150 µg/ml) | GICRC ICGKG ICRCY CGR (SEQ ID NO: 126) |
| RC119 | R→K Retrocyclin-1 | 1846.4 | 50 µg/ml | GICKC ICGKG ICKCI CGR (SEQ ID NO: 127) |
| RC123A | Retrocyclin 2A | 1989.6 | 50 µg/ml | GICRC ICGKR ICRCI CGR (SEQ ID NO: 128) |
| RC123B | Retrocyclin 2B | 1961.5 | 6.25 µg/ml and above | GICRC ICGKK ICRCI CGR (SEQ ID NO: 129) |
| RC123C | Retrocyclin 2C | 1989.6 | 50 µg/ml | GICRC ICGRK ICRCI CGR (SEQ ID NO: 130) |
| RC123D | Retrocyclin 2D | 1989.6 | 50 µg/ml | GICRC ICGRR ICKCI CGR (SEQ ID NO: 131) |
| RC123E | Retrocyclin 2E | 1989.6 | 25 µg/ml and above | GICKC ICGRR ICRCI CGR (SEQ ID NO: 132) |
| RC123F | Retrocyclin 2F | 1989.6 | 25 and 50 µg/ml | GICRC ICGRR ICRCI CGK (SEQ ID NO: 133) |
| Orang-2 | — | 1989.5 | NT | GVCRC ICGRG VCRCI CRR (SEQ ID NO: 134) |
| Orang-3 | — | | NT | GVCRC ICGRG VCRCI CGR (SEQ ID NO: 135) |

The table shows lysine containing variants of retrocyclin. Thirteen of these peptides were tested for their ability to cause hemagglutination (clumping of red cells). Hemagglutination is a common property of lectins, so its occurrence is not surprising since we have reported that retrocyclins are lectins. Several of the lysine containing peptides showed much less hemagglutination than retrocyclin—including RC101 and RC114. This is a desirable property for systemic administration. Several of the other lysin-containing retrocyclin derivatives also showed less hemagglutination than retrocyclins 1 or 2, as shown in the table.

Figure 22:
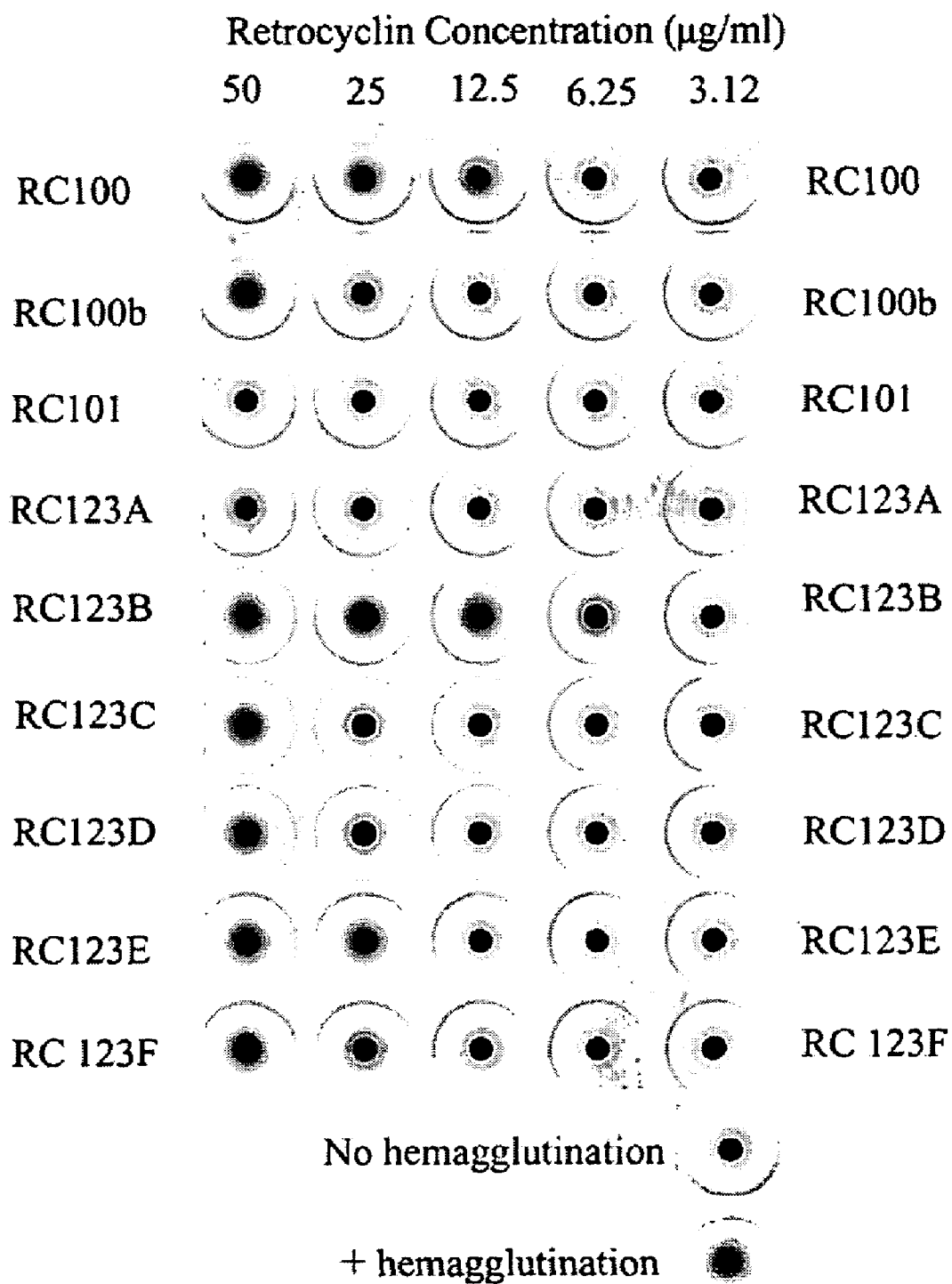
FIG. 22 shows the effect of various retrocyclins on hemagglutination.

Hemagglutination was tested by adding the stated concentration of peptide to a well comprising red blood cells (shown in FIG. 22). When the RBC are agglutinated, they clump together and settle rapidly and form a diffuse circle covering much of the bottom of the well. In the absence of agglutination, they settle more slowly and form a compact red button in the center of the well.

Sequences of retrocyclin-related peptides that were synthesized and either tested for activity against HIV-1 (see FIGS. 21A and 21B) and/or for their ability to cause human red blood cells to hemagglutinate or both. NT signifies not tested. Linear sequences appear in the table, but all peptides were cyclic and contained three intramolecular disulfide bonds. Hemagglutination of washed human red blood cells was tested in PBS, at peptide concentrations of 50, 25, 12.5 6.25 and 3.12 µg/ml. The lowest concentrations that caused hemagglutination are shown. Peptide concentrations were determined by amino acid analysis or by AUC (area under the curve) RP-HPLC analysis with reference to amino-acid analyzed standards. RC101, RC112 (enantio-retrocyclin-1), RC113, RC123A and RC123C all caused less hemagglutination than retrocyclin-1 or retrocyclin-2.

Figure 21A:
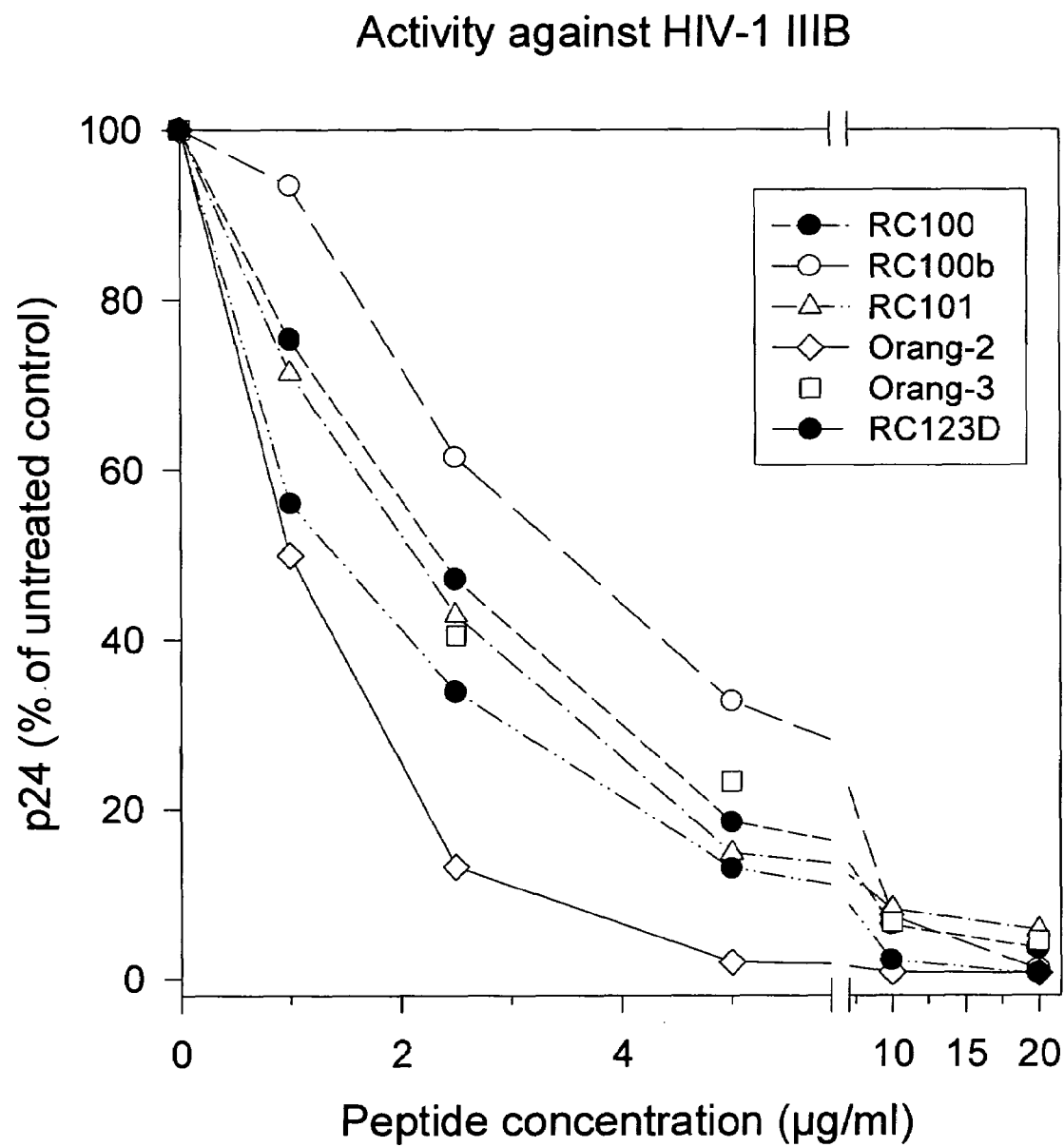
FIG. 21A-21B. Activity of theta-defensins against HIV-1 BAL; and HIV-1 IIIB.
Figure 21B:
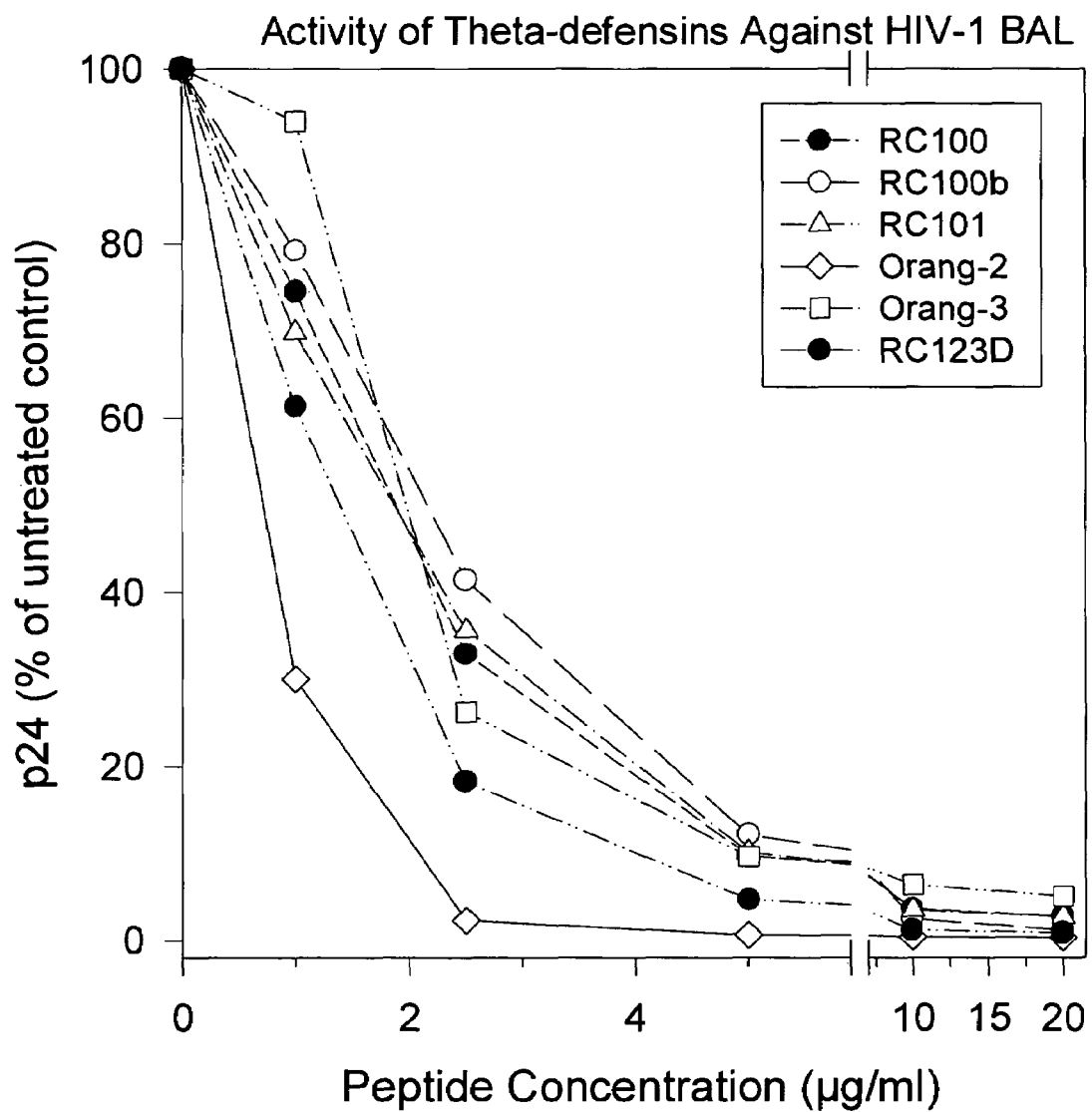

The data shown in FIGS. 21A and 21B illustrate the activity of these retrocyclin-related peptides against two different strains of HIV-1, BAL and IIIB. Interestingly, orang-2 appeared more potent than retrocyclins 1 and 2 and RC101 against both strains. BAL and IIIB are widely studied, laboratory adapted strains of HIV.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising the amino acid sequence set forth in SEQ ID NO:1; SEQ ID NO:3; SEQ ID NO:4; SEQ ID NO:5; or SEQ ID NO:6.

2. The isolated retrocyclin peptide according to claim 1, wherein said peptide is linear.

3. The isolated retrocyclin peptide according to claim 1, wherein said peptide is circular.

4. A polypeptide according to claim 1, and a pharmaceutically acceptable excipient.

5. An isolated retrocyclin peptide, wherein said peptide is two linked nonapeptides, wherein one said nonapeptide is SEQ ID NO:19 comprising a lysine or lysine analog substitution at residue 6, and one said nonapeptide is selected from the group consisting of SEQ ID NO:19 to SEQ ID NO:64; and SEQ ID NO:74 to SEQ ID NO:119.

6. The isolated retrocyclin according to claim 5, and a pharmaceutically acceptable excipient.

7. A polypeptide comprising the amino acid sequence set forth in SEQ ID NO:2.

8. A polypeptide according to claim 7, and a pharmaceutically acceptable excipient.

* * * * *

UNITED STATES PATENT AND TRADEMARK OFFICE
CERTIFICATE OF CORRECTION

PATENT NO. : 7,314,858 B2
APPLICATION NO. : 10/982145
DATED : January 1, 2008
INVENTOR(S) : Robert I. Lehrer It is certified that error appears in the above-identified patent and that said Letters Patent is hereby corrected as shown below:

- Col 97 Claim 2 line 44: Delete the word "retrocyclin".
- Col 97 Claim 3 line 46: Delete the word "retrocyclin".

Signed and Sealed this

Twenty-fourth Day of June, 2008

JON W. DUDAS
*Director of the United States Patent and Trademark Office*

UNITED STATES PATENT AND TRADEMARK OFFICE
CERTIFICATE OF CORRECTION

PATENT NO.      : 7,314,858 B2
APPLICATION NO. : 10/982145
DATED           : January 1, 2008
INVENTOR(S)     : Robert I. Lehrer It is certified that error appears in the above-identified patent and that said Letters Patent is hereby corrected as shown below:

- Column 1, line 6: please delete "fights" and insert --rights--, so that the sentence reads as follows:

The Government has certain rights in this invention.

Signed and Sealed this

Twenty-seventh Day of October, 2009

David J. Kappos
*Director of the United States Patent and Trademark Office*

SEQUENCE LISTING

```
<160> NUMBER OF SEQ ID NOS: 135

<210> SEQ ID NO 1
<211> LENGTH: 18
<212> TYPE: PRT
<213> ORGANISM: Homo sapiens

<400> SEQUENCE: 1

Gly Ile Cys Arg Cys Ile Cys Gly Arg Gly Ile Cys Arg Cys Ile Cys
1               5                   10                  15

Gly Arg

<210> SEQ ID NO 2
<211> LENGTH: 18
<212> TYPE: PRT
<213> ORGANISM: Artificial Sequence
<220> FEATURE:
<223> OTHER INFORMATION: synthetic variant

<400> SEQUENCE: 2

Gly Ile Cys Arg Cys Ile Cys Gly Lys Gly Ile Cys Arg Cys Ile Cys
1               5                   10                  15

Gly Arg

<210> SEQ ID NO 3
<211> LENGTH: 18
<212> TYPE: PRT
<213> ORGANISM: Artificial Sequence
<220> FEATURE:
<223> OTHER INFORMATION: synthetic variant

<400> SEQUENCE: 3

Gly Ile Cys Arg Cys Tyr Cys Gly Arg Gly Ile Cys Arg Cys Ile Cys
1               5                   10                  15
```

Gly Arg

<210> SEQ ID NO 4
<211> LENGTH: 18
<212> TYPE: PRT
<213> ORGANISM: Artificial Sequence
<220> FEATURE:
<223> OTHER INFORMATION: synthetic variant

<400> SEQUENCE: 4

Gly Ile Cys Arg Cys Ile Cys Gly Arg Gly Ile Cys Arg Cys Tyr Cys
 1               5                  10                  15
Gly Arg

<210> SEQ ID NO 5
<211> LENGTH: 18
<212> TYPE: PRT
<213> ORGANISM: Artificial Sequence
<220> FEATURE:
<223> OTHER INFORMATION: synthetic variant

<400> SEQUENCE: 5

Gly Tyr Cys Arg Cys Ile Cys Gly Arg Gly Ile Cys Arg Cys Ile Cys
 1               5                  10                  15
Gly Arg

<210> SEQ ID NO 6
<211> LENGTH: 18
<212> TYPE: PRT
<213> ORGANISM: Artificial Sequence
<220> FEATURE:
<223> OTHER INFORMATION: synthetic variant

<400> SEQUENCE: 6

Gly Ile Cys Arg Cys Ile Cys Gly Arg Gly Tyr Cys Arg Cys Ile Cys
 1               5                  10                  15
Gly Arg

<210> SEQ ID NO 7
<211> LENGTH: 18
<212> TYPE: PRT
<213> ORGANISM: Artificial Sequence
<220> FEATURE:
<223> OTHER INFORMATION: synthetic variant

<400> SEQUENCE: 7

Gly Ile Cys Tyr Cys Ile Cys Gly Arg Gly Ile Cys Arg Cys Ile Cys
 1               5                  10                  15
Gly Arg

<210> SEQ ID NO 8
<211> LENGTH: 18
<212> TYPE: PRT
<213> ORGANISM: Artificial Sequence
<220> FEATURE:
<223> OTHER INFORMATION: synthetic variant

<400> SEQUENCE: 8

Gly Ile Cys Ile Cys Ile Cys Gly Tyr Gly Ile Cys Arg Cys Ile Cys
 1               5                  10                  15
Gly Arg

```
<210> SEQ ID NO 9
<211> LENGTH: 18
<212> TYPE: PRT
<213> ORGANISM: Artificial Sequence
<220> FEATURE:
<223> OTHER INFORMATION: synthetic variant

<400> SEQUENCE: 9

Gly Ile Cys Ile Cys Ile Cys Gly Arg Gly Ile Cys Tyr Cys Ile Cys
 1               5                  10                  15

Gly Arg

<210> SEQ ID NO 10
<211> LENGTH: 18
<212> TYPE: PRT
<213> ORGANISM: Artificial Sequence
<220> FEATURE:
<223> OTHER INFORMATION: synthetic variant

<400> SEQUENCE: 10

Arg Gly Cys Ile Cys Arg Cys Ile Gly Arg Gly Cys Ile Cys Arg Cys
 1               5                  10                  15

Ile Gly

<210> SEQ ID NO 11
<211> LENGTH: 496
<212> TYPE: DNA
<213> ORGANISM: Homo sapiens
<220> FEATURE:
<221> NAME/KEY: CDS
<222> LOCATION: (124)...(304)
<223> OTHER INFORMATION: retrocyclin

<400> SEQUENCE: 11
ggagacccgg gacagaggac tgctgtctgc cctccctctt cactctgcct accttgagga      60
tctgtcaccc cagccatgag gaccttcgcc ctcctcactg ccatgcttct cctggtggcc     120 ctg tag gct cag gcg gag cca ctt cag gca aga gct gat gaa gct gca       168
  *  Ala Gln Ala Glu Pro Leu Gln Ala Arg Ala Asp Glu Ala Ala
       1               5                  10 gcc cag gag cag cct gga gca gat gat cag gaa atg gct cat gcc ttt       216
Ala Gln Glu Gln Pro Gly Ala Asp Asp Gln Glu Met Ala His Ala Phe
 15                  20                  25                  30 aca tgg cat gaa agt gcc gct ctt ccg ctt tca gac tca gcg aga ggc       264
Thr Trp His Glu Ser Ala Ala Leu Pro Leu Ser Asp Ser Ala Arg Gly
                 35                  40                  45 ttg agg tgc att tgc gga aga gga att tgc cgt ttg tta t aacgtcgctt      314
Leu Arg Cys Ile Cys Gly Arg Gly Ile Cys Arg Leu Leu
             50                  55 tgggtcctgc gcctttcgtg gtacactcca ccggatctgc tgccgctgag cttgcagaat     374
caagaaacat aagctcagaa tttactttga gagttaaaag aaattcttgt tactcctgta     434
ccttgtcctc catttccttt tctcatccaa aataaatacc ttgttgcaag atttctctct     494
tt                                                                    496

<210> SEQ ID NO 12
<211> LENGTH: 59
<212> TYPE: PRT
<213> ORGANISM: Homo sapiens

<400> SEQUENCE: 12

Ala Gln Ala Glu Pro Leu Gln Ala Arg Ala Asp Glu Ala Ala Ala Gln
 1               5                  10                  15
```

```
Glu Gln Pro Gly Ala Asp Asp Gln Glu Met Ala His Ala Phe Thr Trp
         20                  25                  30

His Glu Ser Ala Ala Leu Pro Leu Ser Asp Ser Ala Arg Gly Leu Arg
     35                  40                  45

Cys Ile Cys Gly Arg Gly Ile Cys Arg Leu Leu
 50                  55
```

<210> SEQ ID NO 13
<211> LENGTH: 97
<212> TYPE: PRT
<213> ORGANISM: Homo sapiens
<220> FEATURE:
<221> NAME/KEY: PEPTIDE
<222> LOCATION: (1)...(97)
<223> OTHER INFORMATION: Human defensin 4

<400> SEQUENCE: 13

```
Met Arg Ile Ile Ala Leu Leu Ala Ala Ile Leu Leu Val Ala Leu Gln
 1               5                  10                  15

Val Arg Ala Gly Pro Leu Gln Ala Arg Gly Asp Glu Ala Pro Gly Gln
         20                  25                  30

Glu Gln Arg Gly Pro Glu Asp Gln Asp Ile Ser Ile Ser Phe Ala Trp
     35                  40                  45

Asp Lys Ser Ser Ala Leu Gln Val Ser Gly Ser Thr Arg Gly Met Val
 50                  55                  60

Cys Ser Cys Arg Leu Val Phe Cys Arg Arg Thr Glu Leu Arg Val Gly
 65                  70                  75                  80

Asn Cys Leu Ile Gly Gly Val Ser Phe Thr Tyr Cys Cys Thr Arg Val
                 85                  90                  95

Asp
```

<210> SEQ ID NO 14
<211> LENGTH: 500
<212> TYPE: DNA
<213> ORGANISM: Macaca mulatta
<220> FEATURE:
<221> NAME/KEY: CDS
<222> LOCATION: (95)...(325)
<223> OTHER INFORMATION: theta defensin 1A precursor
<220> FEATURE:
<221> NAME/KEY: sig_peptide
<222> LOCATION: (95)...(154)
<220> FEATURE:
<221> NAME/KEY: mat_peptide
<222> LOCATION: (287)...(313)
<223> OTHER INFORMATION: ligated to RTD1b in head-to-tail orientation to
      form the cyclic octadecapeptide RTD1; RTD1 is
      stabilized by three intramolecular disulfides

<400> SEQUENCE: 14

```
gacggctgct gttgctacag gagacccagg acagaggact gctgtctgca ctctctcttc      60
actctgccta acttgaggat ctgtcactcc agcc atg agg acc ttc gcc ctc ctc     115
                                     Met Arg Thr Phe Ala Leu Leu
                                         -20                 -15 acc gcc atg ctt ctc ctg gtg gcc ctg cac gct cag gca gag gca cgt       163
Thr Ala Met Leu Leu Leu Val Ala Leu His Ala Gln Ala Glu Ala Arg
            -10                  -5                   1 cag gca aga gct gat gaa gct gcc gcc cag cag cag cct gga aca gat       211
Gln Ala Arg Ala Asp Glu Ala Ala Ala Gln Gln Gln Pro Gly Thr Asp
     5                  10                  15 gat cag gga atg gct cat tcc ttt aca tgg cct gaa aac gcc gct ctt       259
Asp Gln Gly Met Ala His Ser Phe Thr Trp Pro Glu Asn Ala Ala Leu
```

```
           20                  25                  30                  35 cca ctt tca gag tca gcg aaa ggc ttg agg tgc att tgc aca cga gga        307
Pro Leu Ser Glu Ser Ala Lys Gly Leu Arg Cys Ile Cys Thr Arg Gly
                40                  45                  50 ttc tgc cgt ttg tta taa tgtcaccttg ggtcctgcgc ttttcgtggt              355
Phe Cys Arg Leu Leu *
                55 tgactccacc ggatctgctg ccgctgagct tccagaatca agaaaaatat gctcagaagt     415 tactttgaga gttaaaagaa attcttgcta ctgctgtacc ttctcctcag tttccttttc     475 tcatcccaaa taaataccct atcgc                                           500

<210> SEQ ID NO 15
<211> LENGTH: 76
<212> TYPE: PRT
<213> ORGANISM: Macaca mulatta
<220> FEATURE:
<221> NAME/KEY: SIGNAL
<222> LOCATION: (1)...(20)

<400> SEQUENCE: 15

Met Arg Thr Phe Ala Leu Leu Thr Ala Met Leu Leu Val Ala Leu
-20                 -15                 -10                 -5

His Ala Gln Ala Glu Ala Arg Gln Ala Arg Ala Asp Glu Ala Ala Ala
                 1               5                  10

Gln Gln Gln Pro Gly Thr Asp Asp Gln Gly Met Ala His Ser Phe Thr
            15                  20                  25

Trp Pro Glu Asn Ala Ala Leu Pro Leu Ser Glu Ser Ala Lys Gly Leu
        30                  35                  40

Arg Cys Ile Cys Thr Arg Gly Phe Cys Arg Leu Leu
45                  50                  55

<210> SEQ ID NO 16
<211> LENGTH: 495
<212> TYPE: DNA
<213> ORGANISM: Macaca mulatta
<220> FEATURE:
<221> NAME/KEY: CDS
<222> LOCATION: (90)...(320)
<223> OTHER INFORMATION: theta defensin 1b precursor
<220> FEATURE:
<221> NAME/KEY: sig_peptide
<222> LOCATION: (90)...(149)
<220> FEATURE:
<221> NAME/KEY: mat_peptide
<222> LOCATION: (282)...(308)
<223> OTHER INFORMATION: ligated to RTD1a in head-to-tail orientation to
      form the cyclic octadecapeptide RTD1; RTD1 is
      stabilized by three intramolecular disulfides

<400> SEQUENCE: 16
gaccgctgct cttgctacag gagacccggg acagaggact gctgtctgcc ctctctcttc      60
actctgccta acttgaggat ctgccagcc atg agg acc ttc gcc ctc ctc acc       113
                                 Met Arg Thr Phe Ala Leu Leu Thr
                                 -20                 -15 gcc atg ctt ctc ctg gtg gcc ctg cac gct cag gca gag gca cgt cag       161
Ala Met Leu Leu Leu Val Ala Leu His Ala Gln Ala Glu Ala Arg Gln
        -10                 -5                   1 gca aga gct gat gaa gct gcc gcc cag cag cag cct gga gca gat gat       209
Ala Arg Ala Asp Glu Ala Ala Ala Gln Gln Gln Pro Gly Ala Asp Asp
 5                  10                  15                  20 cag gga atg gct cat tcc ttt aca cgg cct gaa aac gcc gct ctt ccg       257
Gln Gly Met Ala His Ser Phe Thr Arg Pro Glu Asn Ala Ala Leu Pro
```

```
                     25                  30                  35
ctt tca gag tca gcg aga ggc ttg agg tgc ctt tgc aga cga gga gtt      305
Leu Ser Glu Ser Ala Arg Gly Leu Arg Cys Leu Cys Arg Arg Gly Val
                40                  45                  50 tgc caa ctg tta taa aggcgtttgg ggtcctgcgc ttttcgtggt tgactctgcc      360
Cys Gln Leu Leu *
            55 ggatctgctg ccgctgagct tccagaatca agaaaaatac gctcagaagt tactttgaga    420 gttgaaagaa attcctgtta ctcctgtacc ttgtcctcaa tttccttttc tcatcccaaa    480 taaataccct ctcgc                                                     495

<210> SEQ ID NO 17
<211> LENGTH: 76
<212> TYPE: PRT
<213> ORGANISM: Macaca mulatta
<220> FEATURE:
<221> NAME/KEY: SIGNAL
<222> LOCATION: (1)...(20)

<400> SEQUENCE: 17

Met Arg Thr Phe Ala Leu Leu Thr Ala Met Leu Leu Val Ala Leu
-20                 -15                 -10                 -5

His Ala Gln Ala Glu Ala Arg Gln Ala Arg Ala Asp Glu Ala Ala Ala
                 1               5                  10

Gln Gln Gln Pro Gly Ala Asp Asp Gln Gly Met Ala His Ser Phe Thr
            15                  20                  25

Arg Pro Glu Asn Ala Ala Leu Pro Leu Ser Glu Ser Ala Arg Gly Leu
        30                  35                  40

Arg Cys Leu Cys Arg Arg Gly Val Cys Gln Leu Leu
    45                  50                  55

<210> SEQ ID NO 18
<211> LENGTH: 54
<212> TYPE: DNA
<213> ORGANISM: Artificial Sequence
<220> FEATURE:
<223> OTHER INFORMATION: synthetic sequence

<400> SEQUENCE: 18
aggtgcattt gcggaagagg aatttgcagg tgcatttgcg aagaggaat ttgc           54

<210> SEQ ID NO 19
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 19

Arg Cys Ile Cys Gly Arg Gly Ile Cys
  1               5

<210> SEQ ID NO 20
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 20
```

Arg Cys Leu Cys Gly Arg Gly Ile Cys
1               5

<210> SEQ ID NO 21
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 21

Arg Cys Ile Cys Arg Arg Gly Ile Cys
1               5

<210> SEQ ID NO 22
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 22

Arg Cys Ile Cys Thr Arg Gly Ile Cys
1               5

<210> SEQ ID NO 23
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 23

Arg Cys Ile Cys Val Arg Gly Ile Cys
1               5

<210> SEQ ID NO 24
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 24

Arg Cys Ile Cys Gly Leu Gly Ile Cys
1               5

<210> SEQ ID NO 25
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 25

Arg Cys Ile Cys Gly Arg Gly Val Cys
1               5

<210> SEQ ID NO 26
<211> LENGTH: 9
<212> TYPE: PRT
<213> ORGANISM: Artificial Sequence
<220> FEATURE:

```
<223> OTHER INFORMATION: generated by replacement of variants in
      consensus sequence

<400> SEQUENCE: 26

Arg Cys Ile Cys Gly Arg Gly Phe Cys
 1               5

<210> SEQ ID NO 27
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 27

Arg Cys Leu Cys Arg Arg Gly Val Cys
 1               5

<210> SEQ ID NO 28
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 28

Arg Cys Leu Cys Thr Arg Gly Ile Cys
 1               5

<210> SEQ ID NO 29
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 29

Arg Cys Leu Cys Val Arg Gly Ile Cys
 1               5

<210> SEQ ID NO 30
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 30

Arg Cys Leu Cys Gly Leu Gly Val Cys
 1               5

<210> SEQ ID NO 31
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 31

Arg Cys Leu Cys Gly Arg Gly Val Cys
 1               5
```

<210> SEQ ID NO 32
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 32

Arg Cys Leu Cys Gly Arg Gly Phe Cys
 1               5

<210> SEQ ID NO 33
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 33

Arg Cys Ile Cys Arg Arg Gly Val Cys
 1               5

<210> SEQ ID NO 34
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 34

Arg Cys Ile Cys Arg Arg Gly Phe Cys
 1               5

<210> SEQ ID NO 35
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 35

Arg Cys Ile Cys Thr Arg Gly Val Cys
 1               5

<210> SEQ ID NO 36
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 36

Arg Cys Ile Cys Thr Arg Gly Phe Cys
 1               5

<210> SEQ ID NO 37
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 37

```
Arg Cys Ile Cys Thr Leu Gly Ile Cys
 1               5
```

<210> SEQ ID NO 38
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 38

```
Arg Cys Ile Cys Val Leu Gly Phe Cys
 1               5
```

<210> SEQ ID NO 39
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 39

```
Arg Cys Ile Cys Arg Leu Gly Ile Cys
 1               5
```

<210> SEQ ID NO 40
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 40

```
Arg Cys Ile Cys Val Arg Gly Val Cys
 1               5
```

<210> SEQ ID NO 41
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 41

```
Arg Cys Ile Cys Gly Arg Gly Phe Cys
 1               5
```

<210> SEQ ID NO 42
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 42

```
Arg Cys Ile Cys Gly Leu Gly Phe Cys
 1               5
```

<210> SEQ ID NO 43
<211> LENGTH: 9
<212> TYPE: PRT
<213> ORGANISM: Artificial Sequence

```
<220> FEATURE:
<223> OTHER INFORMATION: generated by replacement of variants in
      consensus sequence

<400> SEQUENCE: 43

Arg Cys Ile Cys Gly Leu Gly Val Cys
 1               5

<210> SEQ ID NO 44
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 44

Arg Cys Leu Cys Arg Leu Gly Ile Cys
 1               5

<210> SEQ ID NO 45
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 45

Arg Cys Leu Cys Arg Arg Gly Val Cys
 1               5

<210> SEQ ID NO 46
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 46

Arg Cys Leu Cys Arg Arg Gly Phe Cys
 1               5

<210> SEQ ID NO 47
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 47

Arg Cys Leu Cys Thr Leu Gly Ile Cys
 1               5

<210> SEQ ID NO 48
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 48

Arg Cys Leu Cys Thr Arg Gly Val Cys
 1               5
```

<210> SEQ ID NO 49
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 49

Arg Cys Leu Cys Thr Arg Gly Phe Cys
 1               5

<210> SEQ ID NO 50
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 50

Arg Cys Leu Cys Val Leu Gly Ile Cys
 1               5

<210> SEQ ID NO 51
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 51

Arg Cys Leu Cys Val Arg Gly Val Cys
 1               5

<210> SEQ ID NO 52
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 52

Arg Cys Ile Cys Gly Arg Gly Ile Cys
 1               5

<210> SEQ ID NO 53
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 53

Arg Cys Ile Cys Arg Leu Gly Val Cys
 1               5

<210> SEQ ID NO 54
<211> LENGTH: 9
<212> TYPE: PRT
<213> ORGANISM: Artificial Sequence
<220> FEATURE:
<223> OTHER INFORMATION: generated by replacement of variants in
      consensus sequence

```
<400> SEQUENCE: 54

Arg Cys Ile Cys Arg Leu Gly Phe Cys
 1               5

<210> SEQ ID NO 55
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 55

Arg Cys Ile Cys Thr Leu Gly Val Cys
 1               5

<210> SEQ ID NO 56
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 56

Arg Cys Ile Cys Thr Leu Gly Phe Cys
 1               5

<210> SEQ ID NO 57
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 57

Arg Cys Ile Cys Val Leu Gly Val Cys
 1               5

<210> SEQ ID NO 58
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 58

Arg Cys Ile Cys Val Leu Gly Phe Cys
 1               5

<210> SEQ ID NO 59
<211> LENGTH: 9
<212> TYPE: PRT
<213> ORGANISM: Artificial Sequence
<220> FEATURE:
<223> OTHER INFORMATION: generated by replacement of variants in
      consensus sequence

<400> SEQUENCE: 59

Arg Cys Leu Cys Gly Leu Gly Val Cys
 1               5

<210> SEQ ID NO 60
<211> LENGTH: 9
<212> TYPE: PRT
```

```
<213> ORGANISM: Artificial Sequence
<220> FEATURE:
<223> OTHER INFORMATION: generated by replacement of variants in

```
Ala Ala Ala Gln Glu Gln Pro Gly Ala Asp Asp Gln Glu Met Ala His
            35                  40                  45

Ala Phe Thr Trp His Glu Ser Ala Ala Leu Pro Leu Ser Asp Ser Ala
 50                  55                  60

Arg Gly Leu Arg Cys Ile Cys Gly Arg Gly Ile Cys Arg Leu Leu Arg
 65                  70                  75                  80

Arg Phe Gly Ser Cys Ala Phe Arg Gly Thr Leu His Arg Ile Cys Cys
                 85                  90                  95

Arg Ala Cys Arg Ile Lys Lys His Lys Leu Arg Ile Tyr Phe Glu Ser
                100                 105                 110

Lys Lys Phe Leu Leu Leu Leu Tyr Leu Val Leu His Phe Leu Phe Ser
            115                 120                 125

Ser Lys Ile Asn Thr Leu Leu Gln Asp Phe Ser Leu
            130                 135                 140
```

<210> SEQ ID NO 66
<211> LENGTH: 140
<212> TYPE: PRT
<213> ORGANISM: Orangutan

<400> SEQUENCE: 66

```
Val Thr Pro Ala Met Arg Thr Phe Ala Leu Leu Ala Ala Met Leu Leu
 1               5                  10                  15

Leu Val Ala Leu Ala Glu Ala Glu Pro Leu Gln Ala Arg Ala Asp Glu
            20                  25                  30

Thr Ala Ala Gln Glu Gln Pro Gly Ala Asp Asp Gln Glu Met Ala His
            35                  40                  45

Ala Phe Thr Trp Asp Glu Ser Ala Thr Leu Pro Leu Ser Asp Ser Ala
 50                  55                  60

Arg Gly Leu Arg Cys Ile Cys Arg Arg Gly Val Cys Arg Phe Leu Arg
 65                  70                  75                  80

His Leu Gly Ser Cys Ala Phe Arg Gly Thr Leu His Arg Ile Cys Cys
                 85                  90                  95

Arg Ala Cys Arg Ile Lys Lys Asn Lys Leu Arg Ile Tyr Phe Glu Ser
                100                 105                 110

Lys Lys Phe Val Phe Leu Leu Tyr Leu Ala Leu His Phe Leu Phe Ser
            115                 120                 125

Ser Lys Ile Asn Thr Leu Leu Gln Asp Phe Cys Leu
            130                 135                 140
```

<210> SEQ ID NO 67
<211> LENGTH: 141
<212> TYPE: PRT
<213> ORGANISM: Orangutan

<400> SEQUENCE: 67

```
Val Thr Pro Ala Met Arg Thr Phe Thr Val Leu Ala Ala Met Leu Leu
 1               5                  10                  15

Val Val Ala Leu Gln Ala Gln Ala Glu Pro Leu Arg Ala Arg Ala Asp
            20                  25                  30

Glu Thr Ala Ala Gln Glu Gln Pro Gly Ala Asp Asp Gln Glu Met Ala
            35                  40                  45

His Ala Phe Thr Trp Asp Glu Ser Ala Ala Leu Pro Leu Ser Asp Ser
 50                  55                  60

Ala Arg Gly Leu Arg Cys Ile Cys Arg Arg Gly Val Cys Arg Phe Leu
 65                  70                  75                  80
```

```
Arg His Leu Gly Ser Cys Ala Phe Arg Gly Thr Leu His Arg Ile Cys
                85                  90                  95

Cys Arg Ala Cys Arg Ile Lys Lys Asn Lys Leu Arg Ile Tyr Phe Glu
            100                 105                 110

Ser Lys Lys Phe Val Phe Leu Leu Tyr Leu Ala Leu His Phe Leu Phe
        115                 120                 125

Ser Ser Lys Ile Asn Thr Leu Leu Gln Asp Phe Cys Leu
    130                 135                 140
```

<210> SEQ ID NO 68
<211> LENGTH: 141
<212> TYPE: PRT
<213> ORGANISM: Orangutan

<400> SEQUENCE: 68

```
Val Thr Pro Ala Met Arg Thr Phe Thr Val Leu Ala Ala Met Leu Leu
  1               5                  10                  15

Val Val Ala Leu Gln Ala Gln Ala Glu Pro Leu Arg Ala Arg Ala Asp
                20                  25                  30

Glu Thr Ala Ala Gln Glu Gln Pro Gly Ala Asp Asp Gln Glu Met Ala
            35                  40                  45

His Ala Phe Thr Trp Asp Glu Ser Ala Ala Leu Pro Leu Ser Asp Ser
        50                  55                  60

Ala Arg Gly Leu Arg Cys Ile Cys Arg Arg Gly Val Cys Arg Leu Leu
 65                  70                  75                  80

Arg His Phe Gly Ser Cys Ala Phe Arg Gly Thr Leu His Arg Ile Cys
                85                  90                  95

Cys Arg Ala Cys Arg Ile Lys Lys Asn Lys Leu Arg Ile Tyr Phe Glu
            100                 105                 110

Ser Lys Lys Phe Leu Phe Leu Leu Tyr Leu Ala Leu His Phe Leu Phe
        115                 120                 125

Ser Ser Lys Ile Asn Thr Leu Leu Gln Asp Phe Cys Leu
    130                 135                 140
```

<210> SEQ ID NO 69
<211> LENGTH: 140
<212> TYPE: PRT
<213> ORGANISM: Gorilla

<400> SEQUENCE: 69

```
Val Thr Pro Ala Met Arg Thr Phe Ala Leu Leu Thr Ala Met Leu Leu
  1               5                  10                  15

Leu Val Asp Leu Ala Gln Ala Glu Pro Leu Gln Ala Arg Ala Asp Glu
                20                  25                  30

Ala Ala Ala Gln Glu Gln Pro Gly Ala Asp Asp Gln Glu Met Ala His
            35                  40                  45

Ala Phe Thr Trp Asp Glu Ser Ala Ala Leu Pro Leu Ser Asp Ser Ala
        50                  55                  60

Arg Gly Leu Arg Cys Ile Cys Gly Arg Gly Ile Cys Arg Leu Leu Arg
 65                  70                  75                  80

Arg Phe Gly Ser Cys Ala Phe Arg Gly Thr Leu His Arg Ile Cys Cys
                85                  90                  95

Arg Ala Cys Arg Ile Lys Lys Asn Lys Leu Arg Ile Tyr Phe Glu Thr
            100                 105                 110

Lys Lys Phe Leu Leu Leu Leu Tyr Leu Val Leu His Phe Leu Phe Ser
        115                 120                 125
```

```
Ser Lys Ile Asn Thr Leu Leu Gln Asp Phe Cys Leu
    130                 135                 140

<210> SEQ ID NO 70
<211> LENGTH: 141
<212> TYPE: PRT
<213> ORGANISM: Champanzee

<400> SEQUENCE: 70

Val Thr Pro Ala Met Arg Thr Phe Ala Leu Leu Thr Ala Met Leu Leu
  1               5                  10                  15

Leu Val Ala Leu Ala Gln Ala Glu Pro Leu Gln Ala Arg Ala Asp Glu
                 20                  25                  30

Ala Ala Ala Gln Glu Gln Pro Gly Ala Asp Asp Gln Glu Met Ala His
             35                  40                  45

Ala Phe Thr Trp Asp Glu Ser Ala Ala Leu Pro Leu Ser Asp Ser Ala
         50                  55                  60

Arg Gly Leu Arg Cys Ile Gly Gly Arg Gly Ile Cys Gly Leu Leu Gln
 65                  70                  75                  80

Arg Arg Phe Gly Ser Cys Ala Phe Arg Gly Thr Leu His Arg Ile Cys
                 85                  90                  95

Cys Arg Ala Cys Arg Ile Lys Lys Asn Lys Leu Arg Ile Tyr Ser Glu
             100                 105                 110

Ser Lys Lys Phe Leu Leu Leu Tyr Leu Val Leu His Phe Leu Phe
         115                 120                 125

Ser Ser Lys Ile Asn Thr Leu Leu Gln Asp Phe Ser Leu
    130                 135                 140

<210> SEQ ID NO 71
<211> LENGTH: 141
<212> TYPE: PRT
<213> ORGANISM: Chimpanzee

<400> SEQUENCE: 71

Val Thr Pro Ala Met Arg Thr Phe Ala Leu Leu Thr Ala Met Leu Leu
  1               5                  10                  15

Leu Val Ala Leu Ala Gln Ala Glu Pro Leu Gln Ala Arg Ala Asp Glu
                 20                  25                  30

Ala Ala Ala Gln Glu Gln Pro Gly Ala Asp Asp Gln Glu Met Ala His
             35                  40                  45

Ala Phe Thr Trp Asp Glu Ser Ala Ala Leu Pro Leu Ser Asp Ser Ala
         50                  55                  60

Arg Gly Leu Arg Cys Ile Gly Gly Arg Gly Ile Cys Gly Leu Leu Gln
 65                  70                  75                  80

Arg Arg Val Gly Ser Cys Ala Phe Arg Gly Thr Leu His Arg Ile Cys
                 85                  90                  95

Cys Arg Ala Cys Arg Ile Lys Lys Asn Lys Leu Arg Ile Tyr Ser Glu
             100                 105                 110

Ser Lys Lys Phe Leu Leu Leu Leu Tyr Leu Val Leu His Phe Leu Phe
         115                 120                 125

Ser Ser Lys Ile Asn Thr Ser Leu Gln Asp Phe Ser Leu
    130                 135                 140

<210> SEQ ID NO 72
<211> LENGTH: 141
<212> TYPE: PRT
<213> ORGANISM: Rhesus monkey
```

```
<220> FEATURE:
<221> NAME/KEY: VARIANT
<222> LOCATION: 113
<223> OTHER INFORMATION: Xaa = Any Amino Acid

<400> SEQUENCE: 72

Val Thr Pro Ala Met Arg Thr Phe Ala Leu Leu Thr Ala Met Leu Leu
 1               5                  10                  15

Leu Val Ala Leu His Ala Gln Ala Glu Ala Arg Gln Ala Arg Ala Asp
                20                  25                  30

Glu Ala Ala Gln Gln Gln Pro Gly Ala Asp Asp Gln Gly Met Ala
        35                  40                  45

His Ser Phe Thr Arg Pro Glu Asn Ala Ala Leu Pro Leu Ser Glu Ser
    50                  55                  60

Ala Arg Gly Leu Arg Cys Leu Cys Arg Arg Gly Val Cys Gln Leu Leu
65                  70                  75                  80

Arg Arg Leu Gly Ser Cys Ala Phe Arg Gly Leu Cys Arg Ile Cys Cys
                85                  90                  95

Arg Ala Ser Arg Ile Lys Lys Asn Thr Leu Arg Ser Tyr Phe Glu Ser
                100                 105                 110

Xaa Lys Lys Phe Leu Leu Leu Tyr Leu Val Leu Asn Phe Leu Phe
            115                 120                 125

Ser Ser Gln Ile Asn Thr Phe Ser Gln Asp Phe Cys Leu
        130                 135                 140

<210> SEQ ID NO 73
<211> LENGTH: 141
<212> TYPE: PRT
<213> ORGANISM: Pig-tailed macaque
<220> FEATURE:
<221> NAME/KEY: VARIANT
<222> LOCATION: 113
<223> OTHER INFORMATION: Xaa = Any Amino Acid

<400> SEQUENCE: 73

Val Thr Pro Ala Met Arg Thr Phe Ala Leu Leu Thr Ala Met Leu Leu
 1               5                  10                  15

Leu Val Ala Leu His Ala Gln Ala Glu Ala Arg Gln Ala Arg Ala Asp
                20                  25                  30

Glu Ala Ala Gln Gln Gln Pro Gly Ala Asp Asp Gln Gly Met Ala
        35                  40                  45

His Ser Phe Thr Arg Pro Glu Asn Ala Ala Leu Pro Leu Ser Glu Ser
    50                  55                  60

Ala Arg Gly Leu Arg Cys Ile Cys Arg Arg Gly Val Cys Gln Leu Leu
65                  70                  75                  80

Arg Arg Leu Gly Ser Cys Ala Phe Arg Gly Leu Cys Arg Ile Cys Cys
                85                  90                  95

Arg Ala Ser Arg Ile Lys Lys Asn Thr Leu Arg Ser Tyr Phe Glu Ser
                100                 105                 110

Xaa Lys Lys Phe Leu Leu Leu Tyr Leu Val Leu Asn Phe Leu Phe
            115                 120                 125

Ser Ser Gln Ile Asn Thr Phe Ser Gln Asp Phe Cys Leu
        130                 135                 140

<210> SEQ ID NO 74
<211> LENGTH: 9
<212> TYPE: PRT
<213> ORGANISM: Artificial Sequence
<220> FEATURE:
```

<223> OTHER INFORMATION: expansion of variant residues.

<400> SEQUENCE: 74

Arg Cys Ile Cys Gly Arg Arg Ile Cys
1               5

<210> SEQ ID NO 75
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 75

Arg Cys Leu Cys Gly Arg Arg Ile Cys
1               5

<210> SEQ ID NO 76
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 76

Arg Cys Ile Cys Arg Arg Arg Ile Cys
1               5

<210> SEQ ID NO 77
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 77

Arg Cys Ile Cys Thr Arg Arg Ile Cys
1               5

<210> SEQ ID NO 78
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 78

Arg Cys Ile Cys Val Arg Arg Ile Cys
1               5

<210> SEQ ID NO 79
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 79

Arg Cys Ile Cys Gly Leu Arg Ile Cys
1               5

<210> SEQ ID NO 80
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 80

Arg Cys Ile Cys Gly Arg Arg Val Cys
1               5

<210> SEQ ID NO 81
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 81

Arg Cys Ile Cys Gly Arg Arg Phe Cys
1               5

<210> SEQ ID NO 82
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 82

Arg Cys Leu Cys Arg Arg Arg Val Cys
1               5

<210> SEQ ID NO 83
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 83

Arg Cys Leu Cys Thr Arg Arg Ile Cys
1               5

<210> SEQ ID NO 84
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 84

Arg Cys Leu Cys Val Arg Arg Ile Cys
1               5

<210> SEQ ID NO 85
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 85

Arg Cys Leu Cys Gly Leu Arg Val Cys
1               5

<210> SEQ ID NO 86
<211> LENGTH: 9
<212> TYPE: PRT
<213> ORGANISM: Artificial Sequence
<220> FEATURE:
<223> OTHER INFORMATION: expansion of variant residues.

```
<400> SEQUENCE: 86

Arg Cys Leu Cys Gly Arg Arg Val Cys
 1               5

<210> SEQ ID NO 87
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 87

Arg Cys Leu Cys Gly Arg Arg Phe Cys
 1               5

<210> SEQ ID NO 88
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 88

Arg Cys Ile Cys Arg Arg Arg Val Cys
 1               5

<210> SEQ ID NO 89
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 89

Arg Cys Ile Cys Arg Arg Arg Phe Cys
 1               5

<210> SEQ ID NO 90
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 90

Arg Cys Ile Cys Thr Arg Arg Val Cys
 1               5

<210> SEQ ID NO 91
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 91

Arg Cys Ile Cys Thr Arg Arg Phe Cys
 1               5

<210> SEQ ID NO 92
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 92
```

Arg Cys Ile Cys Thr Leu Arg Ile Cys
1               5

<210> SEQ ID NO 93
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 93

Arg Cys Ile Cys Val Leu Arg Phe Cys
1               5

<210> SEQ ID NO 94
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 94

Arg Cys Ile Cys Arg Leu Arg Ile Cys
1               5

<210> SEQ ID NO 95
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 95

Arg Cys Ile Cys Val Arg Arg Val Cys
1               5

<210> SEQ ID NO 96
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 96

Arg Cys Ile Cys Gly Arg Arg Phe Cys
1               5

<210> SEQ ID NO 97
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 97

Arg Cys Ile Cys Gly Leu Arg Phe Cys
1               5

<210> SEQ ID NO 98
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 98

```
Arg Cys Ile Cys Gly Leu Arg Val Cys
 1               5

<210> SEQ ID NO 99
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 99

Arg Cys Leu Cys Arg Leu Arg Ile Cys
 1               5

<210> SEQ ID NO 100
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 100

Arg Cys Leu Cys Arg Arg Arg Val Cys
 1               5

<210> SEQ ID NO 101
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 101

Arg Cys Leu Cys Arg Arg Arg Phe Cys
 1               5

<210> SEQ ID NO 102
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 102

Arg Cys Leu Cys Thr Leu Arg Ile Cys
 1               5

<210> SEQ ID NO 103
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 103

Arg Cys Leu Cys Gly Arg Arg Val Cys
 1               5

<210> SEQ ID NO 104
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 104

Arg Cys Leu Cys Thr Arg Arg Phe Cys
```

<210> SEQ ID NO 105
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 105

Arg Cys Leu Cys Val Leu Arg Ile Cys
1               5

<210> SEQ ID NO 106
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 106

Arg Cys Leu Cys Val Arg Arg Val Cys
1               5

<210> SEQ ID NO 107
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 107

Arg Cys Ile Cys Gly Arg Arg Ile Cys
1               5

<210> SEQ ID NO 108
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 108

Arg Cys Ile Cys Arg Leu Arg Val Cys
1               5

<210> SEQ ID NO 109
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 109

Arg Cys Ile Cys Arg Leu Arg Phe Cys
1               5

<210> SEQ ID NO 110
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 110

Arg Cys Ile Cys Thr Leu Arg Val Cys
1               5

<210> SEQ ID NO 111
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 111

Arg Cys Ile Cys Thr Leu Arg Phe Cys
 1               5

<210> SEQ ID NO 112
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 112

Arg Cys Ile Cys Val Leu Arg Val Cys
 1               5

<210> SEQ ID NO 113
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 113

Arg Cys Ile Cys Val Leu Arg Phe Cys
 1               5

<210> SEQ ID NO 114
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 114

Arg Cys Leu Cys Gly Leu Arg Val Cys
 1               5

<210> SEQ ID NO 115
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 115

Arg Cys Leu Cys Gly Leu Arg Ile Cys
 1               5

<210> SEQ ID NO 116
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 116

Arg Cys Leu Cys Thr Leu Arg Val Cys
 1               5

<210> SEQ ID NO 117
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 117

Arg Cys Leu Cys Thr Leu Arg Ile Cys
1               5

<210> SEQ ID NO 118
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 118

Arg Cys Leu Cys Val Leu Arg Val Cys
1               5

<210> SEQ ID NO 119
<211> LENGTH: 9
<212> TYPE: PRT
<213> ORGANISM: Artificial Sequence
<220> FEATURE:
<223> OTHER INFORMATION: expansion of variant residues.

<400> SEQUENCE: 119

Arg Cys Leu Cys Val Leu Arg Ile Cys
1               5

<210> SEQ ID NO 120
<211> LENGTH: 437
<212> TYPE: DNA
<213> ORGANISM: Homo sapiens

<400> SEQUENCE: 120
gtcaccccag ccatgaggac cttcgccctc ctcactgcca tgcttctcct ggtggccctg      60
taggctcagg cggagccact tcaggcaaga gctgatgaag ctgcagccca ggagcagcct     120
ggagcagatg atcaggaaat ggctcatgcc tttacatggc atgaaagtgc cgctcttccg     180
ttttcagtca gactcagcga gaggcttgag gtgcatttgc ggaagaggaa tttgccgttt     240
gttataacgt cgctttgggt cctgcgcctt tcgtggtaca ctccaccggg tctgctgccg     300
ctgaacttgc agaatcaaga aaataagct cagaatttac tttgagagtt aaaagaaatt     360
cttgttactc ctgtaccttg tcctccattt ccttttctca tccaaaataa ataccttgtt     420
gcaagatttc tctcttt                                                    437

<210> SEQ ID NO 121
<211> LENGTH: 118
<212> TYPE: PRT
<213> ORGANISM: Homo sapiens

<400> SEQUENCE: 121

Val Thr Pro Ala Met Arg Thr Phe Ala Leu Leu Thr Ala Met Leu Leu
1               5                   10                  15

Leu Val Ala Leu Ala Gln Ala Glu Pro Leu Gln Ala Arg Ala Asp Glu
                20                  25                  30

Ala Ala Ala Gln Glu Gln Ser Asp Ser Ala Arg Gly Leu Arg Cys Ile
            35                  40                  45

```
Cys Gly Arg Gly Ile Cys Arg Leu Leu Arg Arg Phe Gly Ser Cys Ala
         50                  55                  60

Phe Arg Gly Thr Leu His Arg Val Cys Cys Arg Thr Cys Arg Ile Lys
 65                  70                  75                  80

Lys Asn Lys Leu Arg Ile Tyr Phe Glu Ser Lys Phe Leu Leu Leu
                 85                  90                  95

Leu Tyr Leu Val Leu His Phe Leu Phe Ser Ser Lys Ile Asn Thr Leu
                100                 105                 110

Leu Gln Asp Phe Ser Leu
         115

<210> SEQ ID NO 122
<211> LENGTH: 437
<212> TYPE: DNA
<213> ORGANISM: Homo sapiens

<400> SEQUENCE: 122
gtcaccccag ccatgaggac ctttgccctc ctcactgcca tgcttctcct ggtggccctg      60
taggctcagg cagagccact tcaggcaaga gctgatgaag ctgcagccca ggagcagcct    120
ggagcagatg atcaggaaat ggctcatgcc tttacatggc atgaaagtgc cgctcttccg    180
ctttcagtca gactcagcga gaggcttgag gtgcatttgc ggaagaagaa tttgccgttt    240
gttataacgt cgctttgggt cctgcgcctt tcgtggtaca ctccaccgga tctgctgccg    300
ctgagcttgc agaatcaaga aacataagct cagaatttac tttgagagtt aaaagaaatt    360
cttgttactc ctgtaccttg cctccatttc cttttctca tccaaaataa ataccttgtt    420
gcaagatttc tctcttt                                                   437

<210> SEQ ID NO 123
<211> LENGTH: 141
<212> TYPE: PRT
<213> ORGANISM: Homo sapiens

<400> SEQUENCE: 123

Val Thr Pro Ala Met Arg Thr Phe Ala Leu Leu Thr Ala Met Leu Leu
 1               5                  10                  15

Leu Val Ala Leu Ala Gln Ala Glu Pro Leu Gln Ala Arg Ala Asp Glu
                 20                  25                  30

Ala Ala Ala Gln Glu Gln Pro Gly Ala Asp Asp Gln Glu Met Ala His
             35                  40                  45

Ala Phe Thr Trp His Glu Ser Ala Ala Leu Pro Leu Ser Ser Asp Ser
 50                  55                  60

Ala Arg Gly Leu Arg Cys Ile Cys Gly Arg Arg Ile Cys Arg Leu Leu
 65                  70                  75                  80

Arg Arg Phe Gly Ser Cys Ala Phe Arg Gly Thr Leu His Arg Ile Cys
                 85                  90                  95

Cys Arg Ala Cys Arg Ile Lys Lys His Lys Leu Arg Ile Tyr Phe Glu
                100                 105                 110

Ser Lys Lys Phe Leu Leu Leu Tyr Leu Val Leu His Phe Leu Phe
                115                 120                 125

Ser Ser Lys Ile Asn Thr Leu Leu Gln Asp Phe Ser Leu
        130                 135                 140

<210> SEQ ID NO 124
<211> LENGTH: 437
<212> TYPE: DNA
```

<400> SEQUENCE: 124

```
gtcaccccag ccatgaggac ctttgccctc ctcactgcca tgcttctcct ggtggccctg     60
taggctcagg cagagccact tcaggcaaga gctgatgaag ctgcagccca ggagcagcct    120
ggagcagatg atcaggaaat ggctcatgcc tttacatggc atgaaagtgc cgctcttccg    180
ctttcagtca gactcagcga gaggcttgag gtgcatttgc ggaagaggaa tttgccgttt    240
gttataacgt cgctttgggt cctgcgcctt tcgtggtaca ctccaccgga tctgctgccg    300
ctgagcttgc agaatcaaga aacataagct cagaatttac tttgagagtt aaaagaaatt    360
cttgttactc ctgtaccttg tcctccattt ccttttctca tccaaaataa ataccttgtt    420
gcaagatttc tctcttt                                                   437
```

<210> SEQ ID NO 125
<211> LENGTH: 141
<212> TYPE: PRT
<213> ORGANISM: Homo sapiens

<400> SEQUENCE: 125

```
Val Thr Pro Ala Met Arg Thr Phe Ala Leu Leu Thr Ala Met Leu Leu
  1               5                  10                  15
Leu Val Ala Leu Ala Gln Ala Glu Pro Leu Gln Ala Arg Ala Asp Glu
             20                  25                  30
Ala Ala Ala Gln Glu Gln Pro Gly Ala Asp Asp Gln Glu Met Ala His
         35                  40                  45
Ala Phe Thr Trp His Glu Ser Ala Ala Leu Pro Leu Ser Ser Asp Ser
     50                  55                  60
Ala Arg Gly Leu Arg Cys Ile Cys Gly Arg Gly Ile Cys Arg Leu Leu
 65                  70                  75                  80
Arg Arg Phe Gly Ser Cys Ala Phe Arg Gly Thr Leu His Arg Ile Cys
                 85                  90                  95
Cys Arg Ala Cys Arg Ile Lys Lys His Lys Leu Arg Ile Tyr Phe Glu
            100                 105                 110
Ser Lys Lys Phe Leu Leu Leu Tyr Leu Val Leu His Phe Leu Phe
            115                 120                 125
Ser Ser Lys Ile Asn Thr Leu Leu Gln Asp Phe Ser Leu
            130                 135                 140
```

<210> SEQ ID NO 126
<211> LENGTH: 18
<212> TYPE: PRT
<213> ORGANISM: Artificial Sequence
<220> FEATURE:
<223> OTHER INFORMATION: RC101/103 hybrid

<400> SEQUENCE: 126

```
Gly Ile Cys Arg Cys Ile Cys Gly Lys Gly Ile Cys Arg Cys Tyr Cys
  1               5                  10                  15
Gly Arg
```

<210> SEQ ID NO 127
<211> LENGTH: 18
<212> TYPE: PRT
<213> ORGANISM: Artificial Sequence
<220> FEATURE:
<223> OTHER INFORMATION: K Retrocyclin-1

<400> SEQUENCE: 127

```
Gly Ile Cys Lys Cys Ile Cys Gly Lys Gly Ile Cys Lys Cys Ile Cys
1               5                   10                  15

Gly Arg
```

<210> SEQ ID NO 128
<211> LENGTH: 18
<212> TYPE: PRT
<213> ORGANISM: Artificial Sequence
<220> FEATURE:
<223> OTHER INFORMATION: Retrocyclin 2A

<400> SEQUENCE: 128

```
Gly Ile Cys Arg Cys Ile Cys Gly Lys Arg Ile Cys Arg Cys Ile Cys
1               5                   10                  15

Gly Arg
```

<210> SEQ ID NO 129
<211> LENGTH: 18
<212> TYPE: PRT
<213> ORGANISM: Artificial Sequence
<220> FEATURE:
<223> OTHER INFORMATION: Retrocyclin 2B

<400> SEQUENCE: 129

```
Gly Ile Cys Arg Cys Ile Cys Gly Lys Lys Ile Cys Arg Cys Ile Cys
1               5                   10                  15

Gly Arg
```

<210> SEQ ID NO 130
<211> LENGTH: 18
<212> TYPE: PRT
<213> ORGANISM: Artificial Sequence
<220> FEATURE:
<223> OTHER INFORMATION: Retrocyclin 2C

<400> SEQUENCE: 130

```
Gly Ile Cys Arg Cys Ile Cys Gly Arg Lys Ile Cys Arg Cys Ile Cys
1               5                   10                  15

Gly Arg
```

<210> SEQ ID NO 131
<211> LENGTH: 18
<212> TYPE: PRT
<213> ORGANISM: Artificial Sequence
<220> FEATURE:
<223> OTHER INFORMATION: Retrocyclin 2D

<400> SEQUENCE: 131

```
Gly Ile Cys Arg Cys Ile Cys Gly Arg Arg Ile Cys Lys Cys Ile Cys
1               5                   10                  15

Gly Arg
```

<210> SEQ ID NO 132
<211> LENGTH: 18
<212> TYPE: PRT
<213> ORGANISM: Artificial Sequence
<220> FEATURE:
<223> OTHER INFORMATION: Retrocyclin 2E

<400> SEQUENCE: 132

```
Gly Ile Cys Lys Cys Ile Cys Gly Arg Arg Ile Cys Arg Cys Ile Cys
1               5                   10                  15
```

```
-continued

Gly Arg

<210> SEQ ID NO 133
<211> LENGTH: 18
<212> TYPE: PRT
<213> ORGANISM: Artificial Sequence
<220> FEATURE:
<223> OTHER INFORMATION: Retrocyclin 2F

<400> SEQUENCE: 133

Gly Ile Cys Arg Cys Ile Cys Gly Arg Arg Ile Cys Arg Cys Ile Cys
1               5                   10                  15

Gly Lys

<210> SEQ ID NO 134
<211> LENGTH: 18
<212> TYPE: PRT
<213> ORGANISM: Orangutan

<400> SEQUENCE: 134

Gly Val Cys Arg Cys Ile Cys Gly Arg Gly Val Cys Arg Cys Ile Cys
1               5                   10                  15

Arg Arg

<210> SEQ ID NO 135
<211> LENGTH: 18
<212> TYPE: PRT
<213> ORGANISM: Orangutan

<400> SEQUENCE: 135

Gly Val Cys Arg Cys Ile Cys Gly Arg Gly Val Cys Arg Cys Ile Cys
1               5                   10                  15

Gly Arg
```